United States Patent
Ohmoto et al.

(10) Patent No.: US 6,797,720 B2
(45) Date of Patent: Sep. 28, 2004

(54) 1,3,4-OXADIAZOLINE DERIVATIVE AND AN AGENT COMPRISING ITS DERIVATIVE AS ACTIVE INGREDIENT

(75) Inventors: Kazuyuki Ohmoto, Osaka (JP); Iori Itagaki, Nagano (JP)

(73) Assignee: ONO Pharmaceutical Co., Ltd., Osaka (JP)

(*) Notice: Subject to any disclaimer, the term of this patent is extended or adjusted under 35 U.S.C. 154(b) by 0 days.

(21) Appl. No.: 10/148,613

(22) PCT Filed: Dec. 1, 2000

(86) PCT No.: PCT/JP00/08515
§ 371 (c)(1),
(2), (4) Date: Aug. 28, 2002

(87) PCT Pub. No.: WO01/40204
PCT Pub. Date: Jun. 7, 2001

(65) Prior Publication Data
US 2003/0166574 A1 Sep. 4, 2003

(30) Foreign Application Priority Data
Dec. 3, 1999 (JP) ............................................. 11-344451

(51) Int. Cl.$^7$ ................. A61K 31/4245; C07D 271/113
(52) U.S. Cl. ....................................... 514/364; 548/144
(58) Field of Search ........................... 548/144; 514/364

(56) References Cited
FOREIGN PATENT DOCUMENTS

| WO | WO 98/24806 A2 | 6/1998 |
|---|---|---|
| WO | WO 98/48799 A | 11/1998 |
| WO | WO 98/49190 A2 | 11/1998 |
| WO | WO 99/54317 A1 | 10/1999 |

*Primary Examiner*—Richard L. Raymond
(74) *Attorney, Agent, or Firm*—Sughrue Mion, PLLC

(57) ABSTRACT

A 1,3,4-oxadiazoline derivative of formula (I)

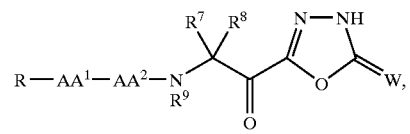

wherein W is oxygen, sulfer; R is hydrogen, alkyl, CycA, etc.; $AA^1$ is a single bond, amino acid residue, etc.; $AA^2$ is a single bond, amino acid residue, etc.; $R^7$ and $R^8$ are hydrogen, alkyl, etc.; $R^9$ is hydrogen, alkyl, etc., and a non-toxic salt thereof.

The compound of formula (I) has an inhibitory activity against cysteine protease and therefore it is useful as an agent for the prophylaxis and/or treatment of inflammatory diseases, diseases induced by apoptosis, diseases induced by disorders of immune responses, autoimmune diseases, diseases induced by decomposition of proteins which compose organism, shock, circulatory system disorders, blood coagulation systems disorders, malignant tumors, acquired immune deficiency syndrome (AIDS) and AIDS-related complex (ARC), parasitic diseases, nerve degeneration diseases, pulmonary disorders, bone resorption diseases, endocrinesthenia, etc.

17 Claims, No Drawings

1,3,4-OXADIAZOLINE DERIVATIVE AND AN AGENT COMPRISING ITS DERIVATIVE AS ACTIVE INGREDIENT

This application is a 371 of PCT/JP00/08515, filed Dec. 1, 2000.

TECHNICAL FIELD

The present invention relates to a 1,3,4-oxadiazoline derivative.

Particularly, the present invention relates to 1) a 1,3,4-oxadiazoline derivative of formula (I)

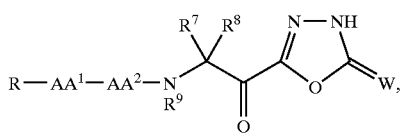

wherein all symbols are the same meanings as hereafter described, and a non-toxic salt thereof, 2) a method for the preparation thereof and 3) a pharmaceutical agent comprising the same as active ingredient.

BACKGROUND

Cysteine protease is a generic name of proteases which have a cysteine residue in the activity center and catalyze protein degradation thereat. In animal cells, a large number of cysteine proteases are known; for example, cathepsin family, calpain family, caspase-1, etc. Cysteine protease exists in various kinds of cells extensively and plays a basic and essential role in the homeostasis, such as conversion (processing) of precursor protein into its active form and degradation of proteins which have become out of use, etc. Until now, its physiological effects are being vigorously studied, and as the studies progress and characteristics of the enzymes are revealed, cysteine protease came to be taken as a cause of really various kinds of diseases.

It is revealed that cathepsin S (See J. Immunol., 161, 2731 (1998)) and cathepsin L (See J. Exp. Med., 183, 1331 (1996)) play a role in processing of major histocompatibility antigen class-II in antigen presenting cells which play an important role in the early stage of immune responses. In an experimental inflammatory response model induced by antigens, a specific inhibitor of cathepsin S showed an inhibitory effect (see J. Clin. Invest., 101, 2351 (1998)). It is also reported that in a leishmania-infected immune response model cathepsin B inhibitor inhibited an immune response and by means of this effect it inhibited the proliferation of protozoans (See J. Immunol., 161, 2120 (1998)). In vitro, a result is given that a calpain inhibitor and a cysteine protease inhibitor E-64 inhibited apoptosis which is induced by stimuli on T cell receptors (see J. Exp. Med., 178, 1693 (1993)). Therefore, it is conceivable that cysteine protease is much concerned with the progress of immune responses.

It is speculated that caspase-1 or a cysteine protease similar thereto occupies an important position in the mechanism of cell death including apoptosis. Therefore it is expected for a cysteine protease inhibitor to be used as an agent for the prophylaxis and/or treatment of those diseases concerning apoptosis, such as infectious diseases, deterioration or sthenia of immune function and brain function, tumors, etc. Diseases concerning apoptosis are, acquired immune deficiency syndrome (AIDS), AIDS-related complex (ARC), adult T cell leukemia, hairy cell leukemia, spondylopathy, respiratory apparatus disorder, arthritis, HIV or HTLV-1 related diseases such as uveitis, virus-related diseases such as hepatitis C, cancer, collagenosis (systemic lupus erythematosus, rheumatoid arthritis, etc.), autoimmune diseases (ulcerative colitis, Sjögren's syndrome, primary biliary cirrhosis, spontaneous thrombocytopenic purpura, autoimmune hemolytic anemia, myasthenia gravis, insulin dependent (type I) diabetes, etc.), diseases accompanied by thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type C, A, B, F, etc.) or hepatitis medicamentosus and cirrhosis, dementia (Alzheimer's diseases, Alzheimer's senile dementia, etc.), cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.

Moreover, caspase-1 is concerned with various inflammatory diseases and those diseases caused by immune disorders, by means of interleukin-1β (IL-1β) production. A lot of diseases are shown to be involved with caspase-1 including inflammatory diseases and autoimmune diseases listed below; inflammatory bowel diseases such as ulcerative colitis, insulin-dependent (type-I) diabetes, autoimmune thyroid diseases, infectious diseases, rejection of an organ transplantation, graft versus host diseases, psoriasis, periodontitis (above, see N. Eng. J. Med., 328, 106 (1993)), pancreatitis (see J. Interferon Cytokine Res., 17, 113 (1997)), hepatitis (see J. Leuko. Biol., 58,90 (1995)), glomerulonephritis (see Kidney Int., 47, 1303 (1995)), endocarditis (see Infect. Immun., 64, 1638 (1996)), myocarditis (see Br. Heart J., 72, 561 (1995)), systemic lupus erythematosus (see Br. J. Rheumatol., 34, 107 (1995)), Hashimoto's diseases (see Autoimmunity, 16, 141 (1993)), etc.), etc. Experimentally, it is reported that in liver injury model induced by lipopolysaccharide and D-galactosamine, a caspase-1 inhibitor depressed the symptoms, and it is expected that a caspase inhibitor shows an effect in sepsis, ischemic reperfusion and hepatitis gravis (see Am. J. Respir. Crit. Care Med., 159, 1308 (1999)).

It is also shown that cysteine protease is concerned with rheumatoid arthritis. IL-1β is shown to be concerned with this disease (see Arthritis Rheum., 39, 1092 (1996)), and in addition, as autoantibody toward calpastatin (endogenous calpain inhibitor) was found in the serum of the patients, it is considered that increase of calpain activity leads to the cause of diseases.

It is also known that cysteine protease causes a disease symptom by decomposing various proteins which compose the organism.

It is reported that cathepsin B plays a role in decomposing muscular protein in the chronic phase of sepsis (see J. Clin. Invest., 97, 1610 (1996)), and in decomposing muscular protein in myodystrophy model (see Biochem. J., 288, 643 (1992)). And it is also reported that calpain decomposes the myocyte cells protein of myodystrophy patients (see J. Biol. Chem., 270, 10909 (1995)).

In the ischemic reperfusion model, a result is given that calpain causes degeneration of brain tissues by means of degradation of protein kinase C-β (see J. Neurochem., 72, 2556 (1999)) and that a cathepsin B inhibitor inhibits nerve injury (see Eur. J. Neurosci., 10, 1723 (1998)).

In the brain ischemic model, it is known that the degradation of spectrin by calpain causes a damage and function disorder in the neurocyte (see Brain Res., 790, 1 (1998)) and it is reported that an IL-1β receptor antagonist relieved the symptoms (see Brain Res. Bull., 29, 243 (1992)).

In myocardial ischemic model it is confirmed that cathepsin B activity increases in the lesion (see Biochem. Med. Metab. Biol., 45, 6 (1991)).

In the experiment utilizing ischemic liver injury model, it proved that necrosis and apoptosis of hepacyte were induced by means of protein-decomposing activity of calpain (see Gastroenterology, 116, 168 (1999)).

Besides, it is known that calpain causes cornea turbid in cataract by means of degradation of crystalline (see Biol. Chem., 268, 137 (1993)) and that in the lesion of contracted gut mucosa model it was confirmed that the activity of cathepsin B, H and L increased (see JPEN. J. Parenter. Enteral. Nutr., 19, 187 (1995)) and it is shown that cysteine protease is a cause of the diseases resulting from such protein degradation.

It has been revealed that cysteine protease is concerned with systemic disorders of organs and tissues by shock.

It is shown that IL-1β is concerned with septic shock and systemic inflammatory response syndrome (see Igakuno Ayumi, 169, 850 (1994)) and besides, it is reported that in endotoxin shock model induced by lipopolysaccharide, a calpain inhibitor prevented circulatory system disorder, disorders of liver and pancreas and acidosis by means of inhibitory effect of activation of nuclear factor κB (see Br. J. Pharmacol., 121, 695 (1997)).

Since it is reported that calpain is concerned with platelet coagulation process and a calpain inhibitor prevented the coagulation of platelets (see Am. J. Physiol., 259, C862 (1990)), it is conceivable that a cysteine protease inhibitor is useful for the disorder by blood coagulation. From the fact that calpain activity increased in the serum of the patients of purpura (thrombocytopenia) resulting from marrow transplantation, it is conceivable that calpain is concerned with the actual disease symptoms (see Bone Marrow Transplant., 24, 641 (1999)). Caspase-1 inhibitor inhibited the apoptosis of blood vessel endothelial cells, which is seen in the early phase of purpura (thrombocytopenia) and is thought to be important for the progression of the pathology afterwards (see Am. J. Hematol., 59, 279 (1998)), so it is expected that a cysteine protease inhibitor makes effect on purpura and hemolytic uremic syndrome.

The effect of cysteine protease and its inhibitor is being investigated in the field of cancer and metastasis of cancer.

Since the proliferations of pancreas cancer cells (see Cancer Res., 59, 4551 (1999)) and acute myeloid leukemia cells (see Clin. Lab. Haematol., 21, 173 (1999)) were inhibited by an inhibitor or receptor antagonist of caspase-1, it is expected that caspase-1 activity is essential for the process of proliferation of tumor cells, and that an inhibitor thereof is effective for these cancers. Cathepsin B activity increased in colon cancer metastasis model (see Clin. Exp. Metastasis, 16, 159 (1998)). Cathepsin K protein expression was recognized in human breast cancer cells and the relationship of cathepsin K and bone metastasis is shown (Cancer Res., 57, 5386 (1997)). Also, a calpain inhibitor inhibited migration of the cells and it implied the possibility that calpain inhibition may inhibit metastasis of cancer (J. Biochem., 272, 32719 (1997)). From these, a cysteine protease inhibitor is presumed to show an inhibitory effect on the metastasis of various malignant tumors.

As to AIDS (see AIDS, 10, 1349 (1996)) and AIDS-related complex (ARC) (see Arch. Immunol. Ther. Exp. (Warsz), 41, 147 (1993)), it is shown that IL-1 is concerned with the progress of symptoms, so it is conceivable that cysteine protease inhibition leads to an effective therapy of AIDS and its complication.

Some parasites have cysteine protease activity in their body. Cysteine protease in the phagosome of malaria protozoan is an essential enzyme for supplying nutrition of the parasites. A result is given that the inhibitor of cysteine protease shows an inhibitory effect of the proliferation of the protozoan (see Blood, 87, 4448 (1996)). Thus, it is possible to apply the inhibitor of cysteine protease to malaria.

In Alzheimer-type dementia, it is said that adhesion of non-physiological protein called amyloid to brain is deeply involved with nervous function disorders. Cysteine protease has an activity of generating amyloid by decomposing its precursor protein. Clinically, it is shown that cathepsin B is an enzyme that possesses a processing activity of amyloid proteins in the brains of Alzheimer-type dementia patients (see Biochem. Biophys. Res. Commun., 177, 377 (1991)). Also, expressions of cathepsin B protein (see Virchows Arch. A. Pathol. Anat. Histpathol., 423, 185 (1993)), cathepsin S protein (see Am. J. Pathol., 146, 848 (1995)) and calpain protein (see Proc. Natl. Acad. Sci. USA, 90, 2628 (1993)) and increase of caspase-1 activity (see J. Neuropathol. Exp. Neurol., 58, 582 (1999)) were confirmed in the brain lesions. Besides, by the fact that calpain is concerned with the formation of paired helical filaments which accumulate in Alzheimer dementia patients and production of protein kinase C which stabilizes the protein by phosphorylation (see J. Neurochem., 66, 1539 (1996)) and by the knowledge that caspase is concerned with neurocyte death by β amyloid protein adhesion (see Exp. Cell Res., 234, 507 (1997)), it is implied that cysteine protease is concerned with the disease symptoms.

As to Huntington's chorea, cathepsin H activity increased in the patient's brain (see J. Neurol. Sci., 131, 65 (1995)), and the ratio of activated form of calpain increased (see J. Neurosci., 48, 181 (1997)). In Parkinson's diseases, the increase of expression of m-calpain was recognized in the mesencephalon of the patients (see Neuroscience, 73, 979 (1996)) and IL-1β protein was expressed in brain (see Neurosci. Let., 202, 17 (1995)). Therefore, it is speculated that cysteine protease is concerned with the genesis and progress of these diseases.

Besides, in the central nervous system, spectrin degradation by calpain is found in the process of injury on neurocyte observed in the traumatic brain injury model (see J. Neuropathol. Exp. Neurol., 58, 365 (1999)).

In spinal cord injured model it was recognized that in glia cells calpain messenger RNA increased and its activity increased in the lesion and the possibility was shown that calpain had much to do with the degeneration of myelin and actin after injury (see Brain Res., 816, 375 (1999)). And IL-1β was shown to be concerned with the genesis of multiple sclerosis (see Immunol. Today, 14, 260 (1993)). Therefore, it is conceivable that a cysteine protease inhibitor is promising as an agent for the treatment of these nerve-injuring diseases.

Normally, cathepsin S and cathepsin K do not exist in human arterial walls but it was confirmed that they expressed in arterial sclerosis lesion and they had an decomposing activity of alveolus elastica (see J. Clin. Invest., 102, 576 (1998)) and a calpain inhibitor and antisense of m-calpain inhibited the proliferation of human blood vessel smooth muscle cells and it is shown that m-calpain is concerned with the proliferation of smooth muscle (see Arteioscler. Thromb. Vssc. Biol., 18, 493 (1998)), so it is conceivable that a cysteine protease inhibitor is promising for the treatment of blood vessel lesion such as arteriosclerosis, restenosis after percutaneous transluminal coronary angioplasty (PTCA), etc.

It is reported that in liver, cathepsin B is activated in the process of injuring hepatocyte by bile acid (see J. Clin. Invest., 103, 137 (1999)) and so it is expected that a cysteine protease inhibitor is effective for cholestatic cirrhosis.

In lungs and respiratory system, it is shown that cathepsin S is an enzyme that plays a role in elastin degradation by alveolus macrophages (see J. Biol. Chem., 269, 11530 (1994)), so it is probable that cysteine protease is a cause of pulmonary emphysema. And it is also shown that lung injury (see J. Clin. Invest., 97, 963 (1996)), lung fibrosis (see Cytokine, 5, 57 (1993)) and bronchial asthma (see J. Immunol., 149, 3078 (1992)) are caused by production of IL-1β by caspase-1.

It is pointed out that cysteine protease is also concerned with diseases concerning bones and cartilages. Cathepsin K is specifically recognized in osteoclast and it has a decomposing activity against bone matrix (see J. Biol. Chem., 271, 12517 (1996)), so its inhibitor is expected to show an effect against osteoporosis, arthritis, rheumatoid arthritis, osteoarthritis, hypercalcemia and osteometastasis of cancer, where pathologic bone resorption is recognized. And since IL-1β is shown to be concerned with bone resorption and cartilage degradation, and a caspase-1 inhibitor and IL-1β receptor antagonist inhibit the bone resorption and symptoms of arthritis, a caspase-1 inhibitor and IL-1β receptor antagonist are expected to be effective for arthritis (see Cytokine, 8, 377 (1996)) and osteoporosis (J. Clin. Invest., 93, 1959 (1994)). And it is reported that IL-1β is also concerned with osteoarthritis (see Life Sci., 41, 1187 (1987)).

Cysteine protease is involved with production of various hormones. Since increase of messenger RNA of cathepsin S was recognized by stimuli of thytropin on thyroid epitheliocyte strains (see J. Biol. Chem., 267, 26038 (1992)), it is conceivable that a cysteine protease inhibitor is effective for hyperthyrodism.

Since quantity and activity of cathepsin B protein increased in the gingival sulcus liquid of periodontitis patients (see J. Clin. Periodontol., 25, 34 (1998)), it is pointed out that cysteine protease is concerned with periodontitis.

Therefore, it is expected that the compound that possesses the inhibitory activity of cysteine protease is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, HIV-related diseases such as hepatitis C, cancer, collagenosis (systemic lupus erythematosus, rheumatoid arthritis, etc.), ulcerative colitis, Sjögren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosus and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritablepneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), disease by degradation various proteins which compose the organism (myodystrophy, cataract, periodontitis, hepatocyte disease by bile acid such as cholestatic cirrhosis, etc.), decomposition of alveolus elastica such as pulmonary emphysema, ischemic diseases (brain ischemia, brain disorders (encephalopathy) by ischemic reperfusion, myocardial infarction, ischemic hepatopathy, etc.), shock (septic shock, systemic inflammatory response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as lung fibrosis, bone resorption diseases (osteoporosis, rheumatoid arthritis, arthritis, osteoarthritis, hypercalcemia, osteometastasis of cancer, etc.), endocrinesthenia such as hyperthyroidism.

On the other hand, what is the most important for inhibitors in inhibiting the activity of proteases is, the special reaction site which interacts with the amino acid residue that is the activity center of proteases. The surrounding structure of the reaction sites are represented by - - - P3P2P1-P1'P2'P3' - - - , centering peptide binding (P1-P1') of the reaction site, and at P1 site there exist amino acid residues fitting the substance specificity of proteases which the inhibitors aim. Some reaction sites against cysteine proteases are known, for Example, in the specification of WO99/54317, the followings are described;

P1 position against calpain I, II (norvaline, phenylalanine, etc.),

P1 position against calpain I (arginine, lysine, tyrosine, valine, etc.),

P1 position against papain (homophenylalanine, arginine, etc.

P1 position against cathepsin B-homophenylalanine, phenylalanine, tyrosine, etc.), P1 position against cathepsin S (valine, norleucine, phenylalanine, etc.), P1 position against cathepsin L (homophenylalanine, lysine, etc.), P1 position against cathepsin K (arginine, homophenylalanine, leucine, etc.), P1 position against caspase (aspartic acid).

On the other hand, in the specification of WO 98/49190, it is disclosed that the compound of formula (A) or a pharmaceutically acceptable salt thereof has an inhibitory activity against cysteine proteases,

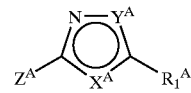

(A)

wherein $Z^A$ is a cysteine protease binding moiety;

$X^A$ and $Y^A$ are independently S, O or N, said N being optionally substituted with alkyl or alkenyl optionally substituted with 1–3 halogen atoms, or (C5–C6) aryl, arylalkyl or arylalkenyl optionally comprising 1–3 heteroatoms selected from N, O and S, and optionally substituted with halogen atom, cyano, nitro, haloalkyl, amino, aminoalkyl, dialkylamino, alkyl, alkenyl, alkynyl, alkoxy, haloalkoxy, carboxyl, carboalkoxy, arylcarboxamide, alkylthio or haloalkylthio;

$R_1^A$ is alkyl or alkenyl optionally substituted with 1–3 halo or hydroxy; alkylamino, dialkylamino, alkyldialkylamino; or cycloalkyl, alkylcycloalkyl, (C5–C12) aryl, (C5–C12) arylalkyl or (C5–C12) arylalkenyl optionally comprising 1–4 heteroatoms selected from N, O and S, and optionally substituted with halo, cyano, nitro, haloalkyl, amino, aminodialkyl, dialkylamino, alkyl, alkenyl, alkynyl, alkoxy, haloalkyl, carboxyl, carboalkoxy, alkylcarboxamide, (C5–C6) aryl, —O—(C5–C6) aryl, arylcarboxamide, alkylthio or haloalkylthio; and wherein at least one of Y or X is N.

And in the specification of WO98/24806, it is disclosed that the compound of formula (B)

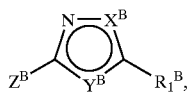
(B)

wherein $Z^B$ is a serine protease binding moiety;

$X^B$ and $Y^B$ are independently O, S or N, wherein N is optionally substituted with alkyl or alkenyl optionally substituted with 1–3 halogen atoms; when at least one of X or Y is N, (C5–C6) aryl, arylalkyl or arylalkenyl optionally comprising 1–3 heteroatoms selected from N, O and S, and optionally substituted with halo, cyano, nitro, hydroxyl, haloalkyl, amino, aminoalkyl, dialkylamino, alkyl, alkenyl, alkynyl, alkoxy, haloalkoxy, carboxyl, carboalkoxy, alkylcarboxamide, arylcarboxamide, alkylthio or haloalkylthio;

$R_1^B$ is alkyl, alkenyl or alkynyl which may be substituted with halo, cyano, nitro, hydroxyl, haloalkyl, amino, alkylamino, dialkylamino, alkylenedioxy, alkoxy, haloalkoxy, carboxyl, carboalkoxy, alkylcarboxyamide, arylcarboxyamide, or —O—(C5–C6) aryl; hydroxyl, amino, alkylamino, or dialkylamino; cycloalkyl, cycloalkenyl, alkylcycloalkyl, alkenylcycloalkyl, alkylcycloalkenyl, (C5–C12) aryl, (C5–C12) arylalkyl, (C5–C12) arylalkenyl, fused (C5–C12) arylcycloalkyl, or alkyl-fused (C5–C12) arylcycloalkyl which may contain 1–4 of heteroatom selected from N, O, or S, and which may be substituted with halo, cyano, nitro, hydroxyl, haloalkyl, amino, aminoalkyl, dialkylamino, alkyl, alkenyl, alkylendioxy, alkynyl, alkoxy, haloalkoxy, carboxyl, carboalkoxy, alkylcarboxyamide, (C5–C6) aryl, —O—(C5–C6) aryl, arylcarboxyamide, alkylthio, or haloalkylthio) has an inhibitory activity against serine proteases.

DISCLOSURE OF THE INVENTION

The present inventors have energetically investigated to find out such compounds that have cysteine protease inhibitory activity, and found out that the 1,3,4-oxadiazoline derivative of formula (I) accomplishes the purpose.

The 1,3,4-oxadiazoline derivative of formula (I) of the present invention is not known as a cysteine protease inhibitor at all.

The present invention relates to 1) a 1,3,4-oxadiazoline derivative of formula (I)

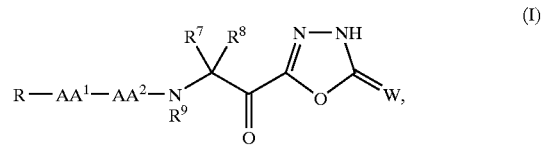
(I)

wherein W is oxygen or sulfur,

R is
 (i) hydrogen,
 (ii) C1–8 alkyl,
 (iii) CycA,
 (iv) C1–8 alkyl substituted with a group selected from halogen atom, CycA, nitro, $CF_3$ or cyano, (v)
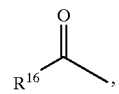

(vi)
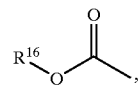

(vii)
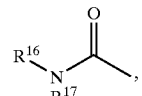

(viii)
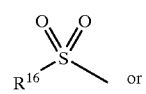 or (ix)
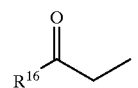

CycA is a mono-, bi- or tri-cyclic C3–15 carboring or mono-, bi- or tri-cyclic3–15 membered heteroring comprising 1–4 of nitrogen, 1–2 of oxygen and/or 1 of sulfur;

$R^{16}$ is
 (1) C1–8 alkyl,
 (2) C2–8 alkenyl,
 (3) C2–8 alkynyl,
 (4) CycA or
 (5) C1–8 alkyl, C2–8 alkenyl or C2–8 alkynyl substituted with a group selected from halogen, nitro, $CF_3$, cyano, CycA, $NR^{18}R^{19}$ and —NHC(O)—CycA;

$R^{17}$ is hydrogen or C1–4 alkyl, $R^{18}$ and $R^{19}$ are the same or different to represent hydrogen or C1–4 alkyl, $AA^1$ is (i) a single bond, or (ii)

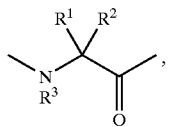

wherein $R^1$ and $R^2$ are the same or different to represent
(i) hydrogen,
(ii) C1–8 alkyl,
(iii) CycA or
(iv) C1–8 alkyl substituted with 1–5 of group selected from the following (1)~(8):
(1) —$NR^{21}R^{22}$, (2) —$OR^{23}$, (3) —$SR^{24}$, (4) —$COR^{25}$, (5) —$NR^{26}CONR^{21}R^{22}$, (6) guanidino, (7) CycA, (8) —$NR^{26}SO_2R^{21}$; or $R^1$ and $R^2$ are taken together to form C2–8 alkylene wherein one carbon atom may be replaced by oxygen, sulfur or —$NR^{20}$— and the alkylene may be substituted with —$NR^{21}R^{22}$ or —$OR^{23}$, $R^{20}$ is hydrogen, C1–4 alkyl, —COO—(C1–4 alkyl), phenyl or C1–4 alkyl substituted with phenyl, $R^{21}$, $R^{22}$, $R^{23}$, $R^{24}$ and $R^{26}$ are the same or different to represent hydrogen, C1–4 alkyl, phenyl or C1–4 alkyl substituted with phenyl, $R^{25}$ is C1–4 alkyl, phenyl, —$NR^{21}R^{22}$, wherein all symbols are the same meanings as above, —$OR^{23}$ wherein $R^{23}$ is the same meaning as above, or C1–4 alkyl substituted with phenyl, $R^3$ is hydrogen, C1–8 alkyl, phenyl or C1–8 alkyl substituted with phenyl or $R^3$ is taken together with $R^1$ to form C2–6 alkylene wherein one carbon atom may be replaced by oxygen, sulfur or —$NR^{20}$— and the alkylene may be substituted with —$NR^{21}R^{22}$ or —$OR^{23}$,) or when $AA^1$ is

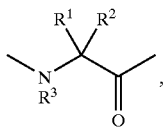

$AA^1$ and R may be taken together to form

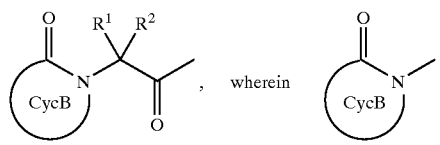, wherein is a 5–12 membered mono- or bi-cyclic heteroring and the other symbols are the same meanings as above, $AA^2$ is (i) a single bond, (ii)

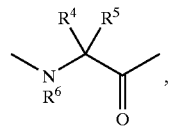

(iii)

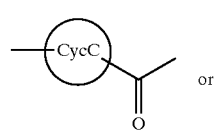  or (iv)

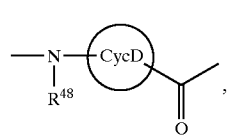, wherein $R^4$ and $R^5$ are the same or different to represent
(1) hydrogen,
(2) C1–8 alkyl,
(3) CycA or
(4) C1–8 alkyl substituted with 1–5 of group selected from the following (a)~(h)
(a) —$NR^{41}R^{42}$, (b) —$OR^{43}$, (c) —$SR^{44}$, (d) —$COR^{45}$, (e) —$NR^{46}CONR^{41}R^{42}$, (f) guanidino, (g) CycA, (h) —$NR^{46}SO_2R^{41}$; or $R^4$ and $R^5$ are taken together to form C2–8 alkylene, wherein one carbon atom may be replaced by oxygen, sulfur or —$NR^{40}$— and the alkylene may be substituted with —$NR^{41}R^{42}$ or —$OR^{43}$, $R^{40}$ is hydrogen, C1–4 alkyl, —COO—(C1–4 alkyl), phenyl or C1–4 alkyl substituted with phenyl, $R^{41}$, $R^{42}$, $R^{43}$, $R^{44}$ and $R^{46}$ are the same or different to represent hydrogen, C1–4 alkyl, phenyl or C1–4 alkyl substituted with phenyl, $R^{45}$ is C1–4 alkyl, phenyl, —$NR^{41}R^{42}$, wherein all symbols are the same meanings as above, —$OR^{43}$, wherein $R^{43}$ is the same meaning as above., or C1–4 alkyl substituted with phenyl, $R^6$ is hydrogen, C1–8 alkyl, phenyl or C1–8 alkyl substituted with phenyl or $R^6$ is taken together with $R^4$ to form C2–6 alkylene, wherein one carbon atom may be replaced by oxygen, sulfur or —$NR^{40}$— and the alkylene may be substituted with —$NR^{41}R^{42}$ or —$OR^{43}$, $R^{48}$ is hydrogen, C1–4 alkyl, phenyl or C1–4 alkyl substituted with phenyl or when $AA^1$ is a single bond, $R^{48}$ and R may be taken together to form C2–6 alkylene, wherein one carbon atom may be replaced by oxygen, sulfur or —$NR^{47}$, wherein $R^{47}$ is hydrogen or C1–4 alkyl, CycC is a 3–17 membered mono- or bi-cyclic heterring, CycD is a C3–14 mono- or bi-cyclic carboring or a 3–14 membered mono- or bi-cyclic heterring) or AA² and AA¹ may be taken together to form (i)

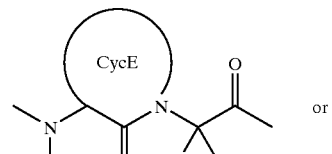

or (ii)

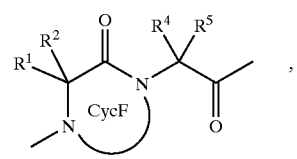

, wherein CycE is a 4–18 membered mono- or bi-cyclic heterring, and CycF is a 5–8 membered monocyclic heterring, and the other symbols are the same meanings as above, R⁷ and R⁸ are the same or different to represent
(i) hydrogen,
(ii) C1–8 alkyl,
(iii) CycA or
(iv) C1–8 alkyl substituted with 1–5 of group selected from the following (1)~(8);
(1) —NR⁶¹R⁶², (2) —OR⁶³, (3) —SR⁶⁴, (4) —COR⁶⁵, (5) —NR⁶⁶CONR⁶¹R⁶², (6) guanidino, (7) CycA, or (8) —NR⁶⁶SO₂R⁶¹, or R⁷ and R⁸ are taken together to form C2–8 alkylene wherein one carbon atom may be replaced by oxygen, sulfur or —NR⁶⁰— and the alkylene may be substituted with —NR⁶¹R⁶² or —OR⁶³, R⁶⁰ is hydrogen, C1–4 alkyl, —COO—(C1–4 alkyl), phenyl or C1–4 alkyl substituted with phenyl, R⁶¹, R⁶², R⁶³, R⁶⁴ and R⁶⁶ are the same or different to represent hydrogen, C1–4 alkyl, phenyl or C1–4 alkyl substituted with phenyl, R⁶⁵ is C1–4 alkyl, phenyl, —NR⁶¹R⁶², wherein all symbols are the same meanings as above, —OR⁶³, wherein R⁶³ is the same meaning as above, or C1–4 alkyl substituted with phenyl, R⁹ is hydrogen, C1–8 alkyl, phenyl or C1–8 alkyl substituted with phenyl or R⁹ is taken together with R⁷ to form C2–6 alkylene, wherein one carbon atom may be replaced by oxygen, sulfur or —NR⁶⁰— and the alkylene may be substituted with —NR⁶¹R⁶² or —OR⁶³, and, CycA is included in R, R¹, R², R⁴, R⁵, R⁷, R⁸ and R¹⁶ may be the same or different and CycA, CycB, CycC, CycD, CycE and CycF, independently, may be substituted with 1–5 of R²⁷:

R²⁷ is
(1) C1–8 alkyl,
(2) halogen,
(3) —NR¹¹R¹²,
(4) —OR¹³,
(5) a C5–10 mono- or bi-cyclic carboring,
(6) nitro,
(7) CF₃,
(8) cyano,
(9) a 5–10 membered mono- or bi-cyclic heterring
(10) —SR¹⁴,
(11) —COR¹⁵,
(12) oxo,
(13) —SO₂R¹⁵,
(14) —OCF₃ or
(15) C1–8 alkyl substituted with 1–5 of group selected from the following (a)~(m):
(a) halogen, (b) —NR¹¹R¹², (c) —OR¹³, (d) C5–10 mono- or bi-cyclic carboring, (e) nitro, (f) CF₃, (g) cyano, (h) 5–10 membered mono- or bi-cyclic heterring, (j) —SR¹⁴, (k) —COR¹⁵, (l) —SO₂R¹⁵, or (m) —OCF³, wherein R¹¹ and R¹² are the same or different to represent hydrogen, C1–4 alkyl, —COO—(C1–4 alkyl), phenyl or C1–4 alkyl substituted with phenyl, R¹³ and R¹⁴ are the same or different to represent hydrogen, C1–4 alkyl, phenyl or C1–4 alkyl substituted with phenyl, R¹⁵ is C1–4 alkyl, phenyl, —NR¹¹R¹² wherein all symbols are the same meanings as above, —OR¹³ wherein R¹³ is the same meaning as above, or C1–4 alkyl substituted with phenyl, or a non-toxic salt thereof, 2) a method for the preparation thereof and 3) a pharmaceutical agent comprising the same as active ingredient.

DETAILED DESCRIPTION OF THE PRESENT INVENTION

In the compound of formula (I), in the group

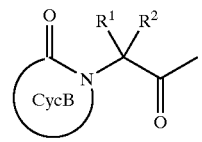

(which AA¹ and R together form),

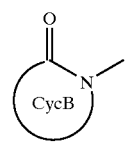

is a 5–12 membered heteroring containing 1–3 of nitrogen, 1 of oxygen, and/or 1 of sulfur (this heteroatom may be substituted with 1–5 of $R^{27}$).

And to describe

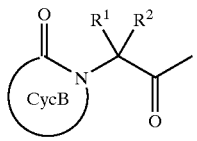

concretely, it is (i)

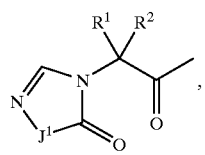

(ii)

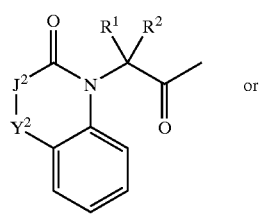

(iii)

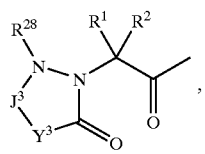

wherein $J^1$ is oxygen, sulfur or —$NR^{29}$— wherein $R^{29}$ is hydrogen, C1–4 alkyl, CycA or C1–4 alkyl substituted with CycA, C1–3 alkylene or C2–3 alkenylene, $J^2$ is a single bond or C1–2 alkylene, $Y^2$ is —N=CH—, —CH=N— or C1–2 alkylene, $J^3$ is carbonyl or C1–3 alkylene, $Y^3$ is C1–3 alkylene, oxygen or —$NR^{29}$— wherein $R^{29}$ is the same meaning as above, $R^{28}$ is hydrogen, C1–4 alkyl, CycA or C1–4 alkyl substituted with CycA, or $R^{28}$ is taken together with $R^1$ to form C2–4 alkylene, and the other symbols are the same meanings as above and each ring may be substituted with 1–5 of $R^{27}$.

In the compound of formula (I), in (iii)

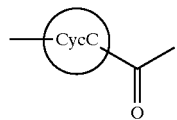

(which $AA^2$ represents), CycC is a 3–17 membered heteroring which contains 1–2 of nitrogen, 1 of oxygen and/or 1 of sulfur (this ring may be substituted with 1–5 of $R^{27}$).

And to describe

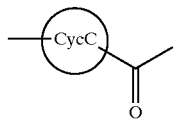

concretely, it is (iii-1)

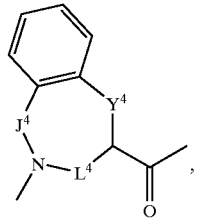

(iii-2)

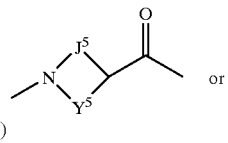

(iii-3)

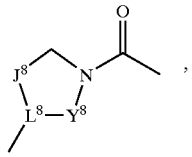

wherein $J^4$, $Y^4$ and $L^4$ are the same or different to represent a single bond or C1–3 alkylene (with proviso that $J^4$, $Y^4$ and $L^4$ do not represent a single bond at the same time, $J^5$ is C1–6 alkylene, $Y^5$ is a single bond, C1–3 alkylene or —$NR^{67}$—, wherein $R^{67}$ is hydrogen, C1–4 alkyl, phenyl or C1–4 alkyl substituted with phenyl, $J^8$ is C1–5 alkylene wherein one carbon atom may be replaced by oxygen, $Y^8$ is a single bond or C1–4 alkylene, $L^8$ is —N— or —CH—, and the other symbols are the same meanings as above and each ring may be substituted with 1–5 of $R^{27}$).

And in (iv)

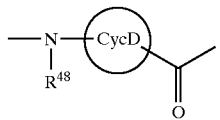

(which $AA^2$ represents), CycD is a C3–14 mono- or bi-cyclic carboring or a 3–14 membered heteroring which contains 1–2 of nitrogen, 1 of oxygen and/or 1 of sulfur (this carboring and heteroring may be substituted with 1–5 of $R^{27}$).

And to describe

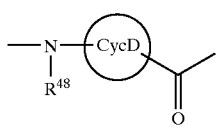

concretely, (iv-1)

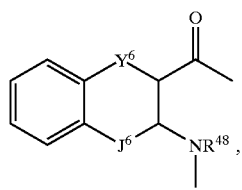

(iv-2)

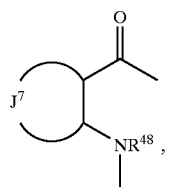

(iv-3)

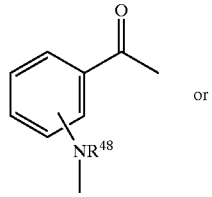 or (iv-4)

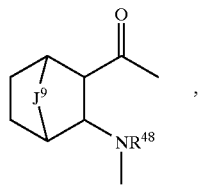

wherein $J^6$ and $Y^6$ are the same or different to represent a single bond or C1–3 alkylene, wherein $J^6$ and $Y^6$ do not represent a single bond at the same time, $J^7$ is C1–6 alkylene wherein one carbon atom may be replaced by oxygen, sulfur or —$NR^{67}$—, wherein $R^{67}$ is the same meaning as above, $J^9$ is C1–3 alkylene, oxygen, sulfur or —$NR^{67}$— wherein $R^{67}$ is the same meaning as above, and the other symbols are the same meanings as above and each ring may be replaced by 1–5 of $R^{27}$).

In the compound of formula (I), in (i)

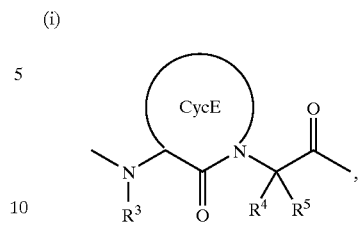

(which $AA^1$ and $AA^2$ together form), CycE is a 4–18 membered heteroring which contains 1–2 of nitrogen, 1 of oxygen and/or 1 of —$S(O)_p$— (this heteroring may be substituted with 1–5 of $R^{27}$).

And to describe

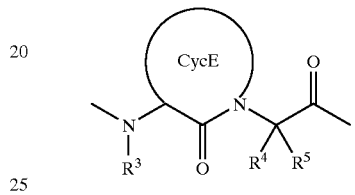

concretely, it is (i-1)

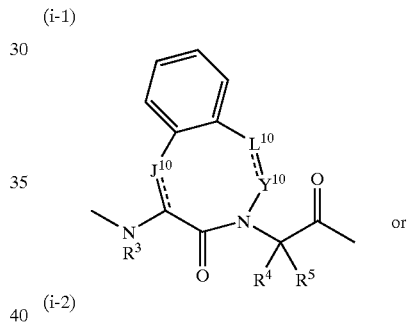 or (i-2)

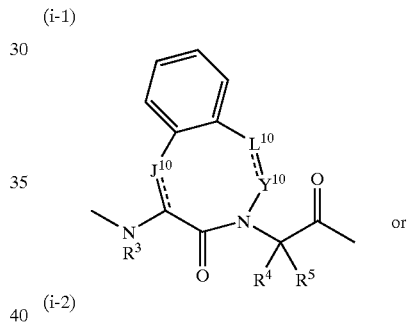

wherein

===== is a single bond or a double-bond, $J^{10}$ and $Y^{10}$ are the same or different to represent a single bond or C1–3 alkylene, $L^{10}$ is a single bond, C1–3alkylene, —$NR^{57}$—, wherein $R^{57}$ is hydrogen, C1–4 alkyl, phenyl or C1–4 alkyl substituted with phenyl, —N=, oxygen or —$S(O)_p$—, wherein p is 0 or an integer of 1~2), $J^{12}$ and $Y^{12}$ are the same or different to represent a single bond or C1–3 alkylene, $L^{12}$ is C1–3 alkylene, —$NR^{57}$—, wherein $R^{57}$ is the same meaning as above, —N=, =N—, oxygen or —$S(O)_p$—, wherein p is the same meaning as above, and the other symbols are the same meanings as above and each ring may be substituted with 1–5 of $R^{27}$).

And in (ii)

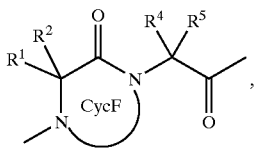

(which AA$^1$ and AA$^2$ together form), CycF is a 5–8 membered heteroring containing 2 of nitrogen.

And to describe

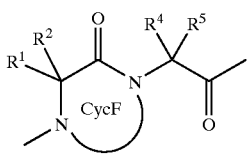

concretely, it is

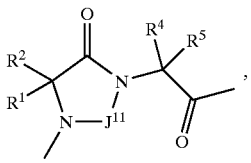

wherein J$^{11}$ is carbonyl or C2–4 alkylene and the other symbols are the same meanings as above and the ring therein may be substituted with 1–5 of R$^{27}$.

In the present specification, C1–4 alkyl is methyl, ethyl, propyl, butyl and isomers thereof.

In the present specification, C1–8 alkyl is methyl, ethyl, propyl, butyl, pentyl, hexyl, heptyl, octyl and isomers thereof.

In the present specification, C2–8 alkenyl is, ethyl, propyl, butyl, pentyl, hexyl, heptyl, octyl containing 1–3 of double bond and isomers thereof. For example, vinyl, propenyl, butenyl, hexenyl, hexadienyl, octadienyl, etc. are included.

In the present specification, C2–8 alkynyl is ethyl, propyl, butyl, pentyl, hexyl, heptyl, octyl containing 1–3 of triple bond and isomers thereof. For example, ethynyl, propynyl, butynyl, pentynyl, hexynyl, heptynyl, octynyl, etc. are included.

In the present specification, C1–4 alkyl substituted with phenyl is phenylmethyl, phenylethyl, phenylpropyl, phenylbutyl and isomers thereof.

In the present specification, C1–2 alkylene is, methylene, ethylene and isomers thereof.

In the present specification, C1–3 alkylene is, methylene, ethylene, trimethylene and isomers thereof.

In the present specification, C1–4 alkylene is methylene, ethylene, trimethylene, tetramethylene and isomers thereof.

In the present specification, C1–5 alkylene is methylene, ethylene, trimethylene, tetramethylene, pentamethylene and isomers thereof In the present specification, C1–6 alkylene is methylene, ethylene, trimethylene, tetramethylene, pentamethylene, hexamethylene and isomers thereof.

In the present specification, C2–4 alkylene is ethylene, trimethylene, tetramethylene and isomers thereof.

In the present specification, C2–6 alkylene is ethylene, trimethylene, tetramethylene, pentamethylene, hexamethylene and isomers thereof.

In the present specification, C2–8 alkylene is ethylene, trimethylene, tetramethylene, pentamethylene, hexamethylene, heptamethylene, octamethylene and isomers thereof.

In the present specification, C2–6 alkylene whose one carbon atom may be replaced by oxygen, sulfur, —NR$^{20}$—, —NR$^{40}$—, —NR$^{47}$— or —NR$^{60}$— is ethylene, trimethylene, tetramethylene, pentamethylene, hexamethylene and isomers thereof and one carbon atom thereof maybe replaced by oxygen, sulfur, —NR$^{20}$—, —NR$^{40}$—, —NR$^{47}$—, or —NR$^{60}$—, for example, such groups are —CH$_2$—O—CH$_2$—, —CH$_2$—CH$_2$—O—CH$_2$—, —CH$_2$—CH$_2$—S—CH$_2$—, —CH$_2$—CH$_2$—NH—CH$_2$—, —CH$_2$—CH$_2$—O—CH$_2$—CH$_2$—, —CH$_2$—CH$_2$—S—CH$_2$—CH$_2$—, —CH$_2$—CH$_2$—NH—CH$_2$—CH$_2$—, —CH$_2$—CH$_2$—N(CH$_3$)—CH$_2$—CH$_2$—, etc.

In the present specification, C2–8 alkylene whose carbon atom may be replaced by oxygen, sulfur, —NR$^{20}$—, —NR$^{40}$— or —NR$^{60}$— is ethylene, trimethylene, tetramethylene, pentamethylene, hexamethylene, heptamethylene, octamethylene and isomers thereof and one carbon atom thereof may be replaced by oxygen, sulfur, —NR$^{20}$—, —NR$^{40}$— or —NR$^{60}$—, for example, —CH$_2$—O—CH$_2$—, —CH$_2$—CH$_2$—O—CH$_2$—, —CH$_2$—CH$_2$—S—CH$_2$—, —CH$_2$—CH$_2$—NH—CH$_2$—, —CH$_2$—CH$_2$—O—CH$_2$—CH$_2$—, —CH$_2$—CH$_2$—S—CH$_2$—CH$_2$—, —CH$_2$—CH$_2$—NH—CH$_2$—CH$_2$—, —CH$_2$—CH$_2$—N(CH$_3$)—CH$_2$—CH$_2$—, etc.

In the present specification, C2–3 alkenylene means vinylene and allylene and isomers thereof.

In the present specification, halogen means chlorine, fluorine, bromine, iodine atom.

In the present specification, C5–10 mono- or bi-cyclic carboring is C5–10 mono- or bi-cyclic carboaryl or partially or completely saturated one thereof. For example, cyclopentane, cyclohexane, cycloheptane, cyclopentene, cyclohexene, cyclopentadiene, cyclohexadiene, benzene, pentalene, indene, naphthalene, azulene, perhydropentalene, perhydroindene, perhydronaphthalene, perhydroazulene, adamantyl ring etc. are included.

In the present specification, C3–15 mono-, bi-or tri-cyclic carboring is C3–15 mono-, bi-or tri-cyclic carboaryl or partially or completely saturated one thereof. For example, cyclopropane, cyclobutane, cyclopentane, cyclohexane, cycloheptane, cyclopentene, cyclohexene, cyclopentadiene, cyclohexadiene, benzene, pentalene, indene, naphthalene, azulene, fluorene, phenanthrene, anthracene, acenaphthylene, biphenylene, perhydropentalene, perhydroindene, perhydronaphthalene, perhydroazulene, perhydrofluorene, perhydrophenanthrene, perhydroanthracene, perhydroacenaphthylene, perhydrobiphenylene, adamantyl ring etc. are included.

In the present specification, 5–10 membered mono- or bi-cyclic heteroring containing 1–4 of nitrogen, 1 of oxygen and/or 1 of sulfur is 5–10 membered mono- or bi-cyclic heteroaryl containing 1–4 of nitrogen, 1 of oxygen and/or 1 of sulfur or partially or completely saturated one thereof.

Above 5–10 membered mono- or bi-cyclic heteroaryl containing 1–4 of nitrogen, 1 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, thiophene, thiaine (thiopyrane), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, etc.

Above partially or completely saturated 5–10 membered mono- or bi-cyclic heteroaryl containing 1–4 of nitrogen, 1 of oxygen and/or 1 of sulfur is, for example, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetrahydropyrane, dihydrothiophene, tetrahydrothiophene, dihydrothiaine (dihydrothiopyrane), tetrahydrothiaine (tetrahydrothiopyrane), oxazoline (dihydroxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzoturan, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, etc.

In the present specification, 3–15 membered mono-, bi- or tri-cyclic heteroring containing 1–4 of nitrogen, 1–2 of oxygen and/or 1 of sulfur is 3–15 membered mono-, bi- or tri-cyclic heteroaryl containing 1–4 of nitrogen, 1–2 of oxygen and/or 1 of sulfur or partially or completely saturated one thereof.

Above 3–15 membered mono-, bi- or tri-cyclic heteroaryl containing 1–4 of nitrogen, 1–2 of oxygen and/or 1 of sulfur is, for example, pyrrole, imidazole, triazole, tetrazole, pyrazole, pyridine, pyrazine, pyrimidine, pyridazine, azepine, diazepine, furan, pyrane, oxepine, oxazepine, thiophene, thiaine (thiopyrane), thiepine, oxazole, isoxazole, thiazole, isothiazole, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzoxadiazole, benzothiazole, benzimidazole, carbazole, acridine ring etc.

Above described partially or completely saturated 3–15 membered mono-, bi- or tri-cyclic heteroaryl containing 1–4 of nitrogen, 1–2 of oxygen and/or 1 of sulfur is, aziridine, oxirane, azetidine, oxetane, thiirane, thietane, pyrroline, pyrrolidine, imidazoline, imidazolidine, triazoline, triazolidine, tetrazoline, tetrazolidine, pyrazoline, pyrazolidine, piperidine, piperazine, tetrahydropyridine, tetrahydropyrimidine, tetrahydropyridazine, dihydrofuran, tetrahydrofuran, dihydropyrane, tetnahydropyrane, dihydrothiophene, tetrahydrothiophene, dihydrothiaine (dihydrothiopyrane), tetrahydrothiaine (tetrahydrothiopyrane), oxazoline (dihydroxazole), oxazolidine (tetrahydroxazole), dihydroisoxazole, tetrahydroisoxazole, oxadiazoline (dihydroxadiazole), oxadiazolidine (tetrahydroxadiazole), thiazoline (dihydrothiazole), thiazolidine (tetrahydrothiazole), dihydroisothiazole, tetrahydroisothiazole, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophihalazine, tetrahyckophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobeuzimidazole, perhydrobenzimidazole, benzoxazepine, benzoxadiazepine, benzothiazepine, benzothiadiazepine, benzoazepine, benzodiazepine, indoloxazepine, indolotetrahydroxazepine, indoloxadiazepine, indolotetrahydroxadiazepine, indolothiazepine, indolotetrahydrothiazepine, indolotbiadiazepine, indolotetrahydrothiadiazepine, indoloazepme, indolotetrahydroazepine, indolodiazepine, indolotetrahydrodiazepine, benzofurazane, benzothiadiazole, benzotriazole, camphor, imidazothiazole, dihydrocarbazole, tetrahydrocarbazole, perhydrocarbazole, dihydroacridine, tetrahydroacridine, perhydroacridine, dioxolane, dioxane, dioxazine ring, etc.

In the present specification, 5–12 membered heteroring containing 1–3 of nitrogen, 1 of oxygen and/or 1 of sulfur, i.e.

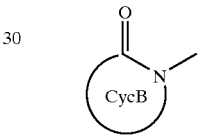

is, for example, a ring represented by

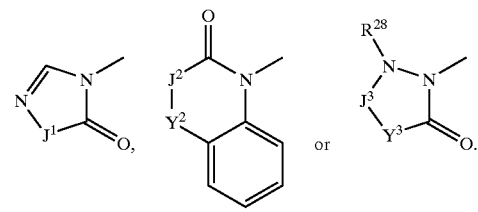

More particularly, 2-oxo-1,3,4-triazoline, 5-oxo-1,2,4-oxadiazoline, 5-oxo-1,2,4-thiadiazoline, 4-oxoimidazoline, 3,4-dihydro-4-oxopyrimidine, 3,4,5,6-tetrahydro-4-oxopyrimidine, 2-oxoindoline, 2-oxo-tetrahydroquinoline, 1,2-dihydro-2-oxoquinazoline, 1,2-dihydro-2-oxoquinoxaline, 3-oxopyrazolidine, perhydro-3-oxopyridazine, 2-oxo-1,3,4-oxadiazolidine, perhydro-2-oxo-1,3,4-oxadiazine, etc. are included.

In the specification, 3–17 membered heteroring containing 1–2 of nitrogen, 1 of oxygen and/or 1 of sulfur, i.e. CycC is, for example, a ring represented by

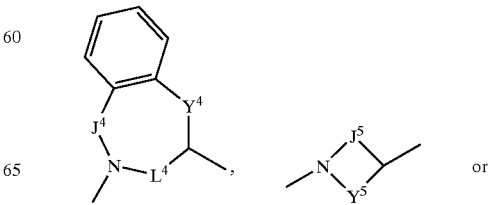

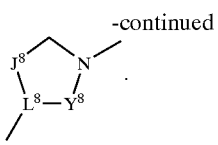

More particularly, pyrrolidine, imidazolidine, pyrazolidine, piperidine, piperazine, perhydropyrimidine, perhydropyridazine, thiazolidine, indoline, isoindoline, tetrahydroquinoline, tetrahydroisoquinoline, etc. are included.

In the specification, C3–14 mono- or bi-cyclic carboring or 3–14 membered heteroring containing 1–2 of nitrogen, 1 of oxygen, and/or 1 of sulfur, i.e. CycD is, for example, a ring represented by

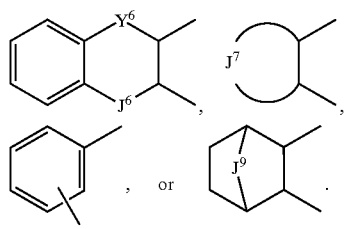

More particularly, cyclopentane, cyclohexane, cycloheptane, benzene, indan, tetrahydronaphthalene, oxorane, oxane, thiorane, thian, pyrrolidine, piperidine, bicyclo[2.2.1]heptane, bicyclo[2.2.2]octane, 7-azabicyclo[2.2.1]heptane, 7-oxobicyclo[2.2.1]heptane, 7-thiabicyclo[2.2.1]heptane, etc. are included.

In the specification, 4–18 membered heteroring containing 1–2 of nitrogen, 1 of oxygen and/or 1 of —S(O)$_p$—, i.e. CycE is, for example, a ring represented by

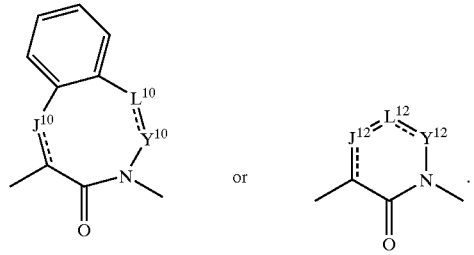

More particularly, 2-oxopyrrolidine, 2-oxopiperidine, 2-oxoperhydroazepine, 2-oxopiperazine, 3-oxomorpholine, 1,1,-dioxo-3-isothiazolidine, 1,1-dioxo-3-isothiazine, 4-oxodiazepine, 2-oxoindoline, 2-oxo-tetrahydroquinoline, 1,1-dioxo-3-benzisothiazolidine, 1,1-dioxo-3-benzisothiazine, etc. are included.

In the present invention, a 5–8 membered heteroring which contains 2 of nitrogen, i.e. CycF is, for example, a ring represented by

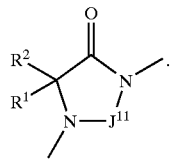

More particularly, 2,4-dioxoimidazolidine, 2-oxopiperazine, 2-oxoperhydrodiazepine substituted by $R^1$ and $R^2$ are included.

In the present invention, as may be easily understood by those skilled in the art, the symbol:

indicates that the substituent attached thereto is in front of the sheet (β-position) unless specified,

indicates that the substituent attached thereto is behind the sheet (α-position) unless specified, and

indicates that the substituent attached thereto is in β-position or α-position or a mixture thereof.

In the formula (I), any group represented by R is preferable, but more preferably, R is
(i) hydrogen,
(ii) C1–8 alkyl,
(iii) CycA,
(iv) C1–8 alkyl substituted with a group selected from CycA or nitro, (v) 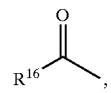

(vi) 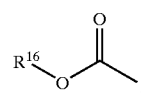

(vii) 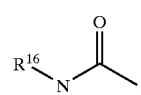

(viii) 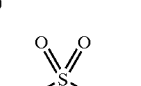, or (ix) 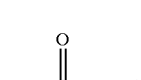

and particularly preferably, C1–8 alkyl or C1–8 alkyl substituted with a group selected from CycA or nitro,

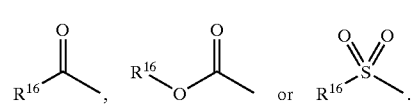

Any group represented by $R^{16}$ is preferable, but more preferably $R^{16}$ is
[I] (1) C1–8 alkyl,
(2) C2–8 alkenyl,
(3) C2–8 alkynyl,
(4) CycA, or (5) C1–8 alkyl substituted with a group selected from CycA or —NHC(O)—CycA,
(6) C2–8 alkenyl substituted with CycA or
(7) C2–8 alkynyl substituted with CycA,
wherein CycA may be substituted with 1–5 of $R^{27a}$,
$R^{27a}$ is (1) C1–8 alkyl,
(2) halogen,
(3) —$NR^{11}R^{12}$,
(4) —$OR^{13}$,
(5) phenyl,
(6) nitro,
(7) $CF_3$,
(8) cyano,
(9) tetrazole,
(10) —$SR^{14}$,
(11) —$COR^{15}$,
(12) oxo or
(13) C1–8 alkyl substituted with 1–5 of group selected from the following (a)–(k):
(a) halogen, (b) —$NR^{11}R^{12}$, (c) —$OR^{13}$, (d) phenyl, (e) nitro, (f) $CF_3$, (g) cyano, (h) tetrazole, (j) —$SR^{14}$, (k) —$COR^{15}$ or
[II] (a) C1–8 alkyl, C2–8 alkenyl or C2–8 alkynyl substituted with a group selected from halogen, $CF_3$, nitro, cyano and $NR^{18}R^{19}$ or
(b) (1) CycA containing 1–5 of substituent $R^{27}$ or
(2) C1–8 alkyl, C2–8 alkenyl or C2–8 alkynyl substituted with CycA, which contains 1–5 of substituent $R^{27}$,
wherein at least one of $R^{27}$ described in (1) and (2) is, selected from
(i) a C5–10 mono- or bi-cyclic carboring,
(ii) a 5–10 membered mono- or bi-cyclic heteroring,
(iii) —$SO_2R^{15}$, (iv) —$OCF_3$ or
(v) C1–8 alkyl substituted with 1–5 of the group selected from (a) halogen, (b) —$NR^{11}R^{12}$, (c) —$OR^{13}$, (d) a C5–10 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (l) —$SO_2R^{15}$ and (m) —$OCF_3$ (at least one is selected from a C5–10 mono- or bi-cyclic carboring, a 5–10 mono- or bi-cyclic heteroring, —$SO_2R^{15}$ or —$OCF_3$).

Particularly preferably, $R^{16}$ is
[I] (1) C1–8 alkyl,
(2) C2–8 alkenyl,
(3) C2–8 alkynyl,
(4) CycA or
(5) C1–8 alkyl substituted with a group selected from CycA or —NHC(O)—CycA,
(6) C2–8 alkenyl substituted with CycA or
(7) C2–8 alkynyl substituted with CycA,
wherein CycA is a C5–10 mono- or bi-cyclic carboaryl which may be substituted with 1–5 of $R^{27}$ or partially or completely saturated one thereof, or a 5–10 membered mono- or bi-cyclic heteroaryl containing 1–2 of nitrogen, 1–2 of oxygen and/or 1 of sulfur or partially or completely saturated one thereof or
[III] (a) C1–8 alkyl, C2–8 alkenyl or C2–8 alkynyl substituted with a group selected from halogen, $CF_3$, nitro, cyano or $NR^{18}R^{19}$, or
(b) (1) CycA which contains 1–5 of substituent $R^{27}$ or
(2) C1–8 alkyl, C2–8 alkenyl or C2–8 alkynyl substituted with CycA, which contains 1–5 of substituent $R^{27}$,
wherein at least one of $R^{27}$ described in (1) and (2) is selected from (i) a C5–10 mono- or bi-cyclic carboring,
(ii) a 5–10 membered mono- or bi-cyclic heteroring,
(iii) —$SO_2R^{15}$, (iv) —$OCF_3$ or
(v) C1–8 alkyl substituted with 1–5 of group selected from (a) halogen, (b) —$NR^{11}R^{12}$, (c) —$OR^{13}$, (d) a C5–10 mono- or bi-cyclic carboring, (e) nitro, (f) $CF_3$, (g) cyano, (h) a 5–10 membered mono- or bi-cyclic heteroring, (j) —$SR^{14}$, (k) —$COR^{15}$, (l) —$SO_2R^{15}$ and (m) $OCF_3$, wherein at least one is selected from a C5–10 mono- or bi-cyclic carboring, a 5–10 membered mono- or bi-cyclic heteroring, —$SO_2R^{15}$ or $OCF_3$,
above CycA is mono- or bi-cyclic C5–10 carboaryl or partially or completely saturated one thereof, or a 5–10 membered mono- or bi-cyclic heteroaryl containing 1–2 of nitrogen, 1–2 of oxygen and/or 1 of sulfur or partially or completely saturated one thereof.

Particularly preferably, $R^{16}$ is [I] (1) C1–4 alkyl, (2) C2–4 alkenyl, (3) C2–4 alkynyl, (4) CycA or (5) C1–4 alkyl, C2–4 alkenyl or C2–4 alkynyl substituted with CycA, wherein CycA is cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, tetrahydroquinoxaline, optionally substituted with 1–5 of $R^{27a}$ or
[II] (a) C1–8 alkyl, C2–8 alkenyl or C2–8 alkynyl substituted with a group selected from halogen, $CF_3$, nitro, cyano or $NR^{18}R^{19}$ or
(b) (1) CycA which contains 1–5 of substituent $R^{27}$, or
(2) C1–8 alkyl, C2–8 alkenyl or C2–8 alkynyl substituted with CycA which contains 1–5 of substituent $R^{27}$,
wherein at least one of $R^{27}$ described in (1) and (2) is selected from
(i) a C5–10 mono- or bi-cyclic carboring,
(ii) a 5–10 membered mono- or bi-cyclic heteroring,
(iii) —$SO_2R^{15}$, (iv) —$OCF_3$, or
(v) C1–8 alkyl substituted with 1–5 of group selected from (a) halogen, (b) —$NR^{11}R^{12}$, (c) —$OR^{13}$, (d) C5–10 mono- or bi-cyclic carboring, (e) nitro, (f) $CF_3$, (g) cyano, (h) 5–10 membered mono- or bi-cyclic heteroring, (j) —$SR^{14}$, (k) —$COR^{15}$, (l) —$SO_2R^{15}$ and (m) —$OCF_3$, wherein at least one is a group selected from a C5–10 mono- or bi-cyclic carboring, a 5–10 membered mono- or bi-cyclic heteroring, —$SO_2R^{15}$ or —$OCF_3$, CycA is particularly preferably, cyclopentane, cyclohexane, benzene, naphthalene, pyrrolidine, piperidine, piperazine, morpholine, pyrrole, furan, thiophene, pyridine, pyrimidine, pyrazine, pyridazine, indole, isoindole, quinoline, isoquinoline, quinazoline, quinoxaline, phthalazine, benzothiophene, benzofuran, benzoxadiazole, tetrahydroquinoline, tetrahydroquinazoline, or tetrahydroquinoxaline.

In the formula (I), any one of a single bond,

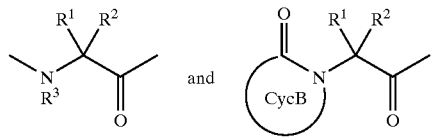

(which is formed with R) is preferable as $AA^1$, but more preferably, $AA^1$ is a single bond or

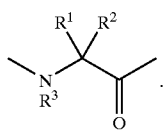

Any group represented by $R^1$ is preferable, but more preferably $R^1$ is hydrogen, C1–8 alkyl, phenyl or C1–8 alkyl substituted with $NH_2$, C1–4 alkoxy, SH, $SCH_3$, phenyl, hydroxyphenyl, COOH, $CONH_2$, guanidino, imidazole or indole.

Particularly preferably, $R^1$ is hydrogen, C1–8 alkyl, phenyl or C1–8 alkyl substituted with C1–4 alkoxy or phenyl. Then, Any group represented by $R^2$ is preferable, but hydrogen is particularly preferable.

And C3–6 alkylene which $R^1$ and $R^2$ together form is also preferable.

Any group represented by $R^3$ is preferable, but more preferably $R^3$ is hydrogen or C1–4 alkyl.

And C2–4 alkylene which $R^3$ and $R^1$ together form is also preferable.

$AA^2$ is a single bond, In the formula (I), Any group represented by $AA^2$ is preferable, but more preferably,

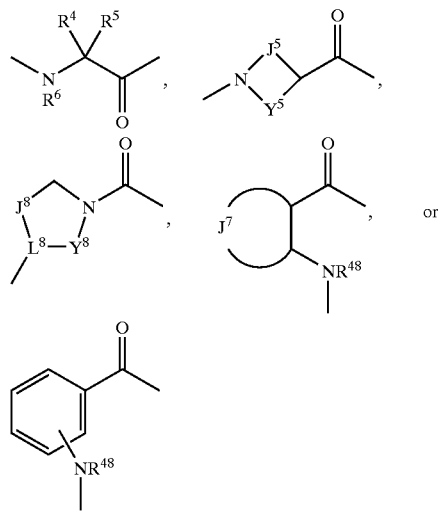

and particularly preferably $AA^2$ is a single bond,

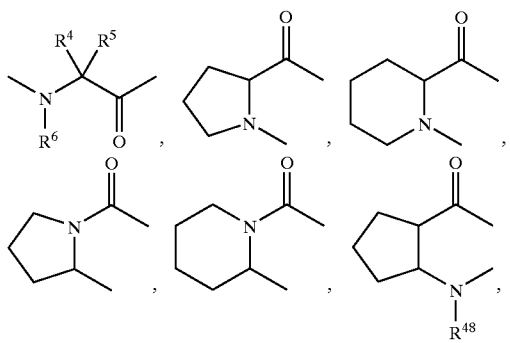

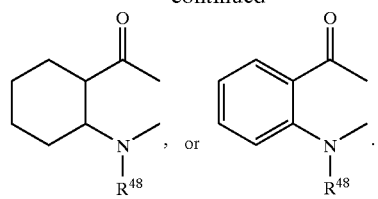

Any group represented by $R^4$ is preferable, but more preferably $R^4$ is hydrogen, C1–8 alkyl, phenyl or C1–8 alkyl substituted with $NH_2$, C1–4 alkoxy, SH, $SCH_3$, phenyl, hydroxyphenyl, COOH, $CONH_2$, guanidino, imidazole or indole.

Particularly preferably, $R^4$ is hydrogen, C1–8 alkyl, phenyl or C1–8 alkyl substituted with C1–4 alkoxy or phenyl. Then, all groups f or $R^5$ are preferable, but hydrogen is particularly preferable.

And C3–6 alkylene which $R^4$ and $R^5$ together form is also preferable.

$R^6$ is all preferable, but more preferably $R^6$ is hydrogen or C1–4 alkyl.

And C2–4 alkylene which $R^6$ and $R^4$ together form is also preferable.

Any group represented by $R^{48}$ is preferable, but more preferably,

[I] hydrogen, C1–4 alkyl, phenyl or C1–4 alkyl substituted with phenyl, or

[II] C2–6 alkylene wherein one carbon atom may be replaced by oxygen, sulfur or —$NR^{47}$—, wherein $R^{47}$ is hydrogen or C1–4 alkyl, to be formed taken together with R, when $AA^1$ is a single bond.

Particularly preferable groups for $R^{48}$ are [I] hydrogen atom or C1–4 alkyl, or

[II] when $AA^1$ is a single bond, taken together with R to form tetramethylene, pentamethylene, —$CH_2$—$CH_2$—O—$CH_2$—$CH_2$—, —$CH_2$—$CH_2$—NH—$CH_2$—$CH_2$— or —$CH_2$—$CH_2$—N($CH_3$)—$CH_2$—$CH_2$—.

In the formula (I), the groups which $AA^1$ and $AA^2$ together form are all preferable, but more preferably, it is (i)

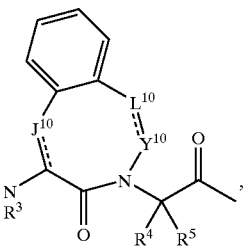

(ii)

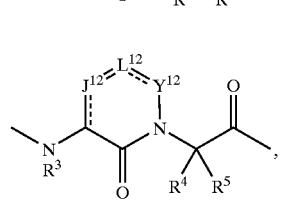, or

-continued (iii)
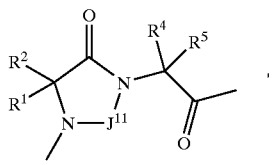

and particularly preferably,

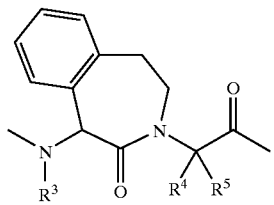

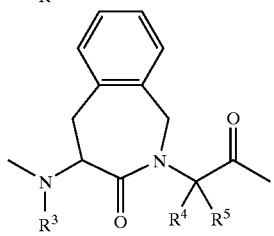

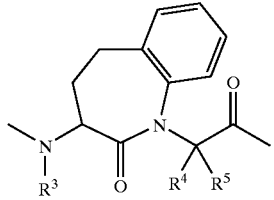

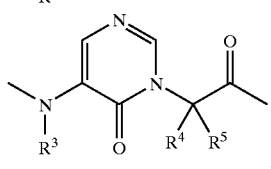

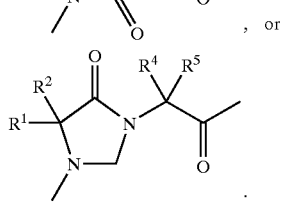
, or

Any group represented by $R^7$ is preferable, but more preferably, $R^7$ is C1–8 alkyl, phenyl, or C1–8 alkyl substituted with $NH_2$, C1–4 alkoxy, SH, $SCH_3$, phenyl, hydroxyphenyl, COOH, $CONH_2$, guanidino, imidazole or indole.

Particularly preferably, $R^7$ is hydrogen, C1–8 alkyl, phenyl, or C1–8 alkyl substituted with C1–4 alkoxy or phenyl. Then, Any group represented by $R^8$ is preferable, but hydrogen atom is most preferable.

And C3–6 alkylene which $R^7$ and $R^8$ together form is also preferable.

$R^9$ is all preferable, but more preferably $R^9$ is hydrogen or C1–4 alkyl.

And C2–4 alkylene which $R^9$ and $R^7$ together form is also preferable.

In the present invention, the following compounds are preferred;

the compound of formula (Ia)

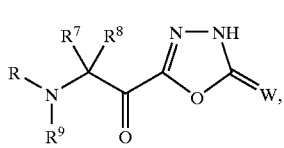

(Ia)

wherein all symbols are the same meanings as above, the compound of formula (Ib)

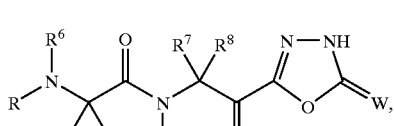

(Ib)

wherein all symbols are the same meanings as above, the compound of formula (Ic)

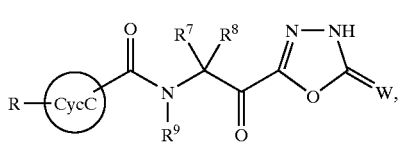

(Ic)

wherein all symbols are the same meanings as above, the compound of formula (Id)

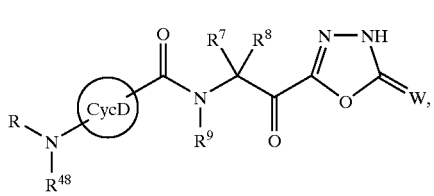

(Id)

wherein all symbols are the same meanings as above, the compound of formula (Ie)

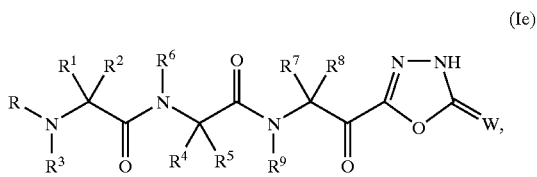

(Ie)

wherein all symbols are the same meanings as above, the compound of formula (If)

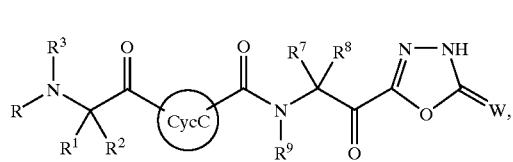

(If)

wherein all symbols are the same meanings as above, the compound of formula (Ig)

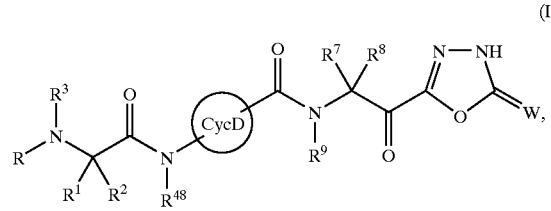

(Ig)

wherein all symbols are the same meanings as above, the compound of formula (Ih)

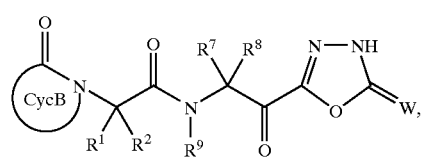

(Ih)

wherein all symbols are the same meanings as above, the compound of formula (Ii)

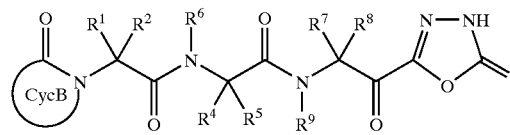

(Ii)

wherein all symbols are the same meanings as above, the compound of formula (Ij)

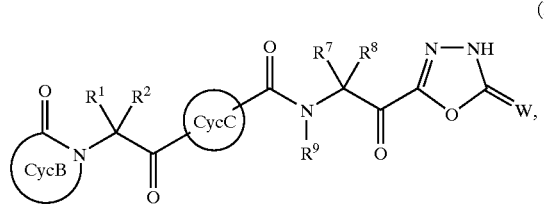

(Ij)

wherein all symbols are the same meanings as above, the compound of formula (Ik)

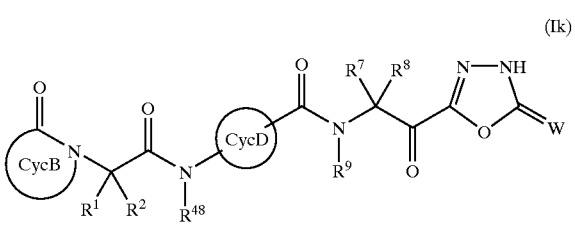

(Ik)

wherein all symbols are the same meanings as above, the compound of formula (Im)

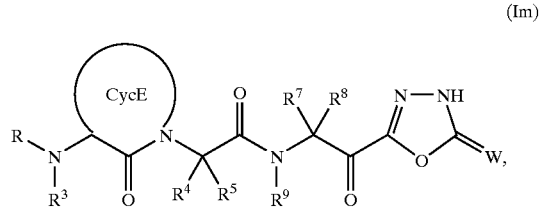

(Im)

wherein all symbols are the same meanings as above, the compound of formula (In)

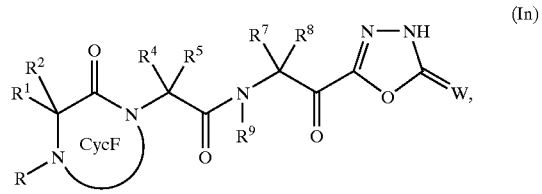

(In)

wherein all symbols are the same meanings as above, and non-toxic salts thereof.

Particularly, the compounds of the examples described hereinafter, the compounds in the following tables 1~8 and non-toxic salts thereof are preferable.

In the following tables, the number placed before the substituents means the position of the substituent in a benzene ring.

TABLE 1-1

(I-1A)

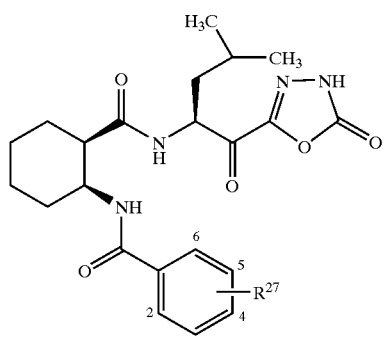

| No. | $R^{27}$ |
|-----|----------|
| 1   | 2-F      |
| 2   | 3-F      |
| 3   | 4-F      |
| 4   | 2-CN     |

TABLE 1-1-continued
(I-1A)
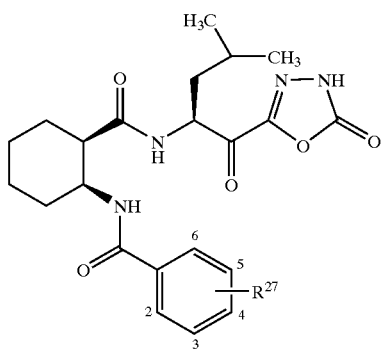
| No. | R²⁷ |
|---|---|
| 5 | 3-CN |
| 6 | 4-CN |
| 7 | 3-NO₂ |
| 8 | 4-NO₂ |
| 9 | 3-CH₃ |
| 10 | 4-CH₃ |
| 11 | 2-CH₂—Cl |
| 12 | 4-CH₂—Cl |
| 13 | 4-Cl |
| 14 | 4-CF₃ |
| 15 | 4-CH₂CH₃ |
| 16 | 4-(CH₂)₃CH₃ |
| 17 | 4-C(CH₃)₃ |
| 18 | 4-N(CH₃)₂ |
| 19 | 4-OCH₃ |
| 20 | 4-OCH₂CH₃ |
| 21 | 4-Phenyl |
| 22 | 2,3-di-CH₃ |
| 23 | 3,5-di-F |
| 24 | 3,4-di-F |
TABLE 1-2
(I-1A)
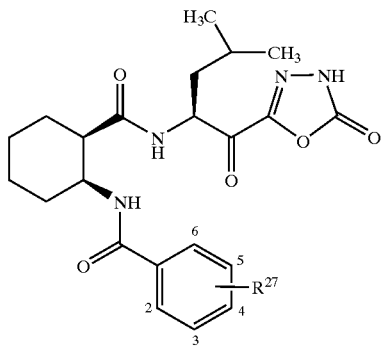
| No. | R²⁷ |
|---|---|
| 25 | 2-CH₂—N(CH₃)₂ |
| 26 | 3-CH₂—N(CH₃)₂ |
| 27 | 4-CH₂—N(CH₃)₂ |
| 28 |  |
TABLE 1-2-continued
(I-1A)
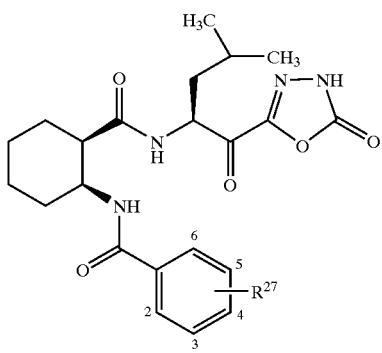
| No. | R²⁷ |
|---|---|
| 29 | 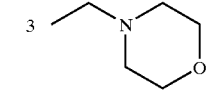 |
| 30 | 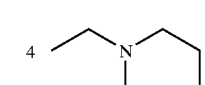 |
| 31 | 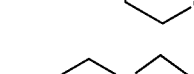 |
| 32 |  |
| 33 | 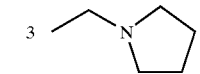 |
TABLE 2
(I-2A)
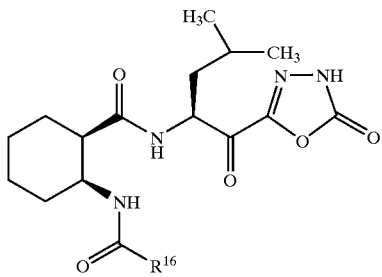
| No. | R¹⁶ |
|---|---|
| 1 |  |
| 2 |  |

TABLE 2-continued
(I-2A)
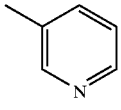
| No. | R¹⁶ |
|---|---|
| 3 | 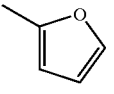 |
| 4 | 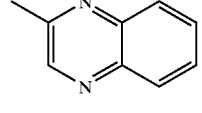 |
| 5 | 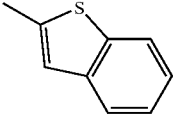 |
| 6 | 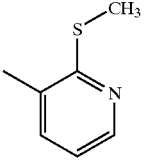 |
| 7 | 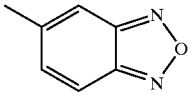 |
| 8 | 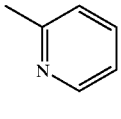 |
| 9 | 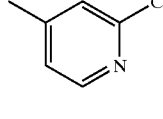 |
| 10 | 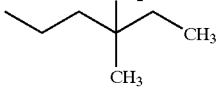 |
| 11 | 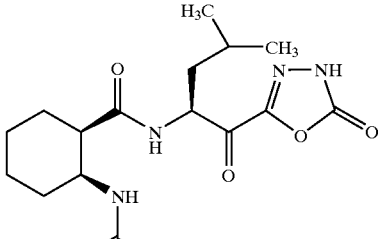 |
TABLE 2-continued
(I-2A)
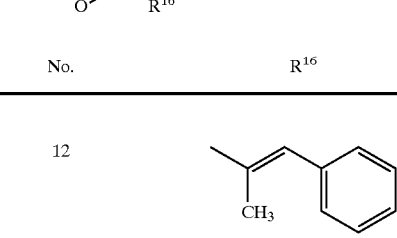
| No. | R¹⁶ |
|---|---|
| 12 | 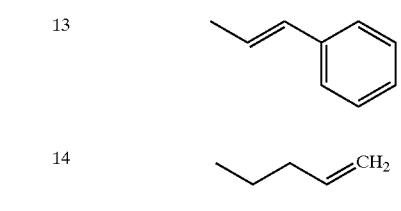 |
| 13 | 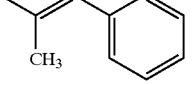 |
| 14 | 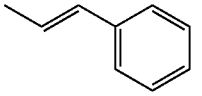 |
| 15 | 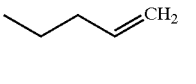 |
| 16 |  |
| 17 | 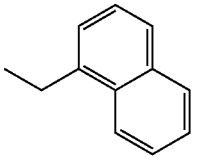 |
| 18 | 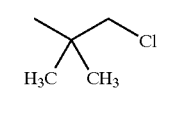 |
| 19 | 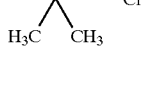 |
| 20 | 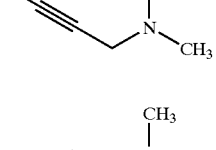 |
| 21 | 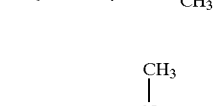 |

TABLE 3

(I-3A)

| No. | —ᵦAA²ₐ— |
|-----|---------|
| 1 | (1,2-disubstituted cyclohexane: C(=O)ₐ and NHₐ, trans) |
| 2 | (1,2-disubstituted cyclohexane: C(=O)ₐ and NHᵦ, cis) |
| 3 | 1-(3-phenylpropyl)-2-acyl-3-amino piperidine |
| 4 | 1-(3-phenylpropyl)-2-acyl-3-amino piperidine (stereoisomer) |
| 5 | 1-acyl-2-methyl hexahydropyridazine |
| 6 | 1-acyl-2-methyl-6-oxo hexahydropyridazine |
| 7 | 3-acyl-N-methyl thiazolidine |
| 8 | 3-acyl-N-methyl thiazolidine (stereoisomer) |
| 9 | 4-benzyloxy-1-methyl-2-acyl pyrrolidine |
| 10 | 4-benzyloxy-1-methyl-2-acyl pyrrolidine (stereoisomer) |
| 11 | 2-acyl-3-(methylamino) norbornane |
| 12 | 2-methyl-3-acyl-1,2,3,4-tetrahydroisoquinoline |

TABLE 3-continued (I-3A)

| No. | —ᵇAA²ₐ— |
|---|---|
| 13 | (bicyclic ketone-amine, acetyl position a, NH position b) |
| 14 | (7-oxabicyclic ketone-amine, acetyl a, NH b) |
| 15 | (7-oxabicyclic ketone-amine alternate stereochemistry, acetyl a, NH b) |
| 16 | (hexahydropyridazine, acetyl a, NH position b) |
| 17 | (N-methyl hexahydropyridazine, acetyl a, N-CH₃ position b) |

TABLE 4

(I-4A)

| No. | R⁷ |
|---|---|
| 1 | —CH₂CH(CH₃)CH₃ (sec-butyl-like, CH₃/CH₃) |
| 2 | —CH₂CH(CH₃)₂ (isobutyl) |
| 3 | —CH₂COOH |
| 4 | —CH₂C(O)NH₂ |
| 5 | —CH₂OCH₂CH₃ |
| 6 | —CH₂CH₂OCH₃ |
| 7 | —CH₂-(4-fluorophenyl) |
| 8 | —CH₂-(4-pyridyl) |
| 9 | —CH₂CH₂CH₂NHC(=NH)NH₂ |
| 10 | —CH₂CH₂COOH |

TABLE 4-continued (I-4A)

| No. | R⁷ |
|---|---|
| 11 | H₂N-C(=O)-CH₂CH₂- |
| 12 | benzyl |
| 13 | CH₃- (with wedge) |
| 14 | H₃C-CH(CH₃)-CH₂- (sec-butyl) |
| 15 | H- |
| 16 | HO-CH(CH₃)- |
| 17 | Phenyl |
| 18 | HOCH₂- |
| 19 | 4-HO-C₆H₄-CH₂- |
| 20 | H₂N-(CH₂)₄- |
| 21 | (1H-imidazol-4-yl)methyl |

TABLE 4-continued (I-4A)

| No. | R⁷ |
|---|---|
| 22 | CH₃SO₂NH-C(=O)-CH₂- |

TABLE 5-1

(I-5A)

| No. | R²⁷ |
|---|---|
| 1 | 2-F |
| 2 | 3-F |
| 3 | 4-F |
| 4 | 2-CN |
| 5 | 3-CN |
| 6 | 4-CN |
| 7 | 3-NO₂ |
| 8 | 4-NO₂ |
| 9 | 3-CH₃ |
| 10 | 4-CH₃ |
| 11 | 2-CH₂—Cl |
| 12 | 4-CH₂—Cl |
| 13 | 4-Cl |
| 15 | 4-CH₂CH₃ |
| 16 | 4-(CH₂)₃CH₃ |
| 17 | 4-C(CH₃)₃ |
| 18 | 4-N(CH₃)₂ |
| 19 | 4-OCH₃ |
| 20 | 4-OCH₂CH₃ |
| 21 | 4-Phenyl |
| 22 | 2,3-di-CH₃ |
| 23 | 3,5-di-F |
| 24 | 3,4-di-F |

TABLE 5-2

(I-5A)

| No. | $R^{27}$ |
|---|---|
| 25 | 2-$CH_2$—$N(CH_3)_2$ |
| 26 | 3-$CH_2$—$N(CH_3)_2$ |
| 27 | 4-$CH_2$—$N(CH_3)_2$ |
| 28 | 2-CH₂-morpholine |
| 29 | 3-CH₂-morpholine |
| 30 | 4-CH₂-morpholine |
| 31 | 2-CH₂-pyrrolidine |
| 32 | 3-CH₂-pyrrolidine |
| 33 | 4-CH₂-pyrrolidine |

TABLE 6

(I-6A)

| No. | $R^{16}$ |
|---|---|
| 1 | methylnaphthalene |
| 2 | 5-methyl-2-chloropyridine |

TABLE 6-continued (I-6A)

| No. | $R^{16}$ |
|---|---|
| 3 | 3-methylpyridine |
| 4 | 2-methylfuran |
| 5 | methylquinoxaline |
| 6 | 2-methylbenzothiophene |
| 7 | 3-methyl-2-(methylthio)pyridine |
| 8 | methylbenzofurazan |
| 9 | 2-methylpyridine |
| 10 | 4-methyl-2-chloropyridine |
| 11 | 3-nitro-3-methylhexane |
| 12 | 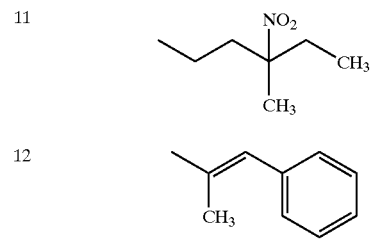 |

TABLE 6-continued
(I-6A)
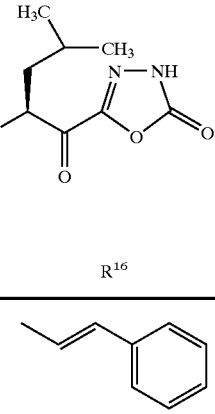
| No. | R16 |
|-----|-----|
| 13 | 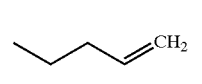 |
| 14 | 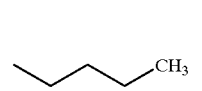 |
| 15 | 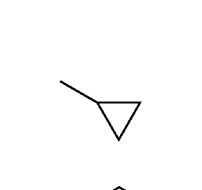 |
| 16 | 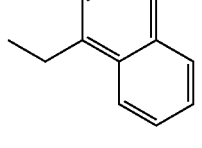 |
| 17 | 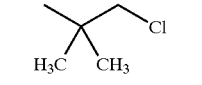 |
| 18 | 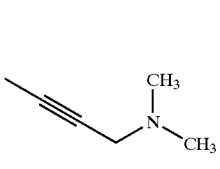 |
| 19 | 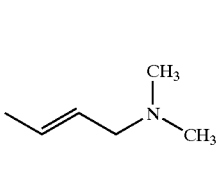 |
| 20 | 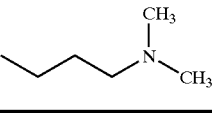 |
| 21 | 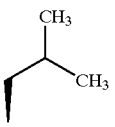 |
TABLE 7
(I-7A)
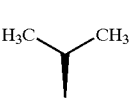
| No. | R7 |
|-----|-----|
| 1 |  |
| 2 | 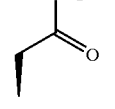 |
| 3 | 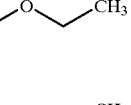 |
| 4 | 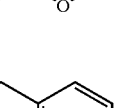 |
| 5 | 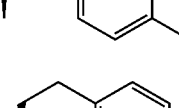 |
| 6 | 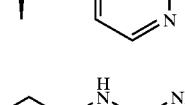 |
| 7 |  |
| 8 | 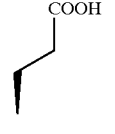 |
| 9 | 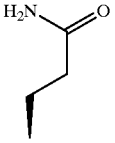 |
| 10 | COOH |
| 11 | H2N—C(=O)— |

TABLE 7-continued
(I-7A)
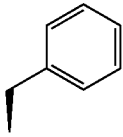
| No. | R⁷ |
|---|---|
| 12 |  |
| 13 | 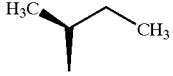 |
| 14 |  |
| 15 |  |
| 16 |  |
| 17 | Phenyl |
| 18 |  |
| 19 | 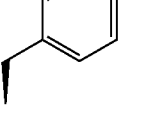 |
| 20 |  |
| 21 | 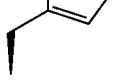 |
| 22 | 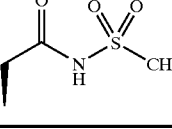 |
TABLE 8
(I-8A)
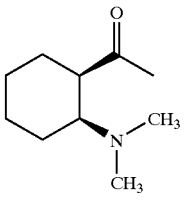
| No. | R—AA¹—AA²— |
|---|---|
| 1 | 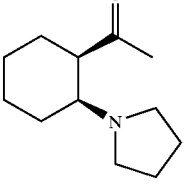 |
| 2 | 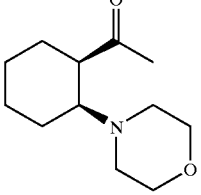 |
| 3 | 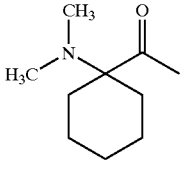 |
| 4 | 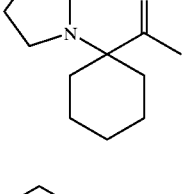 |
| 5 | 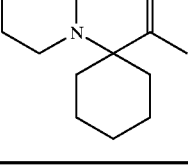 |
| 6 |  |

TABLE 9-1
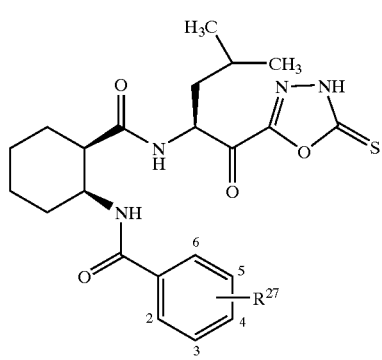
(I-1B)
| No. | R²⁷ |
|---|---|
| 1 | 2-F |
| 2 | 3-F |
| 3 | 4-F |
| 4 | 2-CN |
| 5 | 3-CN |
| 6 | 4-CN |
| 7 | 3-NO₂ |
| 8 | 4-NO₂ |
| 9 | 3-CH₃ |
| 10 | 4-CH₃ |
| 11 | 2-CH₂—Cl |
| 12 | 4-CH₂—Cl |
| 13 | 4-Cl |
| 14 | 4-CF₃ |
| 15 | 4-CH₂CH₃ |
| 16 | 4-(CH₂)₃CH₃ |
| 17 | 4-C(CH₃)₃ |
| 18 | 4-N(CH₃)₂ |
| 19 | 4-OCH₃ |
| 20 | 4-OCH₂CH₃ |
| 21 | 4-Phenyl |
| 22 | 2,3-di-CH₃ |
| 23 | 3,5-di-F |
| 24 | 3,4-di-F |
TABLE 9-2
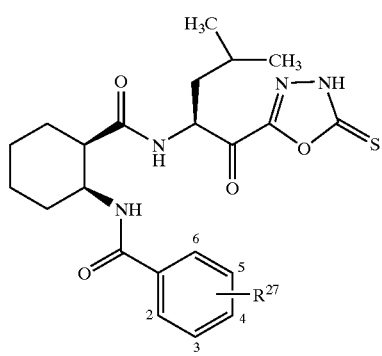
(I-1B)
| No. | R²⁷ |
|---|---|
| 25 | 2-CH₂—N(CH₃)₂ |
| 26 | 3-CH₂—N(CH₃)₂ |
| 27 | 4-CH₂—N(CH₃)₂ |
TABLE 9-2-continued
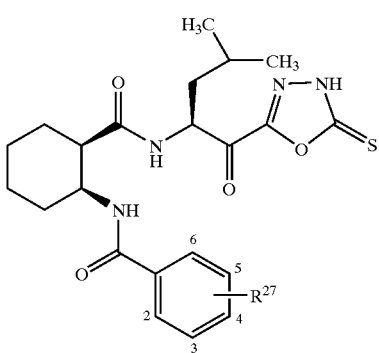
(I-1B)
| No. | R²⁷ |
|---|---|
| 28 | 2-(4-ethylmorpholine) |
| 29 | 3-(4-ethylmorpholine) |
| 30 | 4-(4-ethylmorpholine) |
| 31 | 2-(1-ethylpyrrolidine) |
| 32 | 3-(1-ethylpyrrolidine) |
| 33 | 4-(1-ethylpyrrolidine) |
TABLE 10
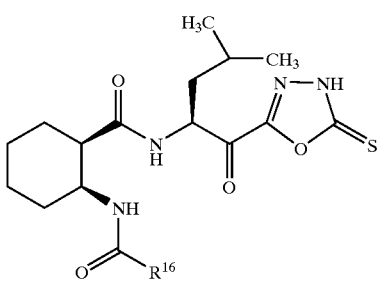
(I-2B)
| No. | R¹⁶ |
|---|---|
| 1 | 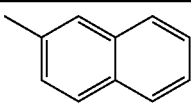 |

TABLE 10-continued
(I-2B)
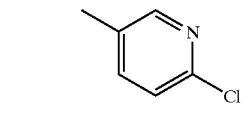
| No. | R16 |
|---|---|
| 2 | 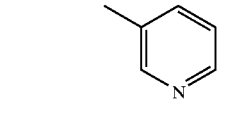 |
| 3 | 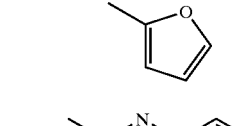 |
| 4 | 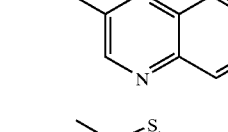 |
| 5 | 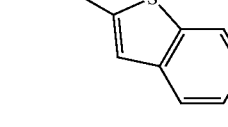 |
| 6 | 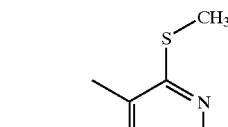 |
| 7 | 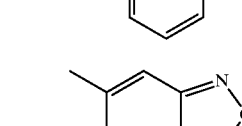 |
| 8 | 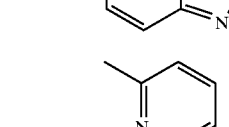 |
| 9 | 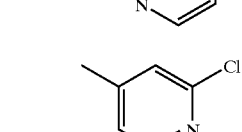 |
| 10 | 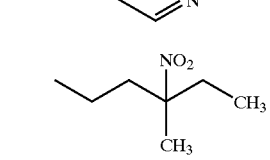 |
| 11 | 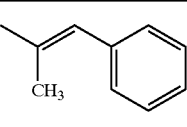 |
TABLE 10-continued
(I-2B)
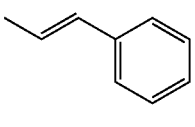
| No. | R16 |
|---|---|
| 12 | 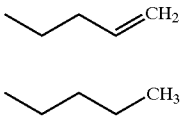 |
| 13 | 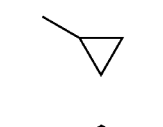 |
| 14 | 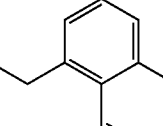 |
| 15 | 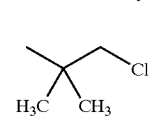 |
| 16 | 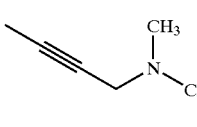 |
| 17 | 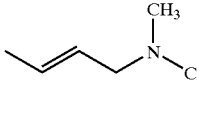 |
| 18 | 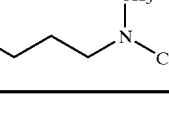 |
| 19 |  |
| 20 | |
| 21 | |

TABLE 11
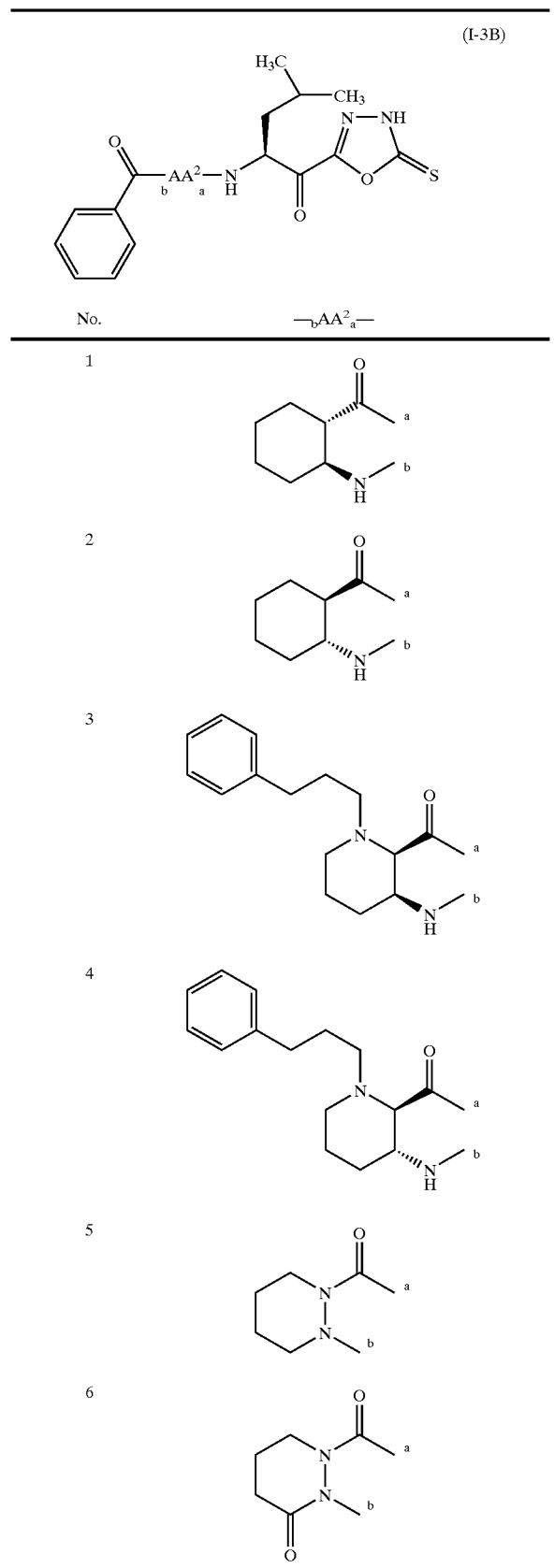
TABLE 11-continued
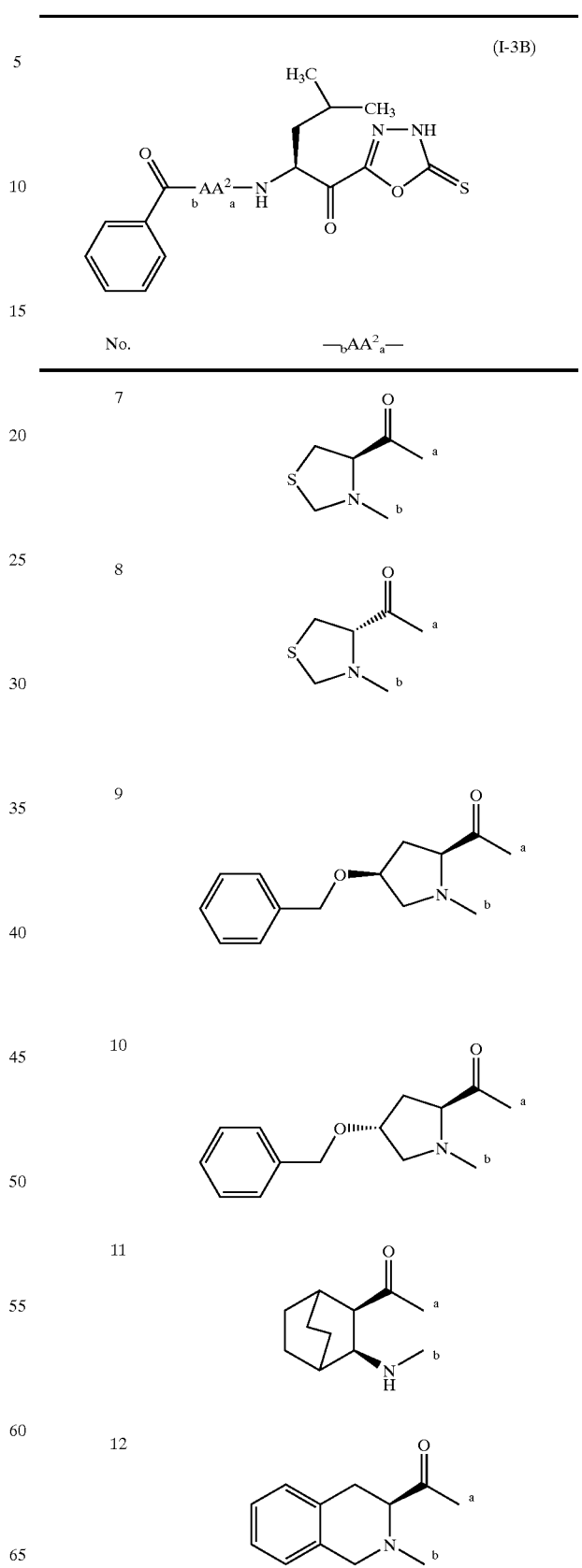

TABLE 11-continued (I-3B)

| No. | —ᵦAA²ₐ— |
|-----|---------|
| 13  | (bicyclo[2.2.1]heptane with acetyl and NH) |
| 14  | (7-oxabicyclo[2.2.1]heptane with acetyl and NH) |
| 15  | (oxabicyclic with acetyl and NH) |
| 16  | (hexahydropyridazine with acetyl, NH-methyl) |
| 17  | (hexahydropyridazine with acetyl, N-methyl, N-methyl) |

TABLE 12

(I-4B)

| No. | R⁷ |
|-----|-----|
| 1 | $CH(CH_3)CH_2CH_3$ (sec-butyl) |
| 2 | $CH_2CH(CH_3)_2$ (isobutyl) |
| 3 | $CH_2CH_2COOH$ |
| 4 | $CH_2C(O)NH_2$ |
| 5 | $CH_2OCH_2CH_3$ |
| 6 | $CH_2CH_2OCH_3$ |
| 7 | $CH_2$-(4-fluorophenyl) |
| 8 | $CH_2$-(4-pyridyl) |
| 9 | $CH_2CH_2CH_2NHC(=NH)NH_2$ |
| 10 | $CH_2CH_2COOH$ |

TABLE 12-continued (I-4B)

[Structure: cyclohexane with C(=O)NH-CH(R7)-C(=O)- linked to 2-thioxo-1,3,4-oxadiazole, and NH-C(=O)-phenyl substituent]

| No. | R⁷ |
|---|---|
| 11 | H₂N-C(=O)-CH₂-CH₂- |
| 12 | -CH₂-phenyl |
| 13 | -CH₃ |
| 14 | H₃C-CH(CH₃)-CH₂- (sec-butyl) |
| 15 | H |
| 16 | HO-CH(CH₃)- |
| 17 | Phenyl |
| 18 | HO-CH₂- |
| 19 | 4-HO-C₆H₄-CH₂- |
| 20 | H₂N-(CH₂)₄- |
| 21 | (1H-imidazol-4-yl)methyl |
| 22 | CH₃-S(=O)₂-NH-C(=O)-CH₂- |

TABLE 13-1

(I-5B)

[Structure: R²⁷-substituted phenyl-C(=O)-NH-C(cyclohexyl)-C(=O)-NH-CH(CH₂CH(CH₃)₂)-C(=O)- linked to 2-thioxo-1,3,4-oxadiazole]

| No. | R²⁷ |
|---|---|
| 1 | 2-F |
| 2 | 3-F |
| 3 | 4-F |
| 4 | 2-CN |
| 5 | 3-CN |
| 6 | 4-CN |
| 7 | 3-NO₂ |
| 8 | 4-NO₂ |
| 9 | 3-CH₃ |
| 10 | 4-CH₃ |
| 11 | 2-CH₂—Cl |
| 12 | 4-CH₂—Cl |
| 13 | 4-Cl |
| 14 | 4-CF₃ |
| 15 | 4-CH₂CH₃ |
| 16 | 4-(CH₂)₃CH₃ |
| 17 | 4-C(CH₃)₃ |
| 18 | 4-N(CH₃)₂ |
| 19 | 4-OCH₃ |
| 20 | 4-OCH₂CH₃ |
| 21 | 4-Phenyl |
| 22 | 2,3-di-CH₃ |
| 23 | 3,5-di-F |
| 24 | 3,4-di-F |

TABLE 13-2

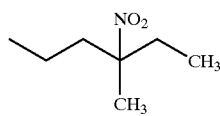

(I-5B)

| No. | R²⁷ |
|---|---|
| 25 | 2-CH₂—N(CH₃)₂ |
| 26 | 3-CH₂—N(CH₃)₂ |
| 27 | 4-CH₂—N(CH₃)₂ |
| 28 | 2-CH₂-morpholine |
| 29 | 3-CH₂-morpholine |
| 30 | 4-CH₂-morpholine |
| 31 | 2-CH₂-pyrrolidine |
| 32 | 3-CH₂-pyrrolidine |
| 33 | 4-CH₂-pyrrolidine |

TABLE 14

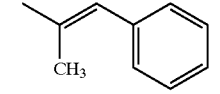

(I-6B)

| No. | R¹⁶ |
|---|---|
| 1 | 6-methyl-2-naphthyl |
| 2 | 6-chloro-3-methyl-2-pyridyl |
| 3 | 3-methyl-pyridyl |
| 4 | 5-methyl-2-furyl |
| 5 | 3-methyl-quinoxalinyl |
| 6 | 3-methyl-benzothiophenyl |
| 7 | 2-methylthio-3-methyl-pyridyl |
| 8 | 5-methyl-benzoxadiazolyl |
| 9 | 6-methyl-2-pyridyl |
| 10 | 2-chloro-4-methyl-pyridyl |
| 11 | 3-nitro-3-methyl-hexyl |
| 12 | 2-methyl-3-phenyl-propenyl |

TABLE 14-continued (I-6B)

Structure with R¹⁶ group attached via amide to cyclohexyl, connected to leucyl-thiadiazolethione.

| No. | R¹⁶ |
|---|---|
| 13 | styryl (PhCH=CH–) |
| 14 | CH₂=CH–CH₂–CH₂–CH₂– (pent-4-en-1-yl) |
| 15 | n-pentyl |
| 16 | cyclopropyl |
| 17 | 1-naphthylethyl |
| 18 | neopentyl chloride ((CH₃)₂C(CH₂Cl)CH₂–) |
| 19 | –CH₂–C≡C–CH₂–N(CH₃)₂ |
| 20 | –CH₂–CH=CH–CH₂–N(CH₃)₂ |
| 21 | –(CH₂)₄–N(CH₃)₂ |

TABLE 15

(I-7B)

Structure: benzoyl-NH-cyclohexyl-C(=O)-NH-CH(R⁷)-C(=O)-thiadiazolethione.

| No. | R⁷ |
|---|---|
| 1 | –CH₂–CH(CH₃)–CH₃ (isobutyl) |
| 2 | –CH(CH₃)–CH(CH₃)₂ |
| 3 | –CH₂–COOH |
| 4 | –CH₂–C(=O)NH₂ |
| 5 | –CH₂–O–CH₂CH₃ |
| 6 | –CH₂–CH₂–O–CH₃ |
| 7 | –CH₂–(4-fluorophenyl) |
| 8 | –CH₂–(4-pyridyl) |
| 9 | –(CH₂)₃–NH–C(=NH)–NH₂ |
| 10 | –(CH₂)₂–COOH |
| 11 | –CH₂–C(=O)NH₂ |

TABLE 15-continued (I-7B)

| No. | R⁷ |
|---|---|
| 12 | benzyl |
| 13 | methyl (CH₃) |
| 14 | sec-butyl |
| 15 | H |
| 16 | (S)-1-hydroxyethyl (HO,,,,CH₃) |
| 17 | Phenyl |
| 18 | hydroxymethyl (CH₂OH) |
| 19 | 4-hydroxybenzyl |
| 20 | 4-aminobutyl |
| 21 | (1H-imidazol-4-yl)methyl |
| 22 | N-(methylsulfonyl)propanamide derivative |

TABLE 16

(I-8B)

| No. | R—AA¹—AA²— |
|---|---|
| 1 | 2-(dimethylamino)cyclohexyl methyl ketone |
| 2 | 2-(pyrrolidin-1-yl)cyclohexyl methyl ketone |
| 3 | 2-(morpholin-4-yl)cyclohexyl methyl ketone |
| 4 | 1-(dimethylamino)cyclohexyl methyl ketone |
| 5 | 1-(pyrrolidin-1-yl)cyclohexyl methyl ketone |
| 6 | 1-(morpholin-4-yl)cyclohexyl methyl ketone |

In the present invention, all isomers are included unless specified. For example, alkyl, alkoxy, alkylthio, alkenyl, alkynyl and alkylene include straight and branched ones. Furthermore, the present invention includes isomers in double bond, ring, fused ring (E, Z, cis, trans), isomers by the presence of asymmetric carbon etc. (R, S, α, β, enantiomer, diastereomer), optical isomers having optical rotation (D, L, d, l, +, -), polars of separation by chromatography (more polar, less polar), equilibrium compound, a compound of arbitrary ratios of them and racemic mixture.

Salts

The compounds of formula (I) of the present invention may be converted into corresponding non-toxic salts by conventional methods. Non-toxic salts in this specification include alkali metal salts, alkaline earth metal salts, ammonium salts, amine salts and acid-addition salts.

Non-toxic and water-soluble salts are preferable. Appropriate salts include salts of alkali metals (potassium, sodium etc.), salts of alkaline-earth metals (calcium, magnesium etc.), ammonium salts and salts of pharmaceutically-acceptable organic amines (tetramethyl ammonium, triethylamine, methylamine, dimethylamine, cyclopentylamine, benzylamine, phenethylamine, piperidine, monoethanolamine, diethanolamine, tris (hydroxymethyl) aminomethane, lysine, arginine, N-methyl-D-glucamine etc.) and salts of alkali metals are more preferably.

Non-toxic, water-soluble acid-addition salts are preferable. Appropriate acid-addition salts are, inorganic salts such as hydrochloride, hydrobromide, sulfate, phosphate, nitrate, or organic salts such as acetate, trifluoroacetate, lactate, tartrate, oxalate, fumarate, malate, citrate, benzoate, methanesulfonate, ethanesulfonate, benzenesulfonate, toluenesulfonate, isethionate, glucuronate, gluconate. The compounds of formula (I) of the present invention or a salt thereof may be converted into a hydrate by conventional method.

The methods for the preparation of the compound of the present invention (1) Among the compound of formula (I), the compound wherein $AA^1$ and $AA^2$ represents a single bond at the same time and none of R, $R^7$ or $R^8$ contains carboxy, hydroxy, amino, thiol, or guanidino, and R does not represent hydrogen; i.e. the compound of formula (IA)

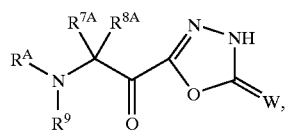

(IA)

wherein $R^A$, $R^{7A}$, and $R^{8A}$ are the same meanings as R, $R^{A7}$ and $R^8$, with proviso that none of them contains carboxy, hydroxy, amino, thiol or guanidino, and $R^A$ is not hydrogen, W is oxygen or sulfur and the other symbols are the same meanings as above, may be prepared by subjecting to oxidation reaction a compound of formula (IIA)

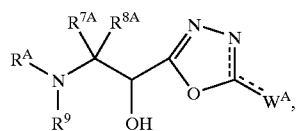

(IIA)

wherein

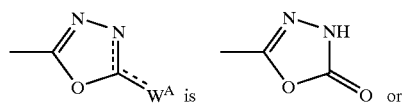

-continued

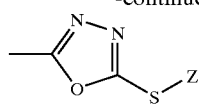

and Z is a protective group for S (e.g. 2-thienylmethyl) and the other symbols are the same meanings as above, followed by deprotection reaction when $W^A$ is —S—Z.

Oxidation reaction is known, for example, (1) a method utilizing TEMPO reagent, (2) a method utilizing Dess-Martin reagent, and etc. may be included.

To describe them concretely, (1) a method utilizing TEMPO reagent is, for example, carried out in an organic solvent (chloroform, dichloromethane, etc.), in the presence of TEMPO reagent (2,2,6,6-tetramethyl-1-piperidinyloxy, free radical) at a temperature of 20~16° C.

(2) a method utilizing Dess-Martin reagent is, for example, carried out in an organic solvent (chloroform, dichloromethane, etc.) in the presence of Dess-Martin reagent (1,1,1-triacetoxy-1,1-dihydro-1,2-benzoiodoxol-3-(1H)-one) at a temperature of 0~40° C.

These reactions of (1) and (2) are desirably carried out under the atmosphere of an inert gas (argon, nitrogen, etc.) under anhydrous conditions.

The present invention further includes other oxidation reactions which oxidizes alcohol to ketone easily and selectively. For example, Jones oxidation, oxidation by pyridinium chlorochromate (PCC), or ones described in "Comprehensive Organic Transformations", Richard C. Larock, VCH Publishers, Inc., (1989) 604–614, may be used.

Deprotection reaction is known, for example, it is carried out in organic solvent (ethyl acetate, etc.) using acid (hydrochloric acid, sulfuric acid, etc.) at a temperature between 0 and 100° C.

(2) Among the compound of formula (I), the compound wherein $AA^1$ and $AA^2$ are a single bond at the same time and R is hydrogen and neither of $R^7$ and $R^8$ contains carboxy, hydroxy, amino, thiol, or guanidino; i.e. the compound of formula (1E)

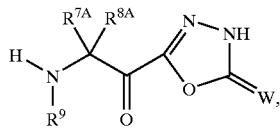

(IE)

wherein all symbols are the same meaning as above, maybe prepared by subjecting to deprotection reaction of protective group for amino the compound among the compound of formula (IA) which is prepared by the method as above, wherein $R^A$ is a protective group for amino, i.e. the compound of formula (IA-2)

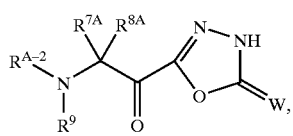

(IA-2)

wherein $R^{A-2}$ is a protective group for amio and the other symbols are the same meanings as above.

Protective groups for amino includes, for example, benzyloxycarbonyl, t-butoxycarbonyl, trifluoroacetyl, 9-fluorenylmethoxycarbonyl, but other groups that can be easily and selectively eliminated may also be used instead. For example, the groups described in T. W. Greene, Protective Groups inorganic Synthesis, Wiley, New York, 1991 may be used.

Deprotection reactions for protective groups for amino is known, for example, 1) a deprotection reaction under alkaline conditions,
2) a deprotection reaction under acidic conditions,
3) a deprotection reaction by hydrogenolysis, etc. may be included.

To explain these methods concretely, 1) a deprotection reaction under alkaline conditions is, for example, carried out in an organic solvent (methanol, tetrahydrofuran, dioxane, dimethylformamide, etc.) using a hydroxide of alkali metal (sodium hydroxide, potassium hydroxide, lithium hydroxide, etc.), hydroxide of alkaline earth metal (barium hydroxide, calcium hydroxide, etc.), organic amine (triethylamine, N-methylmorpholine, diisopropylethylamine, piperidine, etc.) or a quaternary ammonium salt (tetrabutyl ammonium fluoride etc.) or a solution thereof or a mixture thereof at a temperature between 0 and 40° C.

2) a deprotection reaction under acidic conditions is, for example, carried out in an organic solvent (methylenechloride, chloroform, dioxane, ethylacetate, anisole, etc.), using organic acid (acetic acid, trifluoroacetic acid, methanesulfonic acid, etc.) or an inorganic acid (hydrochloric acid, sulfuric acid, etc.) or a mixture thereof (hydrobromic acid/acetic acid, etc.) at a temperature between 0 and 100° C.

3) a deprotection reaction by hydrogenolysis is, for example, carried out in a solvent (ethers (tetrahydrofuran, dioxane, dimethoxyethane, diethyl ether, etc.), alcohols (methanol, ethanol, etc.), benzenes (benzene, toluene, etc.), ketones (acetone, methyl ethyl ketone, etc.), nitriles (acetonitrile etc.), amides (dimethylformamide etc.), water, ethyl acetate, acetic acid or a mixture of more than two from above etc.) in the presence of a catalyst (palladium-carbon, palladium black, palladium hydroxide, platinum oxide, Raney nickel, etc.) under the atmosphere of hydrogen of normal or suppressed pressure, or in the presence of ammonium formate at a temperature between 0 and 200° C.

As easily understood by those skilled in the art, the compounds of the present invention may be easily prepared by these reactions.

(3) Among the compound of formula (I), wherein $AA^1$ and $AA^2$ are a single bond at the same time and at least one of R, $R^7$ and $R^8$ contains carboxy, hydroxy, amino, thiol or guanidino or R is hydrogen; i.e. the compound of formula (IB)

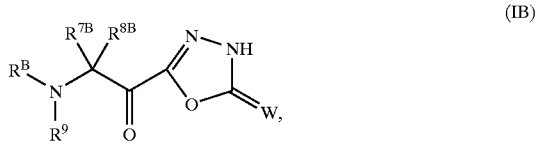

(IB)

wherein $R^B$, $R^{7B}$ and $R^{8B}$ are the same meanings as R, $R^7$ and $R^8$ respectively, with proviso that at least one of them contains carboxy, hydroxy, amino, thiol or guanidino, or $R^B$ is hydrogen, and the other symbols are the same meanings as above, maybe prepared by subjecting to a deprotection reaction of protective groups for carboxy, hydroxy, amino, thiol or guanidino, the compound, among the compound of formula (IA) which is prepared by the method as above, wherein at least one of $R^A$, $R^{7A}$ and $R^{8A}$ contains a protected form of carboxy, hydroxy, amino, thiol or guanidino; i.e. the compound of formula (IA-1)

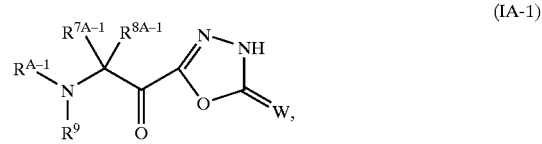

(IA-1)

wherein $R^{A-1}$, $R^{7A-1}$, $R^{8A-1}$ are the same meanings as $R^A$, $R^{7A}$ and $R^{8A}$ respectively, with proviso that at least one of $R^{A-1}$, $R^{7A-1}$ and $R^{8A-1}$ contains a protected form of carboxy, hydroxy, amino, thiol or guanidino, or $R^{A-1}$ is a protective group for amino. And the other symbols are the same meanings as above, or the compound, among the compound of formula (IE) which is prepared by the method as above, wherein at least one of $R^{7A}$ or $R^{8A}$ is a protected form of carboxy, hydroxy, amino, thiol or guanidino; i.e. the compound of formula (IE-1)

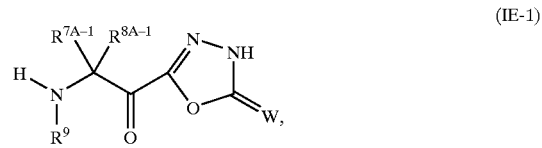

(IE-1)

wherein all symbols are the same meanings as above.

Protective groups for carboxy include, for example, methyl, ethyl, t-butyl and benzyl.

Protective groups for hydroxy include, for example, methoxymethyl, 2-tetrahydropyranyl, t-butyldimethylsilyl, t-butyldiphenylsilyl, acetyl and benzyl.

Protective groups for amino include, the ones shown above.

Protective groups for thiol include, for example, benzyl, methoxybenzyl, methoxymethyl, 2-tetrahydropyranyl, diphenylmethyl and acetyl.

Protective groups for guanidino include, for example, benzyloxycarbonyl, t-butoxycarbonyl and 9-fluorenylmethoxycarbonyl.

As protective groups for carboxy, hydroxy, amino, thiol or guanidino group, other groups than above listed, if easily and selectively eliminated, may also be used instead. For example, the groups described in T. W. Greene, Protective Groups inorganic Synthesis, Wiley, New York, 1991 may be used.

Deprotection reactions of the protective groups of carboxy, hydroxy, amino, thiol or guanidino are well known, for example, 1) a deprotection reaction under alkaline conditions,
2) a deprotection reaction under acidic conditions,
3) a deprotection reaction by hydrogenolysis,
4) a deprotection reaction of silyl-containing groups, etc.
The methods of 1), 2) and 3) are carried out by the methods described above.
4) A deprotection reaction of silyl-containing group is, for example, carried out in a water-miscible organic solvent (tetrahydrofuran, acetonitrile, etc.) using tetrabutylammonium fluoride at a temperature between 0 and 40° C.

As easily understood by those skilled in the art, the target compounds of the present invention may be easily prepared by these reactions.

(4) Among the compound of formula (I). wherein $AA^1$ and $AA^2$ do not represent a single bond at the same time, and none of R, $AA^1$, $AA^2$, $R^7$ and $R^8$ contains carboxy, hydroxy, amino, thiol or guanidino; i.e. the compound of formula (IC)

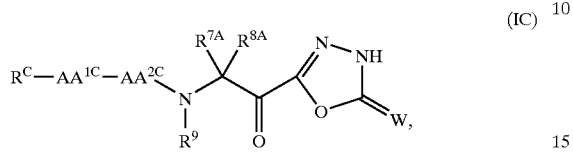
(IC)

wherein $R^C$, $AA^{1C}$ and $AA^{2C}$ are the same meanings as R, $AA^1$ and $AA^2$, respectively, with proviso that none of them contains carboxy, hydroxy, amino, thiol, guanidino and $AA^{1C}$ and $AA^{2C}$ do not represent a single bond at the same time and $R^C$ is not hydrogen, and the other symbols are the same meanings as above, may be prepared by the following methods [1] or [2].

The compound of formula (IC) may be prepared by subjecting to oxidation reaction the compound of formula (IIC)

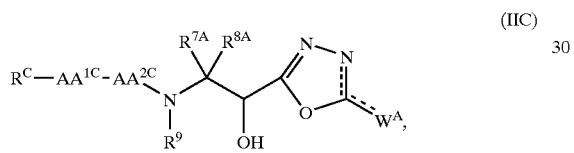
(IIC)

wherein all symbols are the same meanings as above, followed by deprotection reaction when $W^A$ is —S-Z.

A deprotection reaction and an oxidation reaction are carried out according to the methods described above.

[2] The compound of formula (IC) may be prepared by subjecting to amidation reaction the compound of formula (1E) and the compound of formula (X)

$R^C$—$AA^{1C}$—$AA^{2C}$—OH (X)

wherein all symbols are the same meanings as above.

Amidation reaction is known, for example,
1) a method using acid halide,
2) a method using mixed anhydride,
3) a method using a condensing agent (EDC, DCC, etc.), etc.

To explain these methods concretely,
1) a method using acid halide is, for example, carried out by subjecting to a reaction carboxylic acid in an organic solvent (chloroform, methylene chloride, diethyl ether, tetrahydrofuran, etc.) or without a solvent, and acid-halogenating agent (oxalyl chloride, thionyl chloride, etc.) at a temperature between −20° C. and refluxing temperature, and then subjecting to a reaction thus obtained acid halide with an amine in an organic solvent(chloroform, methylene chloride, diethyl ether, tetrahydrofuran, etc.) in the presence of tertiary amine (pyridine, triethylamine, dimethylaniline, dimethylaminopyridine, etc.) at a temperature between 0 and 40° C.

And it may be carried out by subjecting to a reaction with acid halide in an organic solvent (dioxane, tetrahydrofuran, etc.) using an aqueous alkali solution (an aqueous solution of sodium bicarbonate or sodium hydroxide) at a temperature between 0 and 40° C.

2) A method using mixed anhydride is, for example, carried out by subjecting to a reaction in an organic solvent (chloroform, methylene chloride, diethyl ether, tetrahydrofuran, etc.) or without a solvent, in the presence of tertiary amine (pyridine, triethylamine, dimethylaniline, dimethylaminopyridine, etc.) carboxylic acid with acid halide (pivaloyl chloride, tosyl chloride, mesylchloride, etc.) or acid derivative (chloroethyl formate, chloroisobutyl formate, etc.) at a temperature between 0 and 40° C., and then subjecting to a reaction thus obtained mixed anhydride with amine in an organic solvent (chloroform, methylene chloride, diethyl ether, tetrahydrofuran, etc.) at a temperature between 0 and 40° C.

3) A method using a condensing agent is, for example, carried out in an organic solvent (chloroform, methylene chloride, dimethylformamide, diethyl ether, tetrahydrofuran, etc.) or without a solvent, in the presence or absence of a tertiary amine (pyridine, triethylamine, dimethylaniline, dimethylaminopyridine, etc.), using a condensing reagent (1,3-dichlorohexylcarbodiimide (DCC), 1-ethyl-3-[3-(dimethylamino)propyl]carbodiimide (EDC), 1,1'-carbonyldiimidazole (CDI), 2-chloro-1-methylpyridinium iodide, etc.) in the presence or absence of 1-hydroxybenzotriazole (HOBt), by subjecting to a reaction carboxylic acid and amine at a temperature between 0 and 40° C.

The reactions 1), 2) and 3) are desirably carried out under atmosphere of inert gas (argon, nitrogen, etc.) under anhydrous conditions.

(5) Among the compound of formula (I), the compound wherein $AA^1$ and $AA^2$ do not represent a single bond at the same time and at least one of R, $AA^1$, $AA^2$, $R^7$ and $R^8$ contains carboxy, hydroxy, amino, thiol or guanidino, i.e. the compound of formula (ID)

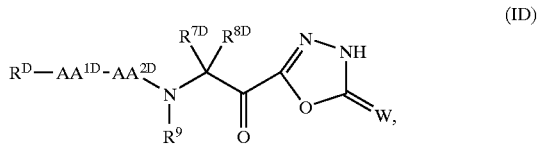
(ID)

wherein $R^D$, $AA^{1D}$, $AA^{2D}$, $R^{7D}$ and $R^{8D}$ are the same meanings as R, $AA^1$, $AA^2$, $R^7$ and $R^8$ respectively, with proviso that $AA^{1D}$ and $AA^{2D}$ do not represent a single bond at the same time and at least one of $R^D$, $AA^{1D}$, $AA^{2D}$, $R^{7D}$, $R^{8D}$ represents a group which contains carboxy, hydroxy, amino, thiol or guanidino, or $R^D$ is hydrogen, and the other symbols are the same meanings as above, may be prepared by subjecting to a deprotection reaction the compound, among the compound of formula (IC), wherein at least one of R, $AA^{1C}$, $AA^{2C}$, $R^{7A}$, $R^{8A}$ contains a protected form of carboxy, hydroxy, amino, thiol or guanidino, i.e. the compound of formula (IC-1)

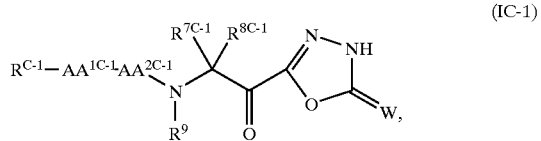 (IC-1)

wherein $R^{C-1}$, $AA^{1C-1}$, $AA^{2C-1}$, $R^{7C-1}$ and $R^{8C-1}$ are the same meanings as $R^C$, $AA^{1C}$, $AA^{2C}$, $R^{7A}$ and $R^{8A}$ respectively, with proviso that at least one of $R^{C-1}$, $AA^{C-1}$, $AA^{2C-1}$ $R^{7C-1}$ and $R^{8C-1}$ contains a protected form of carboxy, hydroxy, amino, thiol or guanidino, or $R^{C-1}$ is a protective group for amino group and the other symbols are the same meanings as above).

Deprotection reaction of protective group for carboxy, hydroxy, amino, thiol, guanidino are carried out according to the methods described above.

The compounds of formula (IIA) and (IIC) may be prepared by the method described in the following reaction scheme (1).

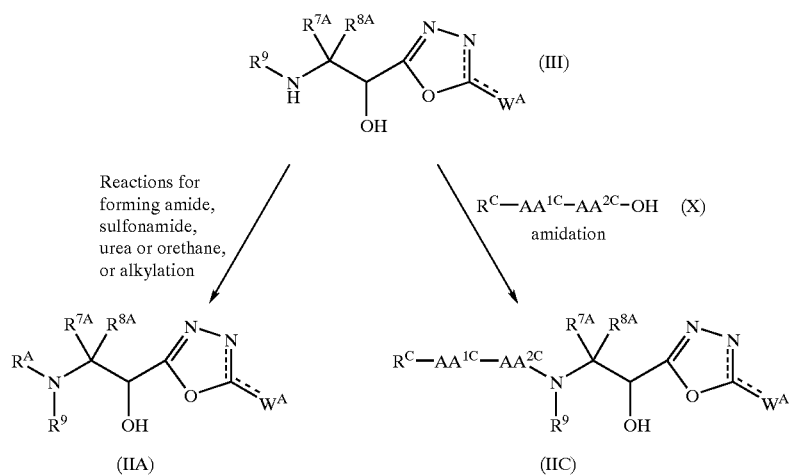

The compound of formula (III) maybe prepared by the method described in the following reaction scheme (2).

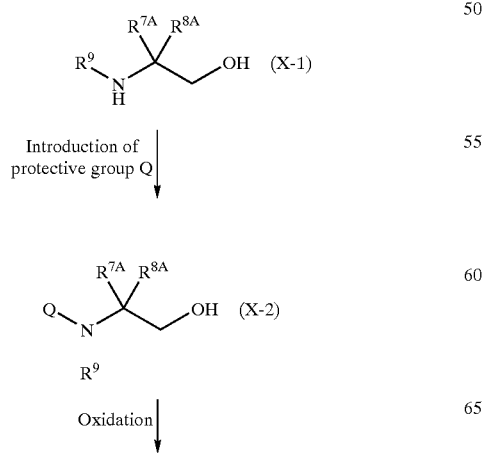

-continued

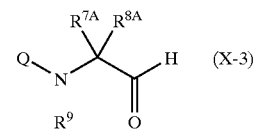 (X-3)

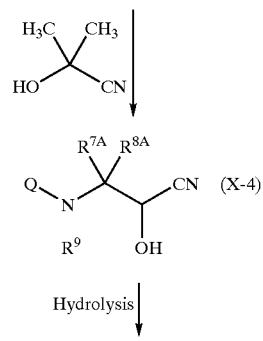 (X-4)

Hydrolysis

-continued

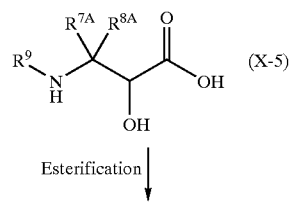 (X-5)

Esterification

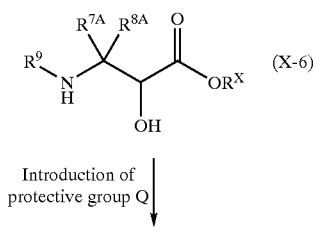 (X-6)

Introduction of protective group Q

-continued

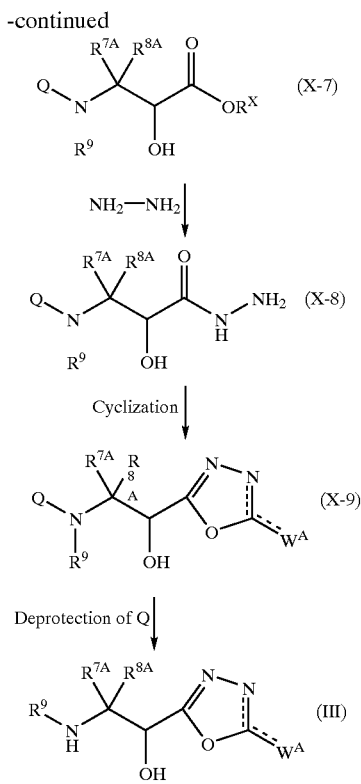

In the reaction scheme, Q is t-butoxycarbonyl or benzyloxycarbonyl, $R^X$ is methyl, ethyl or t-butyl and the other symbols are the same meanings as hereinbefore described. The compounds of formula (X) and (X-1), which should be used as starting materials, are known per se or may be prepared by known methods.

All reactions in the reaction schemes may be carried out by known methods.

Other starting materials and reagents in the present invention are known per se or may be prepared by conventional methods.

In each reaction of the present specification, reaction products maybe purified by conventional techniques. For example, purification maybe carried out by distillation under atmospheric or reduced pressure, by high performance liquid chromatography, thin layer chromatography or column chromatography using silica gel or magnesium silicate, by washing or by recrystallization, etc. Purification may be carried out after each reaction, or after a series of reactions.

Pharmacological Activity of the Compounds of the Present Invention

It was confirmed by the following experiments that the compounds of the present invention of formula (I) have an inhibitory activity against cysteine protease.

(i) Measurement of Cathepsin K Inhibitory Activity

Cathepsin K enzyme reaction buffer (50 mmol/L 2-(N-morpholino)ethanesulfonate, 2 mmol/L ethylenediamine tetraacetate (EDTA) and 4 mmol/L dithiothreitol (DTT) were mixed to adjust to pH 5.5) (65 µL), cysteine protease inhibitor solution (5 µL) of several concentrations, synthesized substrate (t-butyloxycarbonyl-L-alanyl-glycyl-L-prolyl-L-arginine-4-me thyl-chromanyl-7-amide) solution (20 µL) of several concentrations and cathepsin K enzyme solution (10 µL) were mixed and the increase of fluorescence intensity when reacted at 37° C. was measured (λex (excitation wavelength)355 nm, λem (fluorescence wavelength) 460 nm). As to the substrate and the compound of the present invention, enzyme reactions were carried out in combination of several appropriate concentrations, Dixon plotting was prepared, to define the absolute value of X-coordinate of the intersection point of the graph as Ki value.

It was confirmed that the compound of the present invention of formula (I) had an inhibitory activity more than 50% at 10 µM. For example, the Ki values of inhibitory activity of the compounds of example 1 and example 1 (1) were, 86 nM and 13 nM, respectively.

(ii) Measurement of Cathepsin B Inhibitory Activity

Synthesized substrate of several concentrations (carbobenzoxy-L-arginyl-L-arginine-4-methyl-chromanyl-7-amide or carbobenzoxy-L-phenylalanyl-L-arginine-4-methyl-chromanyl-7-amide) solution (10 µL), cysteine protease inhibitor solution of several concentrations (10 µL), cathepsin B enzyme reaction buffer (mixture of 400 mmol/L in acetic acid, 4 mmol/L EDTA, 8 mmol/L DDT to adjust to pH 5.5) 70 µL and cathepsin B enzyme solution 10 µL were mixed and the increase of fluorescence intensity was measured (λex=355 nm, λem=460 nm) when reacted at 37° C.

It was confirmed that the compound of the present invention of formula (I) had an inhibitory activity more than 50% at 10 µM. For example, the inhibitory activity of the compound of example 1 (1) was 97% at 1 µM.

(iii) Measurement of Cathepsin S Inhibitory Activity

Synthesized substrate of several concentrations (carbobenzoxy-L-leucyl-L-leucyl-L-arguinine-4-methyl-chroman yl-7-amide) solution (10 µL), cysteine protease inhibitor solution (5 µL) of several concentrations, cathepsin S enzyme reaction buffer (100 mmol/L sodium phosphate, 2 mmol/L EDTA, 2 mmol/L DTT were mixed to adjust to pH 6.5) (75 µL) and cathepsin S enzyme solution (10 µL) were mixed and the increase of fluorescence intensity was measured (λex=355 nm, λem=460 nm) when reacted at 37° C.

It was confirmed that the compound of the present invention of formula (I) has an inhibitory effect more than 50% at 10 µM. For example, the inhibitory activity of the compound of example 1 (1) was 99% at 1 µM.

(iv) Measurement of Cathepsin L Inhibitory Activity

Synthesized substrate of several concentrations (carbobenzoxy-L-phenylalanyl-L-arguine-4-methyl-chromanyl-7-amide or L-prolyl-L-phenylalanyl-L-arguinine-4-methyl-chromanyl-7-amide) solution (5 µL), cysteine protease inhibitor solution (5 µL) of several concentrations, cathepsin L enzyme reaction buffer (400 mmol/L acetic acid, 4 mmol/L EDTA, 8 mmol/L DTT were mixed to adjust to pH 5.5) 80 µL and cathepsin L enzyme solution (10 µL) were mixed and the increase of fluorescence intensity was measured (λex=355 nm, λem=460 nm) when reacted at 37° C.

It was confirmed that the compound of the present invention of formula (I) had an inhibitory activity of more than 50% at 10 µM. For example, the inhibitory activity of the compound of example 1 (1) was 100% at 1 µM.

(v) Measurement of Calpain Inhibitory Activity

The activity was measured according to the method described in Calcium-depending protease, Seibutsukagaku-Jikkenhou (Biochemistry Experimental Method) Tanpa-kubunkaikouso (Protease) I, 57 (1993).

(vi) Measurement of Caspase-1 Inhibitory Activity

Caspase-1 enzyme reaction solution (20 mmol/L 4-(2-hydroxyethyl)-1-piperazinethanesulfonate-sodium hydroxide buffer pH 7.4, 10 mmol/L potassium chloride, 1.5 mmol/L magnesium chloride, 0.1 mmol/L EDTA, 10% glycerol) 50 µL and cysteine protease inhibitor solution (50 µL) of several concentrations, caspase-1 enzyme solution (50 L) and synthesized substrate (acetyl-L-tyrosinyl-L-valinyl-L-alanyl-L-aspartic acid-4-methyl-chromanyl-7-amide) solution (100 µl) of several concentrations were reacted at 37° C. and the fluoroscene intensity was measured (λex=355 nm, λem=460 nm).

(vii) Investigation of Bone Resorption Inhibitory Activity Using Mouse Calvaria Cultivation System Mouse neonatal calvaria was cultured with a stimulant parathyroid hormone (PTH) or arotinoid in culture medium containing cysteine protease inhibitor (mixture of Penicillin G potassium (final concentration 100 U/mL), streptomycin sulfate (final concentration 0.1 mg/mL), bovine serum albumin (final concentration 0.1%), glutamine (final concentration 0.3 mg/mL) in D-minimal essential medium) at 37° C. and the calcium concentration in the culture medium was measured.

(viii) Bone Resorption Pit Formation Test Using Rabbit Osteoclast Cells

Osteoclast cells collected from rabbit bones were sowed over slices of bovine cortical bone, dentine or teeth of toothed whale and was cultured in α-minimal essential medium containing final concentration 5% fetal bovine serum and various concentrations of cysteine protease inhibitor at 37° C. The pits formed on the slices by the osteoclast were observed and at the same time type-I collagen C-terminal telopeptide (CTx) concentration in culture medium was measured.

(ix) Investigation of Immune Reaction Inhibitory Effect Using Antigen-Sensitized Mouse Spleen Cells Spleen cells were collected from mice sensitized by ovalbumin (OVA) several times. Inhibitory effect of cysteine protease inhibitors against immune response induced by OVA stimulus was investigated, using cytokine concentration and immunoglobulin concentration in culture solution as indicators.

(x) Investigation of Inhibitory Effect Against Bone Resorption Using Rat PTH Hypercalcemia Model The effect of cysteine protease inhibitor (compulsory oral administration, intraperitoneal administration) on bone resorption which was promoted by intravenous administration of parathyroid hormone (PTH) solution (30 μg/mL) was investigated in rats, using calcium concentration in blood as an indicator.

(xi) Studies on Bone Resorption Inhibitory Effect Using TPTx Rat PTHrP Induced Hypercalcemia Model The effect of cysteine protease inhibitor (compulsory oral administration, intraperitoneal administration) on bone resorption, promoted by subcutaneously parathyroid hormone related peptide (PTHrP) administration to a fasting thyroparathyroidectomized (TPTx) rat was investigated, using calcium concentration in blood as an indicator.

Toxicity

The toxicity of the compounds of the present invention is very low and therefore it was confirmed that the compounds are safe for pharmaceutical use.

Industrial Applicability

Application to Pharmaceuticals

The compound of formula (I) of the present invention has an inhibitory activity against cysteine proteases, and therefore it is useful as an agent for the prophylaxis and/or treatment of inflammatory diseases (periodontitis, arthritis, inflammatory bowel diseases, infectious diseases, pancreatitis, hepatitis, glomerulonephritis, endocarditis, myocarditis, etc.), diseases induced by apoptosis (graft versus host diseases, rejection of an organ transplantation, acquired immune deficiency syndrome (AIDS), AIDS-related complex (ARC), adult T cell leukemia, hairy cells leukemia, spondylopathy, disorders of respiratory apparatus, arthritis, HIV or HTLV-1 related diseases such as uveitis, virus-related diseases such as hepatitis C, cancer, collagenosis (systemic lupus erythematosus, rheumatoid arthritis, etc.), ulcerative colitis, Sjoegren's syndrome, primary biliary cirrhosis, spontaneous thrombocytopenic purpura, autoimmune hemolytic anemia, myasthenia gravis, autoimmune diseases such as insulin dependent (type I) diabetes, diseases accompanying thrombocytopenia (osteomyelodysplasia syndrome, periodic thrombocytopenia, aplastic anemia, spontaneous thrombocytopenia, disseminated intravascular coagulation (DIC), etc.), hepatic diseases such as viral hepatitis (type A, B, C, F, etc.) or hepatitis medicamentosa and cirrhosis, dementia such as Alzheimer's diseases and Alzheimer's senile dementia, cerebrovascular injury, nerve degeneration diseases, adult acute respiratory distress syndrome, infectious diseases, prostatomegaly, hysteromyoma, bronchial asthma, arteriosclerosis, all kinds of lusus naturae, nephropathy, senile cataract, chronic fatigue syndrome, myodystrophy, peripheral neuropathy, etc.), diseases induced by disorders of immune response (graft versus host diseases, rejection of an organ transplantation, allergic diseases (bronchial asthma, atopic dermatitis, allergic rhinitis, pollinosis, diseases induced by house dusts, irritablepneumonia, food allergy, etc.), psoriasis, rheumatoid arthritis, etc.), autoimmune diseases (insulin-dependent (type I) diabetes, systemic lupus erythematosus, Hashimoto's diseases, multiple sclerosis, etc.), desease by decomposing various proteins which compose the organism (myodystrophy, cataract, periodontitis, hepatocyte desease by bile acid such as cholestatic cirrhosis, etc.), decomposition of alveolus elastica such as pulmonary emphysema, ischemic diseases (brain ischemia, brain disorders by ischemic reperfusion, myocardial infarction, ischemic hepatopathy, etc.), shock (septic shock, systemic inflammation response syndrome, endotoxin shock, acidosis, etc.), circulatory system disorders (arteriosclerosis, restenosis after percutaneous transluminal coronary angioplasty (PTCA), etc.)), blood coagulation disorders (thrombocytopenic purpura, hemolytic uremic syndrome, etc.), malignant tumor, acquired immune deficiency syndrome (AIDS) and AIDS-related complex (ARC), parasitic diseases such as malaria, nerve degenerative diseases (Alzheimer-type dementia, Huntington's chorea, Parkinson's diseases, multiple sclerosis, traumatic encephalopathy, traumatic spondylopathy, etc.), pulmopathy such as fibroid lungs, bone resorption diseases (osteoporosis, rheumatoidarthritis, arthritis, osteoarthritis, hypercalcemia, osteometastasis of cancer etc.), endocrinesthenia such as hyperthyroidism.

For the purpose described above, the compounds of formula (I), of the present invention, non-toxic salts thereof, acid addition salts thereof or hydrates thereof may normally be administered systemically or locally, usually by oral or parenteral administration.

The doses to be administered are determined depending upon, for example, age, body weight, symptom, the desired therapeutic effect, the route of administration, and the duration of the treatment. In the human adult, the doses per person at a time are generally from 1 mg to 1000 mg, by oral administration, up to several times per day, and from 1 mg to 100 mg, by parenteral administration (preferably intravenous administration), up to several times per day, or continuous administration for from 1 to 24 hours per day from vein.

As mentioned above, the doses to be used depend upon various conditions. Therefore, there are cases wherein doses lower than or greater than the ranges specified above may be used.

The compounds of the present invention may be administered in the form of, for example, solid compositions, liquid compositions or other compositions for oral administration, injections, liniments or suppositories for parenteral administration.

Solid compositions for oral administration include compressed tablets, pills, capsules, dispersible powders and granules.

Capsules include hard capsules and soft capsules.

In such solid compositions, one or more of the active compound(s) may be used as a dosage form, as is normal practice, to admix with excipient (e.g. lactose, mannitol, glucose, microcrystalline cellulose, starch), combining agents(hydroxypropyl cellulose polyvinyl pyrrolidone or magnesium metasilicate aluminate), disintegrating agents (e.g. cellulose calciumglycolate), lubricating agents (e.g. magnesium stearate), stabilizing agents, agents to assist dissolution (e.g. glutamic acid or asparatic acid) and the like. The agents may, if desired, be coated with coating agents (e.g. sugar, gelatin, hydroxypropyl cellulose or hydroxypropylmethyl cellulose phthalate), or be coated with two or more films. Further, coating may include containment within capsules of absorbable materials such as gelatin.

Liquid compositions for oral administration include pharmaceutically acceptable solutions, suspensions, emulsions, syrups and elixirs. In such compositions, one or more of the active compound(s) are dissolved, suspended or emulsified in diluent commonly used (e.g. purified water, ethanol or mixture thereof). Furthermore, such liquid compositions may also comprise wetting agents or suspending agents, emulsifying agents, sweetening agents, flavouring agents, perfuming agents, preserving agents buffer agent etc.

Injections for parenteral administration include solutions, suspensions, emulsions and solids which are dissolved or suspended to use at a time to use. One or more of the active compound(s) in injections are dissolved, suspended and emulsified in a solvent. The solvents are, for example, distilled water for injection, physiological salt solution, vegetable oil, propylene glycol, polyethylene glycol, alcohol such as ethanol or mixture thereof. Moreover the injections may also include stabilizing agents, agents to assist dissolution (e.g. glutamic acid, aspartic acid or POLYSORBATE80 (registered trade mark)), suspending agents, emulsifying agents, soothing agents, buffer agents, preserving agents, etc. They are sterilized in the last process or manufactured and prepared by sterile procedure. They may also be manufactured in the form of sterile solid compositions such as freeze-dried one and they may be sterilized or dissolved to use in sterile distilled water for injection or some other solvents immediately before use.

Other compositions for parenteral administration include liquids for external use, and ointment, endermic liniments, inhale, spray, suppositories for rectal administration and pessaries for vaginal administration which comprise one or more of the active compound(s) and are prescribed by methods known per se.

Spray compositions may comprise additional substances other than diluents: e.g. stabilizing agents (e.g. sodium sulfite hydride), isotonic buffers (e.g. sodium chloride, sodium citrate or citric acid). For preparation of such spray compositions, for example, the method described in the U.S. Pat. Nos. 2,868,691 or 3,095,355 may be used.

BEST MODE FOR CARRYING OUT THE INVENTION

The following reference examples and examples are intended to illustrate, but do not limit, the present invention.

The solvents in parentheses show the eluting or developing solvents and the ratios of the solvents used are by volume in chromatographic separations.

The solvents in the parenthesis of NMR show the solvents used for measurement.

REFERENCE EXAMPLE 1
(2S)-2-(t-butoxycarbonylamino)-4-methylpentanol

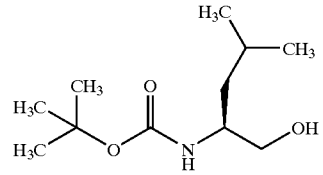

To a solution of (2S)-2-amino-4-methylpentanol ((L)-leucinol) (20 g) in tetrahydrofuran (THF; 1000 ml) was added di-t-butyl-dicarbonate (43 ml) dropwise at 0° C. and the mixture was stirred for 1.5 hours at room temperature. The reaction mixture was concentrated to give the crude product of the title compound having the following physical data.

TLC: Rf 0.50 (chloroform:methanol=10:1);
NMR (CDCl$_3$): δ 4.58 (br, 1H), 3.81–3.45 (m, 3H), 1.80–1.60 and 1.37–1.25 (each m, totally 3H), 1.45 (s, 9H), 0.95–0.91 (m, 6H)

REFERENCE EXAMPLE 2
(2S)-2-(t-butoxycarbonylamino)-4-methylpentanal

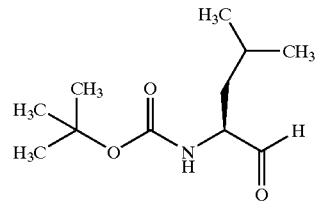

To a solution of the crude compound prepared in reference example 1 in dimethylsulfoxide (DMSO; 344 ml) were added triethylamine (72 ml) and sulfur trioxide-pyridine complex (82 g) in DMSO (280 ml) at 10° C. and the mixture was stirred for 1 hour. The reaction mixture was poured into ice-water and was extracted with ethyl acetate. The organic layer was washed with 10% aqueous solution of citric acid, water and saturated aqueous solution of sodium chloride successively and dried over anhydrous sodium sulfate and concentrated to give the crude of the title compound product having the following physical data.

TLC: Rf 0.45 (chloroform:methanol=10:1);
NMR (CDCl$_3$): δ 9.59 (s, 1H), 4.91 (br, 1H), 4.12 (br, 1H), 1.80–1.60 and 1.40–1.30 (each m, totally 3H), 1.46 (s, 9H), 1.00–0.87 (m, 6H).

REFERENCE EXAMPLE 3
(3S)-3-(t-butoxycarbonylamino)-2-hydroxy-5-methylhexanenitrile

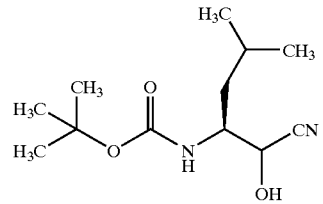

To a solution of the crude compound prepared in reference example 2 in methanol (180 ml) was added acetone cyanohydrine (19 ml) and potassium carbonate (4.7 g) at 0° C. and the mixture was stirred for 1 hour at room temperature. The reaction mixture was concentrated and the residue was extracted with ethyl acetate and water. The organic layer was washed with water and saturated aqueous solution of sodium chloride, dried over anhydrous sodium sulfate and concentrated. The residue was purified by column chromatography on silica gel (n-hexane:ethyl acetate=3:1) to give the title compound (33.6 g) having the following physical data.

TLC: Rf 0.40 (n-hexane:ethyl acetate=3:1);

NMR (CDCl$_3$): δ 4.85–4.80 (m, 1H), 4.60–4.45 (m, 1H), 4.00–3.70 (m, 1H), 1.80–1.40 (m, 3H), 1.45 and 1.43 (each s, totally 9H), 1.00–0.90 (m, 6H).

REFERENCE EXAMPLE 4

(3S)-3-amino-2-hydroxy5-methylhexanoic acid hydrochloride

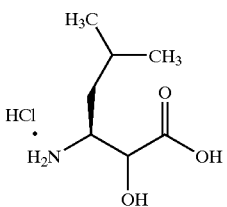

To the compound prepared in reference example 3 (33.6 g) was added conc. hydrochloric acid (300 ml) and the mixture was stirred for 5 hours at 80° C. The reaction mixture was concentrated to give the crude product of the title compound having the following physical data.

TLC: Rf 0.30 (chloroform:methanol:water=6:4:1)

REFERENCE EXAMPLE 5

(3S)-3-amino-2-hydroxy-5-methylhexanate methyl ester hydrochloride

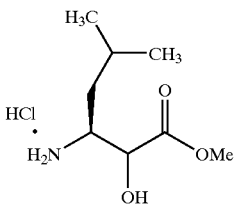

To methanol (1000 ml) was added thionyl chloride (92 ml) at −40° C. and the mixture was stirred for 10 minutes. The obtained solution was added to a solution of the compound prepared in reference example 4 in methanol (250 ml) at −10° C. dropwise and the mixture was stirred for 4 hours at room temperature. The reaction mixture was concentrated to give the crude product of the title compound having the following physical data.

TLC: Rf 0.50 (chloroform:methanol:water=6:4:1).

REFERENCE EXAMPLE 6

(3S)-3-(t-butoxycarbonylamino)-2-hydroxy-5-methylhexanoic acid methyl ester

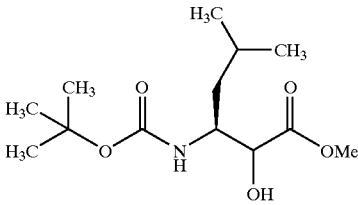

To a solution of the crude compound prepared in reference example 5 (32 g) in methylene chloride (300 ml) were added triethylamine (20 ml) and di-t-butyl bicarbonate (34 ml) at 0° C. and the mixture was stirred for 4 hours at room temperature. To the reaction mixture was added water and was extracted with ethyl acetate. The organic layer was washed with 10% aqueous solution of citric acid, a saturated aqueous solution of sodium bicarbonate, water and saturated aqueous solution of sodium chloride successively, dried over anhydrous sodium sulfate and was concentrated. The residue was purified by column chromatography on silica gel (n-hexane:ethyl acetate=3:1) to give the title compound (28 g) having the following physical data.

TLC: Rf 0.40 and 0.35 (n-hexane:ethyl acetate=3:1);

NMR (CD$_3$OD): δ 4.10–4.09 (m, 1H), 4.04–3.95 and 3.93–3.85 (each m, totally 1H), 3.72 and 3.70 (each s, totally 3H), 1.70–1.08 (m, 3H), 1.43 and 1.40 (each s, totally 9H), 0.98–0.82 (m, 6H).

REFERENCE EXAMPLE 7

(3S)-3-(t-butoxycarbonylamino)-2-hydroxy-5-methylhexanoylhyd razide

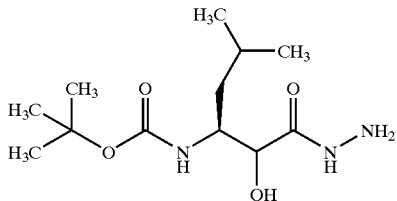

To hydrazine hydrate (99 ml) was added a solution of the compound prepared in reference example 6 (28 g) in methanol (110 ml) at 0° C. and the mixture was stirred for 1 hour at room temperature. To the reaction mixture was added water and was extracted with methylene chloride. The organic layer was washed with saturated aqueous solution of sodium chloride, dried over anhydrous sodium sulfate and was concentrated to give the title compound (21 g) having the following physical data.

TLC: Rf 0.40 (chloroform:methanol:water=9:1:0.1);

NMR (CD$_3$OD): δ 4.10 (d, J=3.6 Hz, 0.5H), 4.00–3.90 (m, 1.5H), 1.70–1.30 (m, 3H), 1.43 and 1.41 (each s, totally 9H), 0.95–0.88 (m, 6H).

REFERENCE EXAMPLE 8

(2S)-2-(t-butoxycarbonylamino)-4-methyl-1-(2-oxo-1,3,4-oxadi azolin-5-yl)pentanol

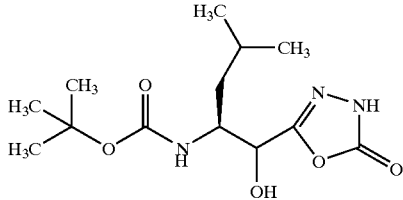

To a solution of the compound prepared in reference example 7 (20 g) and 1,1-carbonyldiimidazole (14 g) in THF (400 ml) was added triethylamine (12 ml) at 0° C. and the mixture was stirred for 5 hours at room temperature. To the reaction mixture was added 10% aqueous solution of citric acid and was extracted with ethyl acetate. The organic layer was washed with a saturated aqueous solution of sodium bicarbonate, water and saturated aqueous solution of sodium chloride successively, dried over anhydrous sodium sulfate and was concentrated. The residue was purified by column chromatography on silica gel (chloroform:methanol=20:1) to give the title compound (17 g) having the following physical data.

TLC: Rf 0.50 and 0.45 (chloroform:methanol=10:1);

NMR (CDCl$_3$): δ 4.87 and 4.80 (each brd, each J=9.3 Hz, totally 1H), 4.60–4.50 (m, 1H), 4.10–3.90 (m, 1H), 1.80–1.30 (m, 3H), 1.45 and 1.41 (each s, totally 9H), 1.00–0.80 (m, 6H).

REFERENCE EXAMPLE 9

(2S)-2-amino-4-methyl-1-(2-oxo-1,3,4-oxadiazolin-5-yl) pentanol.hydrochloride

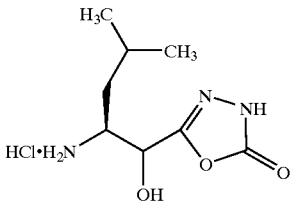

To a solution of the compound prepared in reference example 8 (3.01 g) in ethyl acetate (6 ml) was added 4N hydrochloric acid-ethyl acetate (40 ml) and the mixture was stirred for 30 minutes. The reaction mixture was concentrated to give the crude product of the title compound having the following physical data.

TLC: Rf 0.51 (chloroform:methanol:water=6:4:1).

REFERENCE EXAMPLE 10

1-[(1R,2S)-2-(benzoylamino)cyclohexyl]-N-[(2S)-1-hydroxy4-methyl-1-(2-oxo-1,3,4-oxadiazolin-5-yl)-2-pentyl]carboxamide

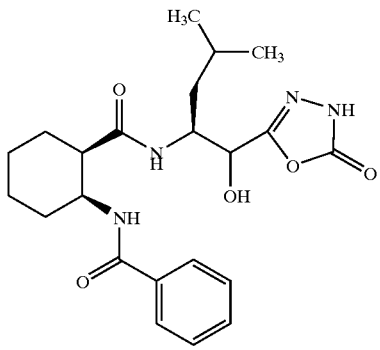

To a solution of the compound prepared in reference example 9 in N,N-dimethylformamide (DMF: 20 ml) were added (−)-2-benzamidocyclohexanecarboxylic acid ((1R, 2S)-2-(benzoylamino) cyclohexanecarboxylic acid) (2.60 g), 1-hydroxybenzotriazole (2.30 g), 1-ethyl-3-(3-dimethylaminopropyl)carbodiimide hydrochloride (1.74 g) and N-methylmorpholine (1.32 ml) and the mixture was stirred overnight. To the reaction mixture was added ice-water and was extracted with ethylacetate. The organic layer was washed with a saturated aqueous solution of sodium bicarbonate, water and saturated aqueous solution of sodium chloride successively, dried over anhydrous sodium sulfate and was concentrated. The residue was purified by column chromatography on silica gel (chloroform:methanol=1:0~100:1~20:1) to give the title compound (3.01 g) having the following physical data.

TLC: Rf 0.33 (chloroform:methanol=9:1);

NMR (CDCl$_3$): δ 10.88 and 10.69 (each br, totally 1H), 7.74 (d, J=7.3 Hz, 2H), 7.60–7.30 (m, 3H), 7.12 and 7.05 (each d, J=7.6 and 8.2 Hz, totally 1H), 6.86 and 6.72 (each d, J=8.8 and 9.2 Hz, totally 1H), 5.28 and 5.12 (each br, totally 1H), 4.60 (s, 1H), 4.40–4.05 (m, 2H), 2.82 (br, 1H), 2.30–1.10 (m, 11H), 0.90–0.50 (m, 6H)

EXAMPLE 1

1-[(1R,2S)-2-(benzoylamino)cyclohexyl]-N-[(2S)-4-methyl-1-oxo-1-(2-oxo-1,3,4-oxadiazolin-5-yl)-2-pentyl] carboxamide

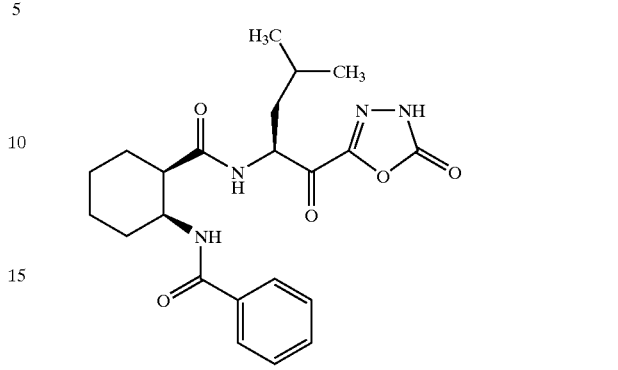

To a solution of the compound prepared in reference example 10 (2.68 g) in methylene chloride (20 ml) was added diacetoxyiodo)benzene (2.41 g) and TEMPO reagent (2,2,6,6-tetramethyl-1-piperidinyloxy, free radical) (97 mg) and the mixture was stirred for 5.5 hours. To the reaction mixture was added a saturated aqueous solution of sodium bicarbonate and was extracted with chloroform. The organic layer was washed with saturated aqueous solution of sodium chloride, dried over anhydrous sodium sulfate and was concentrated. The residue was purified by column chromatography on silica gel (chloroform:methanol=1:0 to 100:1) to give the compound of the present invention (2.50 g) having the following physical data.

TLC: Rf 0.44 (chloroform:methanol=9:1);

NMR (CDCl$_3$): δ 11.75 (br, 1H), 7.77 (dd, J=7.8, 1.6 Hz, 2H), 7.60–7.30 (m, 3H), 7.13 (d, J=8.4 Hz, 1H), 6.68 (d, J=8.0 Hz, 1H), 5.45–5.25 (m, 1H), 4.50–4.30 (m, 1H), 2.89 (q, J=5.4 Hz, 1H), 2.20–1.30 (m, 11H), 0.82 (d, J=5.8 Hz, 3H), 0.80 (d, J=5.8 Hz, 3H).

Example 1 (1) to Example 1 (28)

By the same procedure described in reference example 10→example 1 using the compound prepared in reference example 9 or a racemic isomer thereof and a compound corresponding to (−)-2-benzamidocyclohexanecarboxylic acid, the compounds of the present invention having the following physical data were obtained.

Example 1 (1)

(2S)-N-[(2S)-4-methyl-1-oxo-1-(2-oxo-1,3,4-oxadiazolin-5-yl)-2-pentyl]-4-methyl-2-(benzyloxycarbonylamino) pentanamide

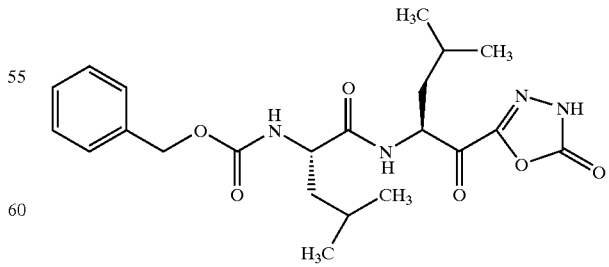

TLC: Rf 0.41 (n-hexane:ethyl acetate=1:1);

NMR (CDCl$_3$): δ 10.68 (br, 1H), 7.35 (s, 5H), 6.99 and 6.72 (each br, J=6.9 Hz, totally 1H), 5.40–5.02 (m, 4H), 4.22 (m, 1H), 1.80–1.20 (m, 6H), 1.02–0.81 (m, 12H).

Example 1 (2)

N-[4-methyl-1-oxo-1-(2-oxo-1,3,4-oxadiazolin-5-yl)-2-pentyl]cyclohexanecarboxamide

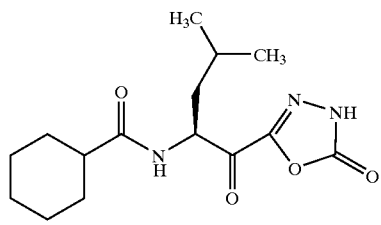

TLC: Rf 0.38 (chloroform:methanol=9:1);

NMR (CDCl₃): δ 11.74 (br, 1H), 6.20 (d, J=8.4 Hz, 1H), 5.49 (dt, J=4.0, 8.4 Hz, 1H), 2.30–2.10 (m, 1H), 2.00–1.10 (m, 13H), 1.00 (d, J=6.2 Hz, 3H), 0.96 (d, J=6.2 Hz, 3H).

Example 1 (3)

1-[(1S,2R)-2-(benzoylamino)cyclohexyl]-N-[4-methyl-1-oxo-1-(2-oxo-1,3,4-oxadiazolin-5-yl)-2-pentyl]carboxamide

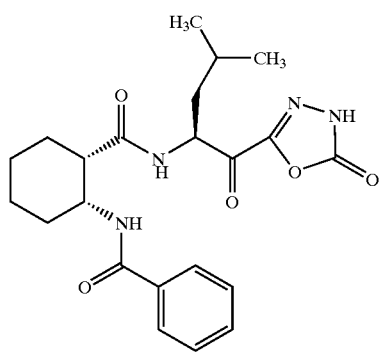

TLC: Rf 0.5–6 and 0.53 (chloroform:methanol=9:1);

NMR (CDCl₃): δ 11.17 (br, 1H), 7.77 (dd, J=8.2, 1.8 Hz, 2H), 7.55–7.35 (m, 3H), 7.14 and 7.07 (each d, J=9.2 and 8.4 Hz, totally 1H), 6.68 and 6.47 (each d, J=8.0 Hz, totally 1H), 5.30–5.10 (m, 1H), 4.45–4.25 (m, 1H), 2.93 (q, J=4.8 Hz, 1H), 2.20–1.30 (m, 11H), 1.05–0.70 (m, 6H).

Example 1 (4)

1-[(1S,2R)-2-(benzoylamino)cyclohexyl]-N-[(2S)-4-methyl-1-oxo-1-(2-oxo-1,3,4-oxadiazolin-5-yl)-2-pentyl]carboxamide

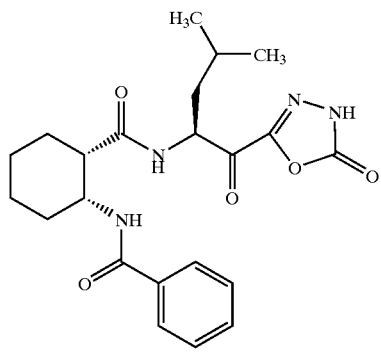

TLC: Rf 0.45 (chloroform:methanol=9:1);

NMR (CDCl₃): δ 11.34 (br, 1H), 7.76 (d, J=6.9 Hz, 2H), 7.55–7.35 (m, 3H), 7.10 (d, J=8.4 Hz, 1H), 6.71 (d, J=6.6 Hz, 1H), 5.30–5.15 (m, 1H), 4.40–4.25 (m, 1H), 2.93 (q, J=4.9 Hz, 1H), 2.10–1.30 (m, !1H), 0.97 (d, J=6.3 Hz, 3H), 0.94 (d, J=6.3 Hz, 3H).

Example 1 (5)

1-(2-benzyloxy)phenyl-N-[4-methyl-1-oxo-1-(2-oxo-1,3,4-oxadiazolin-5-yl)-2-pentyl]carboxamide

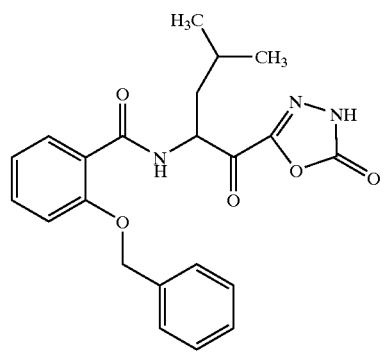

TLC: Rf 0.31 (chloroform:methanol=19:1);

NMR (CDCl₃): δ 11.44 (br, 1H), 8.61 (d, J=7.2 Hz, 1H), 8.21 (dd, J=8.1, 1.8 Hz, 1H), 7.60–7.35 (m, 6H), 7.20–7.05 (m, 2H), 5.51 (ddd, J=10.2, 7.2, 4.2 Hz, 1H), 5.23 (d, J=10.2 Hz, 1H), 5.17 (d, J=10.2 Hz, 1H), 1.50–1.10 (m, 3H), 0.85 (d, J=6.3 Hz, 3H), 0.70 (d, J=6.3 Hz, 3H).

Example 1 (6)

N-[4-methyl-1-oxo-1-(2-oxo-1,3,4-oxadiazolin-5-yl)-2-pentyl]-3-cyclopentylpropanamide

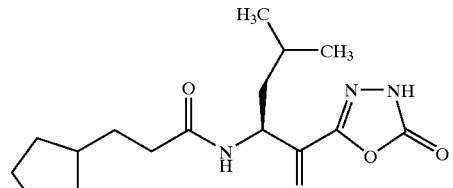

TLC: Rf 0.58 (chloroform:methanol=9:1);

NMR (CDCl₃): δ 11.60 (br, 1H), 6.18 (d, J=8.1 Hz, 1H), 5.49 (ddd, J=9.6, 8.1, 3.9 Hz, 1H), 2.40–2.20 (m, 2H), 2.10–1.40 (m, 12H), 1.10 (br, 2H), 1.00 (d, J=6.0 Hz, 3H), 0.97 (d, J=6.3 Hz, 3H).

Example 1 (7)

(2S)-N-[(2S)-1-oxo-1-(2-oxo-1,3,4-oxadiazolin-5-yl)-4-phenyl-2-butyl]-4-methyl-2-(benzyloxycarbonylamino)pentanamide

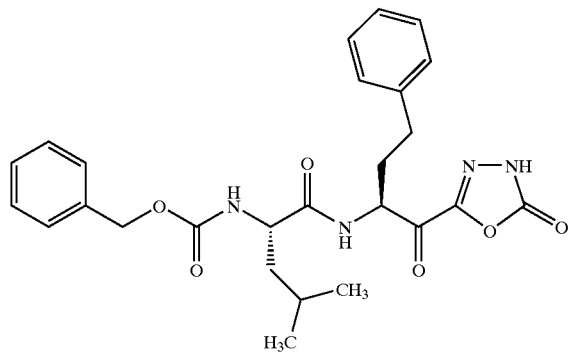

TLC: Rf 0.47 (n-hexane:ethyl acetate=2:3);

NMR (CDCl$_3$): δ 7.40–7.05 (m, 10H), 6.97 (d, J=5.6 Hz, 1H), 5.40–5.20 (m, 2H), 5.12 (s, 2H), 4.30–4.10 (m, 1H), 2.66 (t, J=7.4 Hz, 2H), 2.40–1.30 (m, 5H), 1.00–0.80 (m, 6H).

Example 1 (8)

1-[(1R,2S)-2-(4-methoxybenzoylamino)cyclohexyl]-N-[(2S)-4-methyl-1-oxo-1-(2-oxo-1,3,4-oxadiazolin-5-yl)-2-pentyl]carboxamide

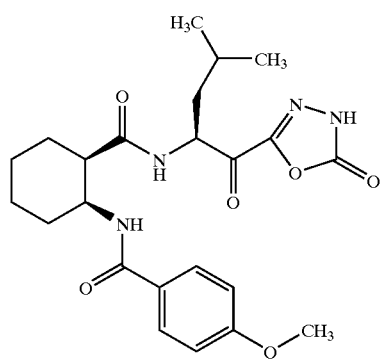

TLC: Rf 0.33 (chloroform:methanol=9:1);

NMR (CDCl$_3$): δ 11.60–11.30 (br, 1H), 7.73 (d, J=9.0 Hz, 2H), 7.00 (d, J=8.4 Hz, 1H), 6.91 (d, J=9.0 Hz, 2H), 6.83–6.77 and 6.65–6.56 (each m, total 1H), 5.33–5.13 (m, 1H), 4.42–4.28 (m, 1H), 3.84 (s, 3H), 2.94–2.85 (m, 1H), 2.14–1.35 (m, 11H), 0.97–0.91 and 0.83–0.76 (each m, total 6H).

Example 1 (9)

1-[(1R,2S)-2-(quinoxalin-2-ylcarbonylamino)cyclohexyl]-N-[(2S)-4-methyl-1-oxo-1-(2-oxo-1,3,4-oxadiazolin-5-yl)-2-pentyl]carboxamide

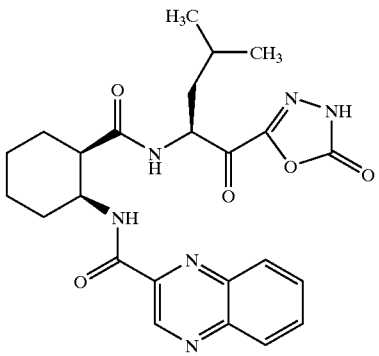

TLC: Rf 0.29 (chloroform:methanol=9:1);

NMR (CDCl$_3$): δ 11.45–11.15 (br, 1H), 9.62 (s, 1H), 8.53 (d, J=8.7 Hz, 1H), 8.24–8.10 (m, 2H), 7.93–7.82 (m, 2H), 6.54 (d, J=7.8 Hz, 1H), 5.37–5.26 (m, 1H), 4.60–4.46 (m, 1H), 2.96–2.80 (m, 1H), 2.28–1.20 (m, 11H), 0.96–0.90, 0.71 and 0.67 (m and each d, J=6.0 Hz, total 6H).

Example 1 (10)

1-[(1R,2S)-2-(naphthalen-2-ylcarbonylamino)cyclohexyl]-N-[(2S)-4-methyl-1-oxo-1-(2-oxo-1,3,4-oxadiazolin-5-yl)-2-pentyl]carboxamide TLC: Rf 0.30 (chloroform:methanol=9:1);

NMR (CDCl$_3$): δ 11.85–11.50 (br, 1H), 8.30 (s, 1H), 7.97–7.74 (m, 4H), 7.60–7.47 (m, 2H), 7.32–7.23 (m, 1H), 6.63 (d, J=8.1 Hz, 1H), 5.38–5.10 (m, 1H), 4.50–4.37 (m, 1H), 3.00–2.86 (m, 1H), 2.24–1.35 (m, 11H), 0.97–0.88 and 0.80–0.65 (each m, total 6H).

Example 1 (11)

1-[(1R,2S)-2-(benzo[b]thiophen-2-ylcarbonylamino)cyclohexyl]-N-[(2S)-4-methyl-1-oxo-1-(2-oxo-1,3,4-oxadiazolin-5-yl)-2-pentyl]carboxamide

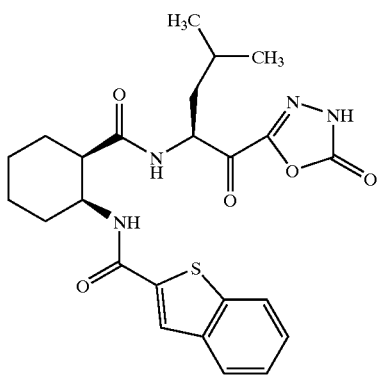

TLC: Rf 0.48 (chloroform:methanol=9:1);

NMR (CD$_3$OD): δ 7.97 (s, 1H), 7.96–7.80 (m, 2H), 7.48–7.37 (m, 2H), 5.21–5.07 (m, 1H), 4.33–4.25 (m, 1H), 3.02–2.80 (m, 1H), 2.27–2.12, 2.07–1.92 and 1.82–1.36 (each m, total 11H), 0.95, 0.92, 0.72 and 0.71 (each d, J=6.0 Hz, total 6H).

Example 1 (12)

1-[(1R,2S)-2-(4-nitrobenzoylamino)cyclohexyl]-N-[(2S)-4-methyl-1-oxo-1-(2-oxo-1,3,4-oxadiazolin-5-yl)-2-pentyl]carboxamide

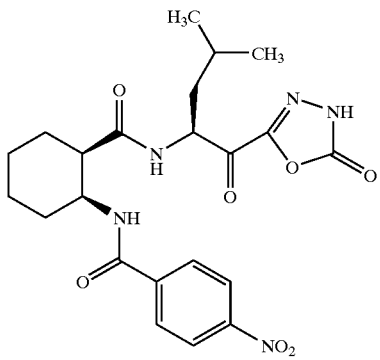

TLC: Rf 0.47 (chloroform:methanol=9:1);

NMR (CD$_3$OD): δ 8.30 (d, J=9.0 Hz, 2H), 7.97 (d, J=9.0 Hz, 2H), 5.16–5.05 (m, 1H), 4.43–4.27 (m, 1H), 2.94–2.82 (m, 1H), 2.25–2.06, 2.06–1.89 and 1.80–1.34 (each m, total 11H), 0.96, 0.95, 0.84 and 0.78 (each d, J=6.0 Hz, total 6H).

Example 1 (13)

1-[(1R,2S)-2-(4-chlorobenzoylamino)cyclohexyl]-N-[(2S)-4-methyl-1-oxo-1-(2-oxo-1,3,4-oxadiazolin-5-yl)-2-pentyl]carboxamide

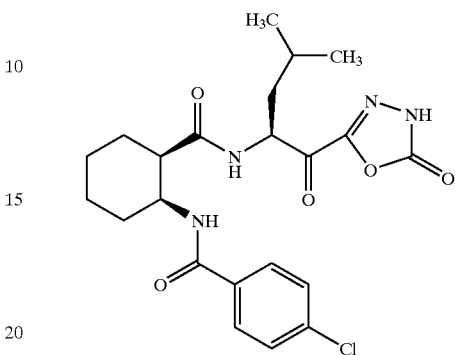

TLC: Rf 0.45 (chloroform:methanol=9:1);

NMR (CDCl$_3$): δ 11.50–10.70 (br, 1H), 7.72 (d, J=8.4 Hz, 2H), 7.40 (d, J=8.4 Hz, 2H), 7.18 and 7.01 (each d, J=7.8 Hz, total 1H), 6.67 and 6.43 (each d, J=7.8 Hz, total 1H), 5.37–5.16 (m, 1H), 4.44–4.26 (m, 1H), 2.93–2.78 (m, 1H), 2.13–1.40 (m, 11H), 0.97, 0.95 and 0.84 (each d, J=6.0 Hz, total 6H).

Example 1 (14)

1-[(1R,2S)-2-(4-phenylbenzoylamino)cyclohexyl]-N-[(2S)-4-methyl-1-oxo-1-(2-oxo-1,3,4-oxadiazolin-5-yl)-2-pentyl]carboxamide

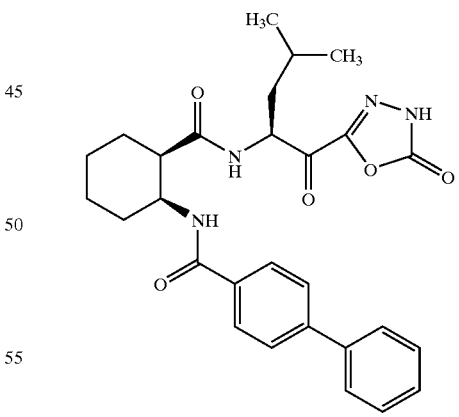

TLC: Rf 0.48 (chloroform:methanol=9:1);

NMR (CDCl$_3$): δ 7.89–7.80 (m, 2H), 7.72–7.55 (m, 4H), 7.50–7.32 (m, 3H), 7.15 and 7.07 (each d, J=8.1 Hz, 1H), 6.74 and 6.50 (each d, J=7.8 Hz, 1H), 5.37–5.15 (m, 1H), 4.47–4.30 (m, 1H), 2.96–2.80 (m, 1H), 2.18–1.30 (m, 11H), 0.96, 0.94, 0.82 and 0.80 (each d, J=6.0 Hz, total 6H).

Example 1 (15)

1-[(1R,2S)-2-(4-fluorobenzoylamino)cyclohexyl]-N-[(2S)-4-methyl-1-oxo-1-(2-oxo-1,3,4-oxadiazolin-5-yl)-2-pentyl]carboxamide

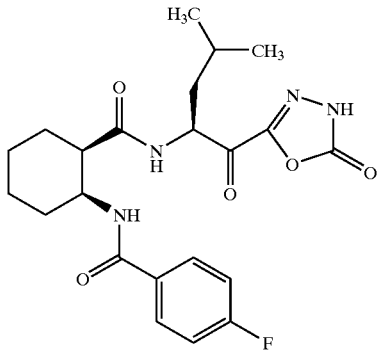

TLC: Rf 0.40 (chloroform:methanol=9:1);

NMR (CDCl$_3$): δ 7.85–7.74 (m, 2H), 7.18–7.05 and 6.99 (m and d, J=8.1 Hz, total 3H), 6.69 and 6.46 (each d, J=7.5 Hz, total 1H), 5.36–5.16 (m, 1H), 4.43–4.26 (m, 1H), 2.94–2.75 (m, 1H), 2.15–1.38 (m, 11H), 0.96, 0.95 and 0.83 (each d, J=6.3 Hz, total 6H).

Example 1 (16)

1-[(1R,2S)-2-(4-t-butylbenzoylamino)cyclohexyl]-N-[(2S)-4-methyl-1-oxo-1-(2-oxo-1,3,4-oxadiazolin-5-yl)-2-pentyl]carboxamide

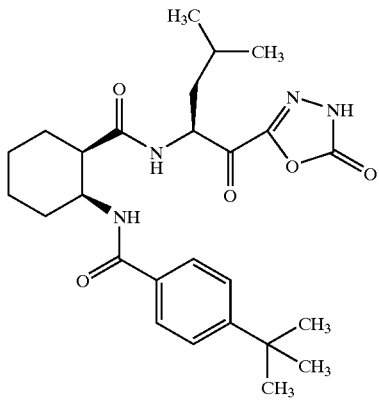

TLC: Rf 0.39 (chloroform:methanol=9:1);

NMR (CDCl$_3$): δ 8.02 and 7.71 (each d, J=8.4 Hz, total 2H), 7.48 and 7.44 (each d, J=8.4 Hz, total 2H), 7.06 and 7.00 (each d, J=8.1 Hz, total 1H), 6.79 and 6.58 (each d, J=7.5 Hz, total 1H), 5.33–5.14 (m, 1H), 4.46–4.27 (m, 1H), 2.96–2.78 (m, 1H), 2.16–1.36 (m, 1H), 1.35 and 1.32 (each s, total 9H), 0.98–0.90 and 0.83–0.74 (each m, total 6H).

Example 1 (17)

1-[(1R,2S)-2-(4-methylbenzoylamino)cyclohexyl]-N-[(2S)-4-methyl-1-oxo-1-(2-oxo-1,3,4-oxadiazolin-5-yl)-2-pentyl]carboxamide

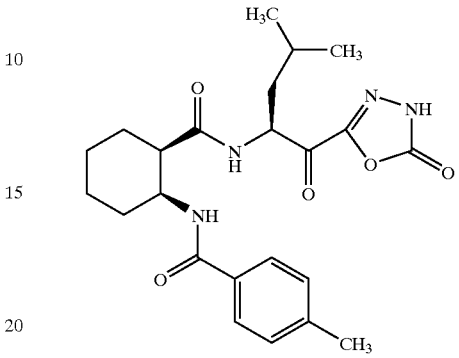

TLC: Rf 0.37 (chloroform:methanol=9:1);

NMR (CDCl$_3$): δ 7.97 and 7.66 (each d, J=8.1 Hz, total 2H), 7.22 (d, J=8.1 Hz, 2H), 7.04 and 6.98 (each d, J=8.1 Hz, total 1H), 6.78 and 6.58 (each d, J=7.5 Hz, total 1H), 5.33–5.13 (m, 1H), 4.44–4.28 (m, 1H), 2.95–2.74 (m, 1H), 2.38 (s, 3H), 2.20–1.30 (m, 11H), 1.00–0.89 and 0.85–0.72 (each m, total 6H).

Example 1 (18)

1-[(1R,2S)-2-(4-trifluoromethylbenzoylamino)cyclohexyl]-N-[(2S)-4-methyl-1-oxo-1-(2-oxo-1,3,4-oxadiazolin-5-yl)-2-pentyl]carboxamide

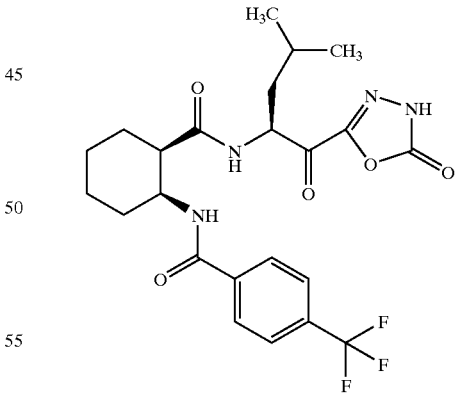

TLC: Rf 0.38 (chloroform:methanol=9:1);

NMR (CDCl$_3$): δ 7.90 (d, J=8.1 Hz, 2H), 7.69 (d, J=8.1 Hz, 2H), 7.35 and 7.12 (each d, J=8.1 Hz, total 1H), 6.64 and 6.38 (each d, J=7.5 Hz, total 1H), 5.38–5.18 (m, 1H), 4.44–4.27 (m, 1H), 2.95–2.80 (m, 1H), 2.17–1.30 (m, 11H), 0.97, 0.96 and 0.84 (each d, J=6.0 Hz, total 6H).

Example 1 (19)

1-[(1R,2S)-2-(2-fluorobenzoylamino)cyclohexyl]-N-[(2S)-4-methyl-1-oxo-1-(2-oxo-1,3,4-oxadiazolin-5-yl)-2-pentyl]carboxamide

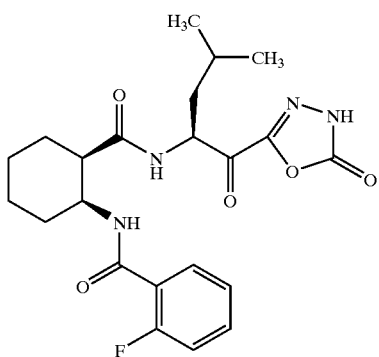

TLC: Rf 0.36 (chloroform:methanol=9:1);

NMR (CDCl$_3$): δ 8.06–7.97 (m, 1H), 7.60–7.33 (m, 2H), 7.33–7.21 (m, 1H), 7.18–7.06 (m, 1H), 6.82 and 6.58 (each d, J=7.8 Hz, total 1H), 5.42–5.18 (m, 1H), 4.58–4.40 (m, 1H), 2.93–2.74 (m, 1H), 2.17–1.32 (m, 11H), 0.95, 0.83 and 0.78 (each d, J=6.0 Hz, total 6H).

Example 1 (20)

1-[(1R,2S)-2-(pyridin-2-ylcarbonylamino)cyclohexyl]-N-[(2S)-4-methyl-1-oxo-1-(2-oxo-1,3,4-oxadiazolin-5-yl)-2-pentyl]carboxamide

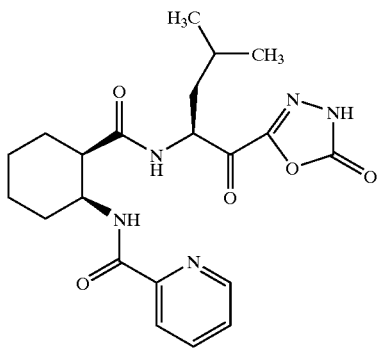

TLC: Rf 0.33 (chloroform:methanol=9:1);

NMR (CDCl$_3$): δ 8.67–8.51 (m, 2H), 8.18–8.09 (m, 1H), 7.89–7.80 (m, 1H), 7.48–7.38 (m, 1H), 6.97 and 6.72 (each d, J=7.5 Hz, total 1H), 5.39–5.17 (m, 1H), 4.66–4.38 (m, 1H), 2.90–2.72 (m, 1H), 2.20–1.33 (m, 11H), 0.92, 0.76 and 0.72 (each d, J=6.0 Hz, total 6H).

Example 1 (21)

1-[(1R,2S)-2-(2-methylthiopyridin-3-ylcarbonylamino)cyclohexyl]-N-[(2S)-4-methyl-1-oxo-1-(2-oxo-1,3,4-oxadiazolin-5-yl)-2-pentyl]carboxamide

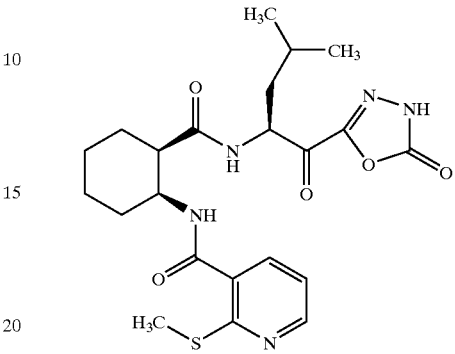

TLC: Rf 0.33 (chloroform:methanol=9:1);

NMR (CDCl$_3$): δ 8.50 (dd, J=4.8, 1.8 Hz, 1H), 7.82 and 7.76 (each dd, J=7.8, 1.8 Hz, total 1H), 7.17 (d, J=8.7 Hz, 1H), 7.04 (dd, J=7.8, 4.8 Hz, 1H), 6.84 and 6.50 (each d, J=6.9 Hz, total 1H), 5.34–5.16 (m, 1H, 4.54–4.36 (m, 1H), 2.93–2.75 (m, 1H), 2.56 and 2.55 (each s, total 3H), 2.17–1.30 (m, 11H), 0.96, 0.87 and 0.86 (each d, J=6.0 Hz, total 6H).

Example 1 (22)

1-[(1R,2S)-2-(2-chloropyridin-5-ylcarbonylamino)cyclohexyl]-N-[(2S)-4-methyl-1-oxo-1-(2-oxo-1,3,4-oxadiazolin-5-yl)-2-pentyl]carboxamide

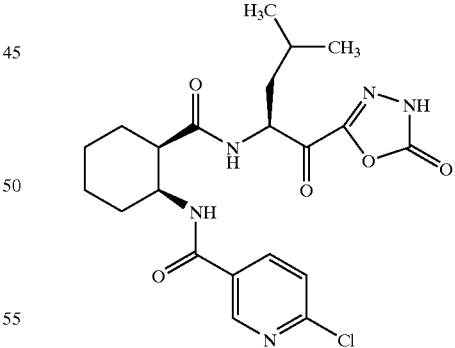

TLC: Rf 0.33 (chloroform:methanol=9:1);

NMR (CDCl$_3$): δ 8.79 and 8.77 (each d, J=2.1 Hz, total 1H), 8.14–8.04 (m, 1H), 7.52 and 7.30 (each d, J=8.1 Hz, total 1H), 7.41 (d, J=8.1 Hz, 1H), 6.71 and 6.46 (each d, J=7.5 Hz, total 1H), 5.38–5.23 (m, 1H), 4.40–4.23 (m, 1H), 2.98–2.75 (m, 1H), 2.14–1.32 (m, 1H), 0.98, 0.96, 0.88 and 0.87 (each d, J=6.0 Hz, total 6H).

Example 1 (23)

1-[(1R,2S)-2-(naphthalen-1-ylmethylcarbonylamino)cyclohexyl]-N-[(2S)-4-methyl-1-oxo-1-(2-oxo-1,3,4-oxadiazolin-5-yl)-2-pentyl]carboxamide

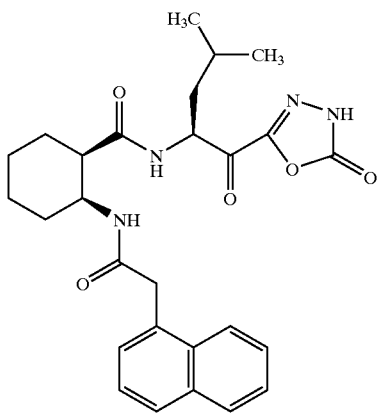

TLC: Rf 0.38 (chloroform:methanol=9:1);

NMR (CDCl$_3$): δ 8.05–7.71 (m, 3H), 7.62–7.32 (m, 4H), 6.37 (d, J=7.2 Hz, 1H), 6.28 (d, J=8.7 Hz, 1H), 5.25–5.08 (m, 1H), 4.34–4.10 (m, 1H), 4.05 (d, J=16.5 Hz, 1H), 3.94 (d, J=16.5 Hz, 1H), 2.65–2.46 (m, 1H), 2.00–1.13 (m, 11H), 0.99 (d, J=5.4 Hz, 6H).

Example 1 (24)

1-[(1R,2S)-2-(4-cyanobenzoylamino)cyclohexyl]-N-[(2S)-4-methyl-1-oxo-1-(2-oxo-1,3,4-oxadiazolin-5-yl)-2-pentyl]carboxamide

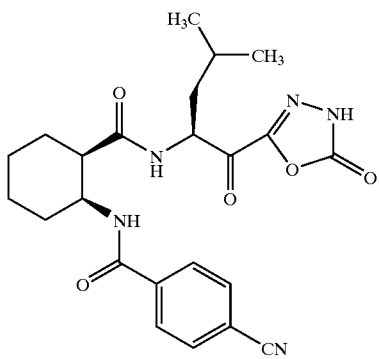

TLC: Rf 0.46 (chloroform:methanol=9:1);

NMR (CDCl$_3$): δ 7.89 (d, J=8.4 Hz, 2H), 7.74 (d, J=8.4 Hz, 2H), 7.46 (d, J=8.4 Hz, 1H), 6.38 (d, J=7.8 Hz, 1H), 5.43–5.13 (m, 1H), 4.45–4.25 (m, 1H), 2.96–2.78 (m, 1H), 2.17–1.33 (m, 11H), 0.87 (d, J=5.8 Hz, 6H).

Example 1 (25)

1-[(1R,2S)-2-(N-benzoyl-N-methylamino)cyclohexyl]-N-[(2S)-4-methyl-1-oxo-1-(2-oxo-1,3,4-oxadiazolin-5-yl)-2-pentyl]carboxamide

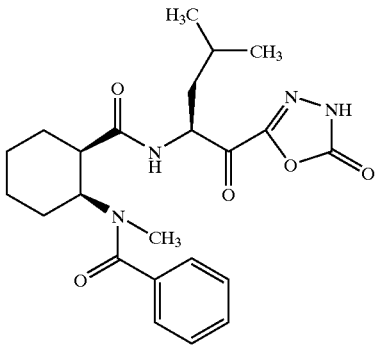

TLC: Rf 0.40 (chloroform:methanol=9:1);

NMR (CDCl$_3$): δ 7.50–7.20 (m, 5H), 6.77–6.44 (br, 1H), 5.35–5.20 (m, 1H), 4.68–4.18 (br, 1H), 3.35–3.00 (br, 1H), 2.89 (s, 3H), 2.62–2.33 (m, 1H), 2.18–1.19 (m, 10H), 0.89 (d, J=6.0 Hz, 6H).

Example 1 (26)

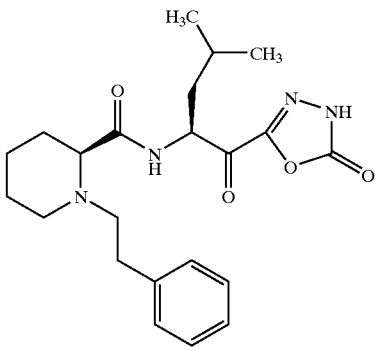

TLC: Rf 0.45 (chloroform:methanol=9:1);

NMR (CDCl$_3$): δ 7.35–7.14 (m, 5H), 7.12–6.96 (br, 1H), 5.27–5.17 (m, 1H), 3.43–3.24 (m, 1H), 3.03–2.73 (m, 4H), 2.51–2.36 (m, 1H), 2.20–2.07 (m, 1H), 2.05–1.91 (m, 1H), 1.81–1.18 (m, 8H), 0.92 (d, J=6.0 Hz, 6H).

Example 1 (27)

1-[(2S)-N-(3-phenylpropyl)piperidin-2-yl]-N-[(2S)-4-methyl-1-oxo-1-(2-oxo-1,3,4-oxadiazolin-5-yl)-2-pentyl]carboxamide

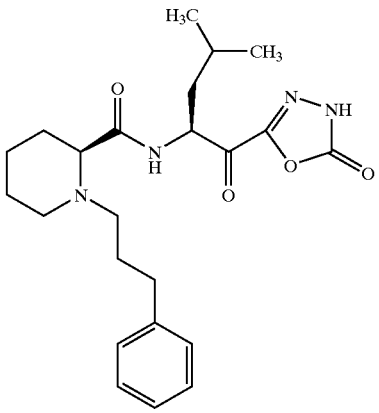

TLC: Rf 0.38 (chloroform:methanol=9:1);

NMR (CDCl$_3$): δ 7.70–7.40 (br, 1H), 7.37–7.07 (m, 5H), 5.44–5.30 (m, 1H), 3.25–3.11 (m, 1H), 2.98–2.48 (m, 5H), 2.40–2.20 (m, 1H), 2.20–1.16 (m, 11H), 1.07–0.83 (m, 6H).

Example 1 (28)

1-[(1R,2S)-2-(4-dimethylaminomethylbenzoylamino)cyclohexyl]-N-[4-methyl-1-oxo-1-(2-oxo-1,3,4-oxadiazolin-5-yl)-2-pentyl]carboxamide

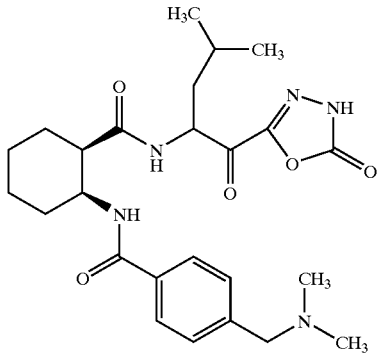

TLC: Rf 0.46 and 0.41 (chloroform:methanol=7:3);

NMR (CDCl$_3$): δ 7.76 and 7.73 (each d, J=7.8 and 7.6 Hz, total 2H), 7.50–7.20 (m, 3H), 6.72 and 6.61 (each d, J=8.0 and 7.6 Hz, total 1H), 5.40–5.25 (m, 1H), 4.45–4.20 (m, 1H), 3.98, 3.91 and 3.84 (d, d and s, J=12.4 Hz, total 2H), 2.95–2.75 (m, 1H), 2.61 and 2.51 (each s, total 6H), 2.20–1.40 (m, 1H), 0.95, 0.92, 0.85 and 0.81 (each d, J=6.2 Hz, total 6H).

REFERENCE EXAMPLE 11

(2S)-2-(N-t-butoxycarbonylamino)-4-methyl-1-(2-thioxo-1,3,4-oxadiazolin-5-yl)pentanol

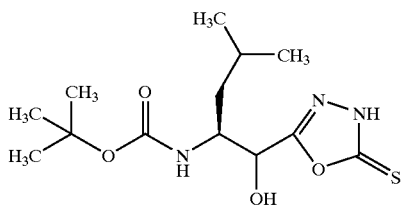

To a solution of the compound prepared in reference example 7 (3.0 g) in 95% ethanol (55 ml) were added potassium hydroxide (726 mg) and carbon disulfide (662 ml) and the mixture was stirred overnight at 90° C. The reaction mixture was cooled down to room temperature, and thereto was added cold 10% aqueous solution of citric acid and was extracted with ethyl acetate. The organic layer was washed with saturated aqueous solution of sodium chloride, dried over anhydrous sodium sulfate and was concentrated. The residue was purified by column chromatography on silica gel (ethyl acetate) and again thereto was added 10% aqueous solution of citric acid and was extracted with ethyl acetate. The organic layer was washed with saturated aqueous solution of sodium chloride, dried over anhydrous sodium sulfate and was concentrated to give the title compound (3.1 g) having the following physical data.

TLC: Rf 0.31 (n-hexane:ethyl acetate=1:1);

NMR (CDCl$_3$): δ 11.80 (br, 1H), 5.28 and 5.09 (each br, total 1H), 5.00–4.40 (m, 2H), 4.20–3.90 (m, 1H), 2.00–1.20 (m, 3H), 1.47 and 1.43 (each s, total 9H), 1.05–0.85 (m, 6H).

REFERENCE EXAMPLE 12

1-[(1R,2S)-2-(benzoylamino) cyclohexyl]-N-[(2S)-4-methyl-1-hydroxy-1-(2-thio-1,3,4-oxadiazolin-5-yl)-2-pentyl]carboxamide

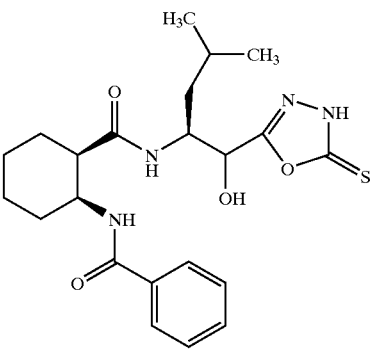

By the same procedure as described in reference example 9→reference example 10 using the compound prepared in reference example 11 (350 mg) the title compound (380 mg) having the following physical data was obtained.

TLC: Rf 0.55 (ethyl acetate);

NMR (CDCl$_3$): δ 7.90–7.70 (m, 2H), 7.60–7.30 (m, 3H), 7.21 and 7.11 (each d, J=7.0 and 7.6 Hz, total 1H), 6.97 and 6.77 (each d, J=8.8 and 8.4 Hz, total 1H), 4.85–4.75 (m, 1H), 4.45–4.15 (m, 2H), 2.95–2.80 (m, 1H), 2.20–1.20 (m, 1H), 0.80–0.50 (m, 6H).

REFERENCE EXAMPLE 13

1-[(1R,2S)-2-(benzoylamino)cyclohexyl]-N-[(2S)-4-methyl-1-hydroxy-1-(2-thienylmethylthio-1,3,4-oxadiazolin-5-yl)-2-pentyl]carboxamide

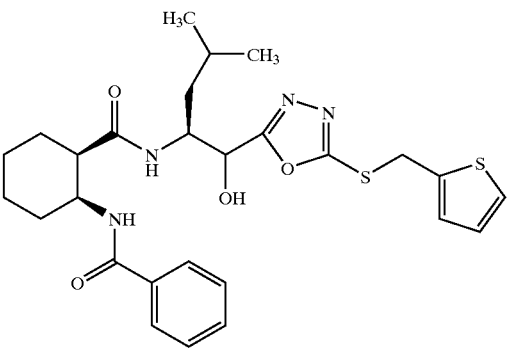

To a solution of the compound prepared in reference example 12 (360 mg) in DMF (1.6 ml) was added potassium carbonate (133 mg) and the mixture was stirred for 3.5 hours. To the mixture was added thienylmethyl bromide (186 mg) and the mixture was stirred for 1.5 hours at room temperature. To the reaction mixture was added water and was extracted with ethyl acetate. The organic layer was washed with water, dried over anhydrous sodium sulfate and concentrated. The residue was purified by column chromatography on silica gel (n-hexane:ethyl acetate=2:1) to give the title compound (370 mg) having the following physical data.

TLC: Rf 0.33 (chloroform:methanol=9:1);

NMR (CDCl$_3$): δ 7.80–7.70 (m, 2H), 7.60–7.35 (m, 3H), 7.30–7.05 (m, 3H), 6.95–6.85 (m, 1H), 6.35–6.20 (m, 1H), 4.95–4.80 (m, 1H), 4.68 and 4.66 (each s, total 2H), 4.60–4.15 (m, 3H), 2.85–2.70 (m, 1H), 2.20–1.20 (m, 11H), 0.90–0.70 (m, 6H).

REFERENCE EXAMPLE 14

1-[(1R,2S)-2-(benzoylamino)cyclohexyl]-N-[(2S)-4-methyl-1-oxo-1-(2-thienylmethylthio-1,3,4-oxadiazolin-5-yl)-2-pentyl]carboxamide

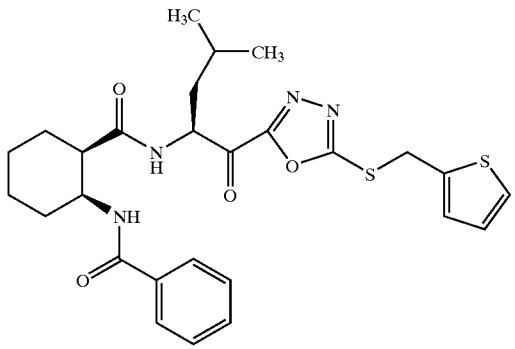

By the same procedure as described in example 1 using the compound prepared in reference example 13 (365 mg), the title compound (330 mg) having the following physical data was obtained.

TLC: Rf 0.35 (n-hexane:ethyl acetate=3:2);

NMR (CDCl$_3$): δ 7.77 (dd, J=7.9, 1.9 Hz, 2H), 7.55–7.35 (m, 3H), 7.30–7.10 (m, 3H), 6.95 (dd, J=5.1, 3.3 Hz, 1H), 6.28 (d, J=7.0 Hz, 1H), 5.50–5.35 (m, 1H), 4.79 (s, 2H), 2.87 (q, J=5.1 Hz, 1H), 2.20–1.30 (m, 11H), 0.91 (d, J=6.6 Hz, 3H), 0.85 (d, J=6.2 Hz, 3H).

EXAMPLE 2

1-[(1R,2S)-2-(benzoylamino)cyclohexyl]-N-[(2S)-4-methyl-1-oxo-1-(2-thio-1,3,4-oxadiazolin-5-yl)-2-pentyl]carboxamide

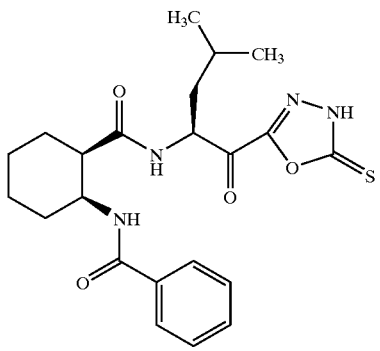

To a solution of the compound prepared in reference example acid-ethyl acetate (6 ml) and the mixture was stirred overnight. The reaction mixture was concentrated and a zeotroped with toluene. The residue was purified by column chromatography on silica gel (n-hexane:ethyl acetate=3:1→2:1→3:2) to give the title compound (130 mg) having the following physical data.

TLC: Rf 0.47 (chloroform:methanol:acetic acid =96:3:3);

NMR (CDCl$_3$): δ 7.78 (dd, J=7.9, 1.7 Hz, 2H), 7.55–7.30 (m, 3H), 7.08 (d, J=8.0 Hz, 1H), 6.68 (d, J=7.6 Hz, 1H), 5.40–5.10 (m, 1H), 4.50–4.30 (m, 1H), 2.97 (q, J=5.1 Hz, 1H), 2.20–1.30 (m, 11H), 1.00–0.70 (m, 6H).

Example 2 (1)

(2S)-N-[2(S)-4-methyl-1-oxo-1-(2-thio-1,3,4-oxadiazolin-5-yl)-2-pentyl]-4-methyl-2-(benzyloxycarbonylamino)pentanamide

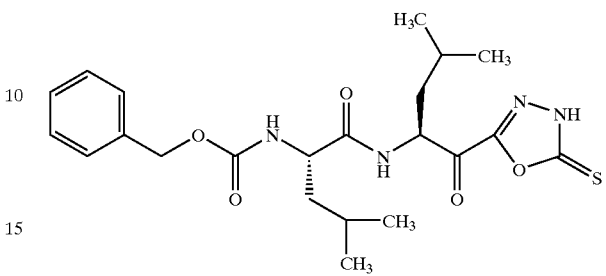

By the same procedure as described in reference example 12→reference example 13→reference example 14→example 2 using the compound prepared in reference example 11 and benzyloxycarbonyl leucine, the title compound having the following physical data was obtained.

TLC: Rf 0.29 (chloroform:methanol:acetic acid =48:1:1);

NMR (CDCl$_3$): δ 7.34 (s, 5H), 6.98 (d, J=6.2 Hz, 1H), 5.61 (d, J=8.0 Hz, 1H), 5.45–5.30 (m, 1H), 5.13 (s, 2H), 4.40–4.20 (m, 1H), 1.80–1.40 (m, 6H), 1.05–0.80 (m, 12H)

FORMULATION EXAMPLE

Formulation Example 1

The following components were admixed in a conventional method, dried, and punched out to give 100 tablets each containing 50 mg of active ingredient.

| | |
|---|---|
| N-[(1S)-2-(2-oxo-1,3,4-oxadiazolin-5-yl)-1-(2-methylpropyl)-2-oxoethyl)] [(2S, 1R)-2-(phenylcarbonylamino)cyclohexyl]carboxamide | 5.0 g |
| carboxymethylcellulose calcium (disintegrating agent) | 0.2 g |
| magnesium stearate (lubricant) | 0.1 g |
| microcrystalline cellulose | 4.7 g |

Formulation Example 2

The following components were admixed in a conventional method. The solution was sterilized in conventional method, placed 5 ml portions into ampoules and freeze-dried in a conventional method to give 100 ampoules each containing 20 mg of the active ingredient.

| | |
|---|---|
| N-[(1S)-2-(2-oxo-1,3,4-oxadiazolin-5-yl)-1-(2-methylpropyl)-2-oxoethyl] [(2S, 1R)-2-(phenylcarbonylamino)cyclohexyl]carboxamide | 2.0 g |
| mannitol | 20 g |
| distilled water | 500 ml |

What is claimed is:

1. A compound of formula (Id) or (Ia)'

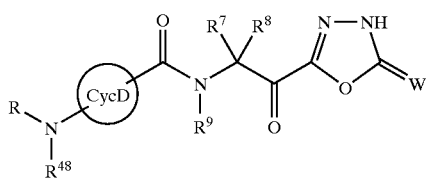 (Id)

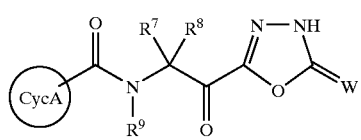 (Ia)' wherein W is oxygen or sulfur,

R is
(i) hydrogen,
(ii) C1–8 alkyl,
(iii) CycA,
(iv) C1–8 alkyl substituted with a group selected from halogen, CycA, nitro, $CF_3$ and cyano, (v) 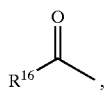, (vi) 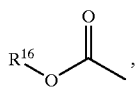, (vii) 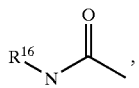, (viii) 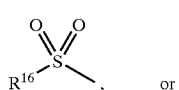, or (ix) 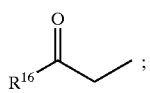;

CycA is a mono-, bi- or tri-cyclic C3–15 carboning
$R^{16}$ is
(1) C1–8 alkyl,
(2) C2–8 alkenyl,
(3) C2–8 alkynyl,
(4) CycA or
(5) C1–8 alkyl, C2–8 alkenyl or C2–8 alkynyl substituted with a group selected from halogen, nitro, $CF_3$, cyano, CycA, $NR^{18}R^{19}$ and —NHC(O)—CycA;
$R^{17}$ is hydrogen or C1–4 alkyl,
$R^{18}$ and $R^{19}$ are the same or different and represent hydrogen or C1–4 alkyl;
$R^{48}$ is hydrogen, C1–4 alkyl, phenyl or C1–4 alkyl substituted with phenyl;

CycD is a C3–C14 mono- or bi-cyclic carboring
$R^7$ and $R^8$ are the same or different and represent
(i) hydrogen,
(ii) C1–8 alkyl,
(iii) CycA or
(iv) C1–8 alkyl substituted with 1–5 of a group selected from the following (1) to (8):
(1) —$NR^{61}R^{62}$,
(2) —$OR^{63}$,
(3) —$SR^{64}$,
(4) —$COR^{65}$,
(5) —$NR^{66}CONR^{61}R^{62}$,
(6) guanidino,
(7) CycA, or
(8) —$NR^{66}SO_2R^{61}$, or $R^7$ and $R^8$ are taken together to form C2–8 alkylene, wherein one carbon atom may be replaced by oxygen, sulfur or —$NR^{60}$ and the alkylene may be substituted with —$NR^{61}R^{62}$ or —$OR^{63}$, $R^{60}$ is hydrogen, C1–4 alkyl, —COO—(C1–4 alkyl), phenyl or C1–4 alkyl substituted with phenyl, $R^{61}$, $R^{62}$, $R^{63}$, $R^{64}$ and $R^{66}$ are the same or different and represent hydrogen, C1–4 alkyl, phenyl or C1–4 alkyl substituted with phenyl, $R^{65}$ is C1–4 alkyl, phenyl, —$NR^{61}R^{62}$, wherein all symbols have the same meanings as above, —$OR^{63}$, wherein $R^{63}$ has the same meaning as above, or C1–4 alkyl substituted with phenyl;

$R^9$ is hydrogen, C1–8 alkyl, phenyl or C1–8 alkyl substituted with phenyl or $R^9$ is taken together with $R^7$ to form C2–6 alkylene, wherein one carbon atom may be replaced by oxygen, sulfur or —$NR^{60}$— and the alkylene may be substituted with —$NR^{61}R^{62}$ or —$OR^{63}$; and when CycA is included in any or all of R, $R^7$, and $R^8$, they may be the same or different and CycA, and CycD, independently, may be substituted with 1–5 of $R^{27}$;

$R^{27}$ is
(1) C1–8 alkyl,
(2) halogen,
(3) —$NR^{11}R^{12}$,
(4) —$OR^{13}$,
(5) a C5–10 mono-or bi-cyclic carboring,
(6) nitro,
(7) $CF_3$,
(8) cyano,
(10) —$COR^{15}$,
(11) oxo,
(12) —$SO_2R^{15}$,
(13) —$OCF_3$ or
(14) C1–8 alkyl substituted with 1–5 of a group selected from the following (a) to (k):
(a) halogen, (b) —$NR^{11}R^{12}$, (c) —$OR^{13}$, (d) a C5–10 mono- or bi-cyclic carboring,
(e) nitro, (f) $CF_3$, (g) cyano,
(h) —$SR^{14}$, (i) —$COR^{15}$, (j) —$SO_2R^{15}$, and (k) —$OCF_3$,
wherein $R^{11}$ and $R^{12}$ are the same or different and represent hydrogen, C1–4 alkyl, —COO—(C1–4 alkyl), phenyl or C1–4 alkyl substituted with phenyl, $R^{13}$ and $R^{14}$ are the same or different and represent hydrogen, C1–4 alkyl, phenyl or C1–4 alkyl substituted with phenyl, $R^{15}$ is C1–4 alkyl, phenyl, —NR$^{11}$R$^{12}$, wherein all symbols have the same meanings as above, —OR$^{13}$, wherein R$^{13}$ has the same meaning as above, or C1–4 alkyl substituted with phenyl, or a non-toxic salt thereof.

2. The compound according to claim 1, wherein R is (i) hydrogen,
(ii) C1–8 alkyl,
(iii) CycA,
(iv) C1–8 alkyl substituted with a group selected from CycA or nitro, (v) 

(vi) 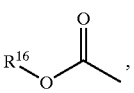

(vii) 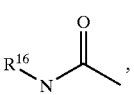

(viii) 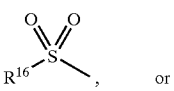, or (ix) 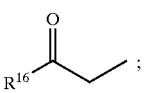;

CycA is a mono-, bi- or tri-cyclic C3–15 carboring optionally substituted with 1–5 of R$^{27}$, R$^{27}$ is
(1) C1–8 alkyl,
(2) halogen,
(3) —NR$^{11}$R$^{12}$,
(4) —OR$^{13}$,
(5) phenyl,
(6) nitro,
(7) CF$_3$,
(8) cyano,
(9) —SR$^{14}$,
(10) —COR$^{15}$,
(11) oxo, or
(12) C1–8 alkyl substituted with 1–5 groups selected from the following (a) to (i):
(a) halogen, (b) —NR$^{11}$R$^{12}$, (c) —OR$^{13}$, (d) phenyl, (e) nitro, (f) CF$_3$, (g) cyano, SR$^4$, and (i) COR$^{15}$, wherein all symbols have the same meanings as in claim 1, R$^{16}$ is
(1) C1–8 alkyl,
(2) C2–8 alkenyl,
(3) C2–8 alkynyl,
(4) CycA,
(5) C1–8 alkyl substituted with a group selected from CycA and —NHC(O)—CycA,
(6) C2–8 alkenyl substituted with CycA, or
(7) C2–8 alkynyl substituted with CycA, or a non-toxic salt thereof.

3. The compound according to claim 2,
wherein R is C1–8 alkyl or C1–8 alkyl substituted with a group selected from CycA or nitro,

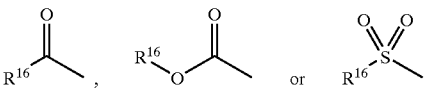

or a non-toxic salt thereof.

4. The compound according to claim 3,
wherein R$^{16}$ is C1–8 alkyl, C2–8 alkenyl, C2–8 alkynyl, CycA, or C1–8 alkyl, C2–8 alkenyl or C2–8 alkynyl substituted with CycA,
and wherein CycA is a C5–10 mono- or bi-cyclic carboaryl or partially or completely saturated one thereof or a non-toxic salt thereof.

5. The compound according to claim 1, wherein R$^{16}$ is C1–8 alkyl, C2–8 alkenyl or C2–8 alkynyl substituted with a group selected from halogen, CF$_3$, nitro, cyano or NR$^{18}$R$^{19}$, or a non-toxic salt thereof.

6. The compound according to claim 1, wherein R$^{16}$ is
(1) CycA containing 1–5 of substituent R$^{27}$ or
(2) C1–8 alkyl, C2–8 alkenyl or C2–8 alkynyl substituted with CycA containing 1–5 of substituent R$^{27}$ or C2–8 alkynyl,
wherein at least one of R$^{27}$ in (1) and (2) is selected from
(i) a C5–10 mono- or bi-carboring,
(ii) —SO$_2$R$^{15}$,
(iii) —OCF$_3$, or
(iv) C1–8 alkyl substituted with 1–5 of a group selected from (a) halogen, (b) —NR$^{11}$R$^{12}$, (c) —OR$^{13}$, (d) a C5–10 mono- or bi-cyclic carboring, (e) nitro, (f) CF$_3$, (g) cyano, (h) —SR$^{14}$, (i) —COR$^{15}$, (j) —SO$_2$R$^{15}$ and (k) —OCF$_3$, provided that at least one of the group substituting the C1–8 alkyl is selected from a C5–10 mono- or bi-cyclic carboring, —SO$_2$R$^{15}$ or —OCF$_3$, or a non-toxic salt thereof.

7. The compound according to claim 1, wherein W is oxygen or a non-toxic salt thereof.

8. The compound according to claim 1, wherein W is sulfur or a non-toxic salt thereof.

9. The compound according to claim 1, which is selected from:
(1) 1-[(1R,2S)-2-(benzoylamino)cyclohexyl]-N-[(2S)-4-methyl-1-oxo-1-(2-oxo-1,3,4-oxadiazolin-5-yl)-2-pentyl]carboxamide,
(2) N-[4-methyl-1-oxo-1-(2-oxo-1,3,4-oxadiazolin-5-yl)-2-pentyl]cyclohexanecarboxamide,
(3) 1-[(1S,2R)-2-(benzoylamino)cyclohexyl]-N-[4-methyl-1-oxo-1-(2-oxo-1,3,4-oxadiazolin-5-yl)-2-pentyl]carboxamide,
(5) 1-[(1R,2S)-2-(4-methoxybenzoylamino)cyclohexyl]-N-[(2S)-4-methyl-1-oxo-1-(2-oxo-1,3,4-oxadiazolin-5-yl)-2-pentyl]carboxamide,
(6) 1-[(1R,2S)-2-(quinoxalin-2-ylcarbonylamino)cyclohexyl]-N-[(2S)-4-methyl-1-oxo-1-(2-oxo-1,3,4-oxadiazolin-5-yl)-2-pentyl]carboxamide,
(7) 1-[(1R,2S)-2-(naphthalen-2-ylcarbonylamino)cyclohexyl]-N-[(2S)-4-methyl-1-oxo-1-(2-oxo-1,3,4-oxadiazolin-5-yl)-2-pentyl]carboxamide, (8) 1-[(1R,2S)-2-(benzo[b]thiophen-2-ylcarbonylamino) cyclohexyl]-N-[(2S)-4-methyl-1-oxo-1-(2-oxo-1,3,4-oxadiazolin-5-yl)-2-pentyl]carboxamide, (9) 1-[(1R,2S)-2-(4-nitrobenzoylamino)cyclohexyl]-N-[(2S)-4-methyl-1-oxo-1-(2-oxo-1,3,4-oxadiazolin-5-yl)-2-pentyl]carboxamide,

(10) 1-[(1R,2S)-2-(4-chlorobenzoylamino)cyclohexyl]-N-[(2S)-4-methyl-1-oxo-1-(2-oxo-1,3,4-oxadiazolin-5-yl)-2-pentyl]carboxamide,

(11) 1-[(1R,2S)-2-(4-phenylbenzoylamino)cyclohexyl]-N-[(2S)-4-methyl-1-oxo-1-(2-oxo-1,3,4-oxadiazolin-5-yl)-2-pentyl]carboxamide,

(12) 1-[(1R,2S)-2-(4-fluorobenzoylamino)cyclohexyl]-N-[(2S)-4-methyl-1-oxo-1-(2-oxo-1,3,4-oxadiazolin-5-yl)-2-pentyl]carboxamide,

(13) 1-[(1R,2S)-2-(4-t-butylbenzoylamino)cyclohexyl]-N-[(2S)-4-methyl-1-oxo-1-(2-oxo-1,3,4-oxadiazolin-5-yl)-2-pentyl]carboxamide,

(14) 1-[(1R,2S)-2-(4-methylbenzoylamino)cyclohexyl]-N-[(2S)-4-methyl-1-oxo-1-(2-oxo-1,3,4-oxadiazolin-5-yl)-2-pentyl]carboxamide,

(15) 1-[(1R,2S)-2-(4-trifluoromethylbenzoylamino) cyclohexyl]-N-[(2S)-4-methyl-1-oxo-1-(2-oxo-1,3,4-oxadiazolin-5-yl)-2-pentyl]carboxamide,

(16) 1-[(1R,2S)-2-(2-fluorobenzoylamino)cyclohexyl]-N-[(2S)-4-methyl-1-oxo-1-(2-oxo-1,3,4-oxadiazolin-5-yl)-2-pentyl]carboxamide,

(17) 1-[(1R,2S)-2-(pyridin-2-ylcarbonylamino) cyclohexyl]-N-[(2S)-4-methyl-1-oxo-1-(2-oxo-1,3,4-oxadiazolin-5-yl)-2-pentyl]carboxamide,

(18) 1-[(1R,2S)-2-(2-methylthiopyridin-3-ylcarbonylamino)cyclohexyl]-N-[(2S)-4-methyl-1-oxo-1-(2-oxo-1,3,4-oxadiazolin-5-yl)-2-pentyl]carboxamide,

(19) 1-[(1R,2S)-2-(2-chloropyridin-5-ylcarbonylamino) cyclohexyl]-N-[(2S)-4-methyl-1-oxo-1-(2-oxo-1,3,4-oxadiazolin-5-yl)-2-pentyl]carboxamide,

(20) 1-[(1R,2S)-2-(naphthalen-1-ylmethylcarbonylamino) cyclohexyl]-N-[(2S)-4-methyl-1-oxo-1-(2-oxo-1,3,4-oxadiazolin-5-yl)-2-pentyl]carboxamide,

(21) 1-[(1R,2S)-2-(4-cyanobenzoylamino)cyclohexyl]-N-[(2S)-4-methyl-1-oxo-1-(2-oxo-1,3,4-oxadiazolin-5-yl)-2-pentyl]carboxamide,

(22) 1-[(1R,2S)-2-(N-benzoyl-N-methylamino) cyclohexyl]-N-[(2S)-4-methyl-1-oxo-1-(2-oxo-1,3,4-oxadiazolin-5-yl)-2-pentyl]carboxamide,

(23) 1-[(1R,2S)-2-dimethylaminomethylbenzoylamino) cyclohexyl]-N-[4-methyl-1-oxo-1-(2-oxo-1,3,4-oxadiazolin-5-yl)-2-pentyl]carboxamide, or a non-toxic salt thereof.

10. The compound according to claim 1, which is
1-[(1R,2S)-2-(benzoylamino)cyclohexyl]-N-[(2S)-4-methyl-1-oxo-1-(2-thio-1,3,4-oxadiazolin-5-yl)-2-pentyl]carboxamide or a non-toxic salt thereof.

11. A pharmaceutical composition comprising the compound of formula (I) according to claim 1, or a non-toxic salt thereof and a carrier.

12. The pharmaceutical composition according to claim 11, which has activity to inhibit a cysteine protease.

13. The pharmaceutical composition according to claim 12, wherein the cysteine protease is cathepsin K, cathepsin B, cathepsin S, cathepsin L, cathepsin H, calpain or caspase-1.

14. The pharmaceutical composition according to claim 13, wherein the cysteine protease is cathepsin K.

15. The pharmaceutical composition according to claim 13, wherein the cysteine protease is cathepsin S.

16. A method for treatment of bone resorption diseases, comprising administering to a subject an effective amount of a compound of formula (I) according to claim 1, or a non-toxic salt thereof.

17. The method of claim 16, wherein the bone resorption disease is osteoporosis.

* * * * *